US012807728B2

(12) United States Patent
Pei et al.

(10) Patent No.: US 12,807,728 B2
(45) Date of Patent: Nov. 24, 2026

(54) ANTIBODIES TO TNFR2 AND USES THEREOF

(71) Applicant: NOVAROCK BIOTHERAPEUTICS, LTD., Ewing, NJ (US)

(72) Inventors: Yi Pei, Paoli, PA (US); Haichun Huang, Fremont, CA (US); Ming Lei, Princeton, NJ (US); Han Li, Newtown, PA (US); Chi Shing Sum, Newtown, PA (US); Alla Pritsker, Morganville, NJ (US); Bor-Ruei Lin, West Orange, NJ (US); Fangqiang Tang, Princeton, NJ (US)

(73) Assignee: NOVAROCK BIOTHERAPEUTICS, LTD., Ewing, NJ (US)

( * ) Notice: Subject to any disclaimer, the term of this patent is extended or adjusted under 35 U.S.C. 154(b) by 537 days.

(21) Appl. No.: 18/270,350

(22) PCT Filed: Dec. 30, 2021

(86) PCT No.: PCT/US2021/065649
§ 371 (c)(1),
(2) Date: Jun. 29, 2023

(87) PCT Pub. No.: WO2022/147222
PCT Pub. Date: Jul. 7, 2022

(65) Prior Publication Data

US 2024/0067740 A1 Feb. 29, 2024

Related U.S. Application Data

(60) Provisional application No. 63/166,042, filed on Mar. 25, 2021, provisional application No. 63/132,584, filed on Dec. 31, 2020.

(51) Int. Cl.

| | |
|---|---|
| ***C07K 16/28*** | (2006.01) |
| ***A61K 39/00*** | (2006.01) |
| ***A61P 35/00*** | (2006.01) |

(52) U.S. Cl.
CPC .......... *C07K 16/2878* (2013.01); *A61P 35/00* (2018.01); *C07K 16/2818* (2013.01); *A61K 2039/505* (2013.01); *A61K 2039/507* (2013.01); *C07K 2317/21* (2013.01); *C07K 2317/33* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 2016/0145343 | A1* | 5/2016 | Schoen .............. | C07K 16/2896 435/69.6 |
| 2019/0135929 | A1* | 5/2019 | Faustman .......... | C07K 16/2878 |
| 2019/0202925 | A1 | 7/2019 | Thompson | |
| 2019/0330359 | A1 | 10/2019 | Maury et al. | |

FOREIGN PATENT DOCUMENTS

| | | | |
|---|---|---|---|
| CA | 3117864 | A1 | 5/2020 |
| EP | 3447075 | B1 | 8/2023 |
| WO | 2008036341 | A2 | 3/2008 |
| WO | 2010072741 | A1 | 7/2010 |
| WO | 2020140084 | A1 | 7/2020 |

OTHER PUBLICATIONS

International Search Report and Written Opinion for International Patent Application No. PCT/US2021/065649, mailed on May 17, 2022, 11 pages.
Fischer R et al., "Selective Targeting of TNF Receptors as a Novel Therapeutic Approach." Front Cell Dev Biol. May 26, 2020;8:401.
Torrey H et al. "Targeted killing of TNFR2-expressing tumor cells and Tregs by TNFR2 antagonistic antibodies in advanced Sezary syndrome." Leukemia. May 2019;33(5):1206-1218.

* cited by examiner

*Primary Examiner* — Joanne Hama
*Assistant Examiner* — Rudolph E. Sloup, Jr. IV
(74) *Attorney, Agent, or Firm* — Morgan, Lewis & Bockius LLP

(57) ABSTRACT

The present disclosure provides antibodies and antibody fragments thereof that bind to human TNFR2. The disclosed antibodies, inhibit the TNF-TNFR2 signaling axis and enhance cytokine secretion in T effector cells and are therefore useful for the treatment of cancer, either alone or in combination with other agents.

17 Claims, 17 Drawing Sheets

Specification includes a Sequence Listing.

FIG. 1A

SEQ ID NO: 1 R2-1_VH
QVQLVESGGGVVQPGRSLRLSCAASGFTFSSYGMHWVRQAPGKGLEWVAVIWFDEDNKDYADSVKGR
FTISRDNSKNTLYLQMSSLRAEDTAVYYCARDNDILTGYYYYYGMDVWGQGTTVTVSS

| | | |
|---|---|---|
| SYGMH | VIWFDEDNKDYADSVKG | DNDILTGYYYYYGMDV |
| SEQ: 13 | SEQ: 14 | SEQ: 15 |

SEQ ID NO: 2 R2-1_VL
DIQLTQSPSFLSASVGDRVTITCRASQDISSYLAWYQQKPGKAPKLLIYAASTLQSGVPSRFSGSGSGTEF
TLTISSLQPEDFATYYCQQLNSYPPTFGQGTKVEIK

| | | |
|---|---|---|
| RASQDISSYLA | AASTLQS | QQLNSYPPT |
| SEQ: 16 | SEQ: 17 | SEQ: 18 |

SEQ ID NO: 3 R2-2_VH
QVQLVQSGPEVKKPGASVKVSCKASGYTFTNYGISWVRQAPGQGLEWMGWINAYNGNTNYAQKLQGR
VTMTTDTSTSTAYMELRSLRSDDTAVYYCARDGGYGSGTYHNDYYYYYGMDVWGQGTTVTVSS

| | | |
|---|---|---|
| NYGIS | WINAYNGNTNYAQKLQG | DGGYGSGTYHNDYYYYYGMDV |
| SEQ: 19 | SEQ: 20 | SEQ: 21 |

SEQ ID NO:4 R2-2_VL
EIVLTQSPDFQSMTPEEKVTITCRASQSIGSNLHWYQQKPDQSPKLLIKFASQSISGVPSRFSGSGSGTDF
TLTINSLEAEDAATYYCHQSSSLPFTFGPGTKVDIK

| | | |
|---|---|---|
| RASQSIGSNLH | FASQSIS | HQSSSLPFT |
| SEQ: 22 | SEQ: 23 | SEQ: 24 |

SEQ ID NO: 5 R2-3_VH
QVQLQESGPGLVKPSETLSLTCTVSGGSISSYYWSWIRQAPGKGLEWIGYIYYSGSTNYNPSLKSRVTIS
VDTSKNQFSLKLSSVTAADTAVYYCARDDGSSDYGMDVWGQGTTVTVSS

| | | |
|---|---|---|
| SYYWS | YIYYSGSTNYNPSLKS | DDGSSDYGMDV |
| SEQ: 25 | SEQ: 26 | SEQ: 27 |

SEQ ID NO: 6 R2-3_VL
AIQLTQSPSSLSASVGDRVTITCRASQGISSALAWYQQKPGKAPKLLIYDASSLESGVPSRFTGSGTDFTL
TISSLQPEDFATYYCQQFNNYMYTFGQGTKLEIK

| | | |
|---|---|---|
| RASQGISSALA | DASSL | QQFNNYMYT |
| SEQ: 28 | SEQ: 29 | SEQ: 30 |

FIG. 1B

SEQ ID NO: 7 R2-4_VH
QVQLVQSGAEVRKPGASVKVSCKASGYTFTSYSVTWVRQAPGQGLEWMGWINAFSGNTHYAQNLQDR
VTMTTDTSTSTAYMELRSLRSDDTAVYYCAREEGSGSYEDYYGMDVWGQGTTVTVSS

| | | |
|---|---|---|
| SYSVT | WINAFSGNTHYAQNLQD | EEGSGSYEDYYGMDV |
| SEQ: 31 | SEQ: 32 | SEQ: 33 |

SEQ ID NO: 8 R2-4_VL
DIVMTQTPLSSPVTLGQPASISCRSSQSLVHSDGNTYLSWLQQRPGQPPRLLIYKISNRFSGVPDRFSGS
GAGTDFTLKISRVEAEDVGVYYCMQTTQFPFTFGPGTKVDIK

| | | |
|---|---|---|
| RSSQSLVHSDGNTYLS | KISNRFS | MQTTQFPFT |
| SEQ: 34 | SEQ: 35 | SEQ: 36 |

SEQ ID NO: 9 R2-5_VH
QVQLVQSGAEVKKPGASVTVSCKASGYTFSTYGIIWVRQAPGQGLEWMGWISAFNGNANSAQKLQDRV
TMTTDTSTSTAYMELRSLRSDDTAVYYCARGEDFFDYWGQGTLVTVSS

| | | |
|---|---|---|
| TYGII | WISAFNGNANSAQKLQD | GEDFFDY |
| SEQ: 37 | SEQ: 38 | SEQ: 39 |

SEQ ID NO: 10 R2-5_VL
DIVMTQTPLSSPVTLGQPASISCRSSQSLVHSDGNTYLSWLQQRPGQPPRLLIYKVSSRFSGVPDRFSGS
GAGTDFTLKISRVEAEDVGVYYCTQSTQFPFTFGRGTKLEIK

| | | |
|---|---|---|
| RSSQSLVHSDGNTYLS | KVSSRFS | TQSTQFPFT |
| SEQ: 34 | SEQ: 40 | SEQ: 41 |

SEQ ID NO: 11 R2-6_VH
QVQLVQSGAEVKKPGASVKVSCKASGYTFLSYGLSWVRQAPGQGLEWMGWINAYNGNTNYAQNLQDR
VTMTTDTSTSTAYMELRSLRSDDMAVYYCARWDILTAYYSSDAFDIWGQGTMVTVSS

| | | |
|---|---|---|
| SYGLS | WINAYNGNTNYAQNLQD | WDILTAYYSSDAFDI |
| SEQ: 42 | SEQ: 43 | SEQ: 44 |

SEQ ID NO: 12 R2-6_VL
DIVMTQTPLSSPVTLGQPASISCRSSQSLVHSDGNTYLNWLQQRPGQPPRLLIYKVSNRFSGVPDRFSGS
GAGTDFTLKISRVEAEDVGVYYCTQTTQFPITFGQGTRLEIK

| | | |
|---|---|---|
| RSSQSLVHSDGNTYLN | KVSNRFS | TQTTQFPIT |
| SEQ: 45 | SEQ: 46 | SEQ: 47 |

FIG. 1C

SEQ ID NO: 48 R2-5.1 VH
QVQLVQSGAEVKKPGASVTVSCKASGYTFSTYGIIWVRQAPGQGLEWMGWISAFNSNANSAQKLQDRV
TMTTDTSTSTAYMELRSLRSDDTAVYYCARGEDFFDYWGQGTLVTVSS

| TYGII | WISAFNSNANSAQKLQD | GEDFFDY |
|---|---|---|
| SEQ: 37 | SEQ: 49 | SEQ: 39 |

SEQ ID NO: 50 human IgG1 constant domain

ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

SEQ ID NO: 51 human Kappa constant domain

RTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

SEQ ID NO:52 >NP_001057.1 tumor necrosis factor receptor superfamily member 1B precursor [Homo sapiens]

MAPVAVWAALAVGLELWAAAHALPAQVAFTPYAPEPGSTCRLREYYDQTAQMCCSKCSPGQHAKVFCTKTSDTVCD
SCEDSTYTQLWNWVPECLSCGSRCSSDQVETQACTREQNRICTCRPGWYCALSKQEGCRLCAPLRKCRPGFGVARPG
TETSDVVCKPCAPGTFSNTTSSTDICRPHQICNVVAIPGNASMDAVCTSTSPTRSMAPGAVHLPQPVSTRSQHTQPTPE
PSTAPSTSFLLPMGPSPPAEGSTGDFALPVGLIVGVTALGLLIIGVVNCVIMTQVKKKPLCLQREAKVPHLPADKARGTQ
GPEQQHLLITAPSSSSSSLESSASALDRRAPTRNQPQAPGVEASGAGEARASTGSSDSSPGGHGTQVNVTCIVNVCSSS
DHSSQCSSQASSTMGDTDSSPSESPKDEQVPFSKEECAFRSQLETPETLLGSTEEKPLPLGVPDAGMKPS

SEQ ID NO:53 >XP_005544817.1 PREDICTED: tumor necrosis factor receptor superfamily member 1B isoform X1 [Macaca fascicularis]

MAPAAVWAALAVGLELWAAGHALPAQVAFTPYAPEPGGTCRLREYYDQTAQMCCSKCPPGQHAKVFCTKTSDTVC
DSCEDSTYTQLWNWVPECLSCGSRCSSDQVETQACTREQNRICTCRPGWYCALSKQEGCRLCAQLRKCRPGFGVARP
GTETSDVVCKPCAPGTFSNTTSSTDICRPHQICHVVAIPGNASMDAVCTSTSPTRSMAPGAVHLPQPVSTRSQHTQPTP
APSTAPGTSFLLPVGPSPPAEGSTGDIVLPVGLIVGVTALGLLIIGVVNCVIMTQVKKKPLCLQRETKVPHLPADKARGAQ
GPEQQHLLTTVPSSSSSSLESSASALDRRAPTRNQPQAPGAEKASGAGEARASTGSSADSSPGGHGTQVNVTCIVNVCS
SSDHSSQCSSQASSTMGDTDASPSGSPKDEQVPFSKEESAFRSQLETPETLLGSTEEKPLPLGVPDAGMKPS

FIG. 1D

SEQ ID NO:54 >NP_035740.2 tumor necrosis factor receptor superfamily member 1B precursor [Mus musculus]

MAPAALWVALVFELQLWATGHTVPAQVVLTPYKPEPGYECQISQEYYDRKAQMCCAKCPPGQYVKHFCNKTSDTVC
ADCEASMYTQVWNQFRTCLSCSSSCTTDQVEIRACTKQQNRVCACEAGRYCALKTHSGSCRQCMRLSKCGPGFGVAS
SRAPNGNVLCKACAPGTFSDTTSSTDVCRPHRICSILAIPGNASTDAVCAPESPTLSAIPRTLYVSQPEPTRSQPLDQEPG
PSQTPSILTSLGSTPIIEQSTKGGISLPIGLIVGVTSLGLLMLGLVNCIILVQRKKKPSCLQRDAKVPHVPDEKSQDAVGLEQ
QHLLTTAPSSSSSSLESSASAGDRRAPPGGHPQARVMAEAQGFQEARASSRISDSSHGSHGTHVNVTCIVNVCSSSDHS
SQCSSQASATVGDPDAKPSASPKDEQVPFSQEECPSQSPCETTETLQSHEKPLPLGVPDMGMKPSQAGWFDQIAVKV
A

SEQ ID NO:55 >NP_001056.1 tumor necrosis factor receptor superfamily member 1A isoform 1 precursor [Homo sapiens]

MGLSTVPDLLLPLVLLELLVGIYPSGVIGLVPHLGDREKRDSVCPQGKYIHPQNNSICCTKCHKGTYLYNDCPGPGQDTD
CRECESGSFTASENHLRHCLSCSKCRKEMGQVEISSCTVDRDTVCGCRKNQYRHYWSENLFQCFNCSLCLNGTVHLSC
QEKQNTVCTCHAGFFLRENECVSCSNCKKSLECTKLCLPQIENVKGTEDSGTTVLLPLVIFFGLCLLSLLFIGLMYRYQRWK
SKLYSIVCGKSTPEKEGELEGTTTKPLAPNPSFSPTPGFTPTLGFSPVPSSTFTSSSTYTPGDCPNFAAPRREVAPPYQGAD
PILATALASDPIPNPLQKWEDSAHKPQSLDTDDPATLYAVVENVPPLRWKEFVRRLGLSDHEIDRLELQNGRCLREAQYS
MLATWRRRTPRREATLELLGRVLRDMDLLGCLEDIEEALCGPAALPPAPSLLR

SEQ ID NO:56 >NP_000585.2 tumor necrosis factor [Homo sapiens]

MSTESMIRDVELAEEALPKKTGGPQGSRRCLFLSLFSFLIVAGATTLFCLLHFGVIGPQREEFPRDLSLISPLAQAVRSSSRT
PSDKPVAHVVANPQAEGQLQWLNRRANALLANGVELRDNQLVVPSEGLYLIYSQVLFKGQGCPSTHVLLTHTISRIAVS
YQTKVNLLSAIKSPCQRETPEGAEAKPWYEPIYLGGVFQLEKGDRLSAEINRPDYLDFAESGQVYFGIIAL

SEQ ID NO:57 Membrane-bound tumor necrosis factor [Homo sapiens]

MSTESMIRDVELAEEALPKKTGGPQGSRRCLFLSLFSFLIVAGATTLFCLLHFGVIGPQREEFPRDLSLISPLAQAVAHVVA
NPQAEGQLQWLNRRANALLANGVELRDNQLVVPSEGLYLIYSQVLFKGQGCPSTHVLLTHTISRIAVSYQTKVNLLSAIK
SPCQRETPEGAEAKPWYEPIYLGGVFQLEKGDRLSAEINRPDYLDFAESGQVYFGIIAL

SEQ ID NO: 58 Mouse IgG1 constant domain

AKTTPPSVYPLAPGSAAQTNSMVTLGCLVKGYFPEPVTVTWNSGSLSSGVHTFPAVLQSDLYTLSSSVTV
PSSTWPSETVTCNVAHPASSTKVDKKIVPRDCGCKPCICTVPEVSSVFIFPPKPKDVLTITLTPKVTCVVVD
ISKDDPEVQFSWFVDDVEVHTAQTQPREEQFNSTFRSVSELPIMHQDWLNGKEFKCRVNSAAFPAPIEK
TISKTKGRPKAPQVYTIPPPKEQMAKDKVSLTCMITDFFPEDITVEWQWNGQPAENYKNTQPIMDTDGSY
FVYSKLNVQKSNWEAGNTFTCSVLHEGLHNHHTEKSLSHSPGK

FIG. 1E

SEQ ID NO: 59 Mouse IgG2a constant domain

AKTTAPSVYPLAPVCGDTTGSSVTLGCLVKGYFPEPVTLTWNSGSLSSGVHTFPAVLQSDLYTLSSSVTV
TSSTWPSQSITCNVAHPASSTKVDKKIEPRGPTIKPCPPCKCPAPNLLGGPSVFIFPPKIKDVLMISLSPIVT
CVVVDVSEDDPDVQISWFVNNVEVHTAQTQTHREDYNSTLRVVSALPIQHQDWMSGKEFKCKVNNKDL
PAPIERTISKPKGSVRAPQVYVLPPPEEEMTKKQVTLTCMVTDFMPEDIYVEWTNNGKTELNYKNTEPVL
DSDGSYFMYSKLRVEKKNWVERNSYSCSVVHEGLHNHHTTKSFSRTPGK

SEQ ID NO: 60 Mouse IgG1 D265A constant domain

AKTTPPSVYPLAPGSAAQTNSMVTLGCLVKGYFPEPVTVTWNSGSLSSGVHTFPAVLQSDLYTLSSSVTV
PSSTWPSETVTCNVAHPASSTKVDKKIVPRDCGCKPCICTVPEVSSVFIFPPKPKDVLTITLTPKVTCVVVA
ISKDDPEVQFSWFVDDVEVHTAQTQPREEQFNSTFRSVSELPIMHQDWLNGKEFKCRVNSAAFPAPIEK
TISKTKGRPKAPQVYTIPPPKEQMAKDKVSLTCMITDFFPEDITVEWQWNGQPAENYKNTQPIMDTDGSY
FVYSKLNVQKSNWEAGNTFTCSVLHEGLHNHHTEKSLSHSPGK

FIG. 2
A.
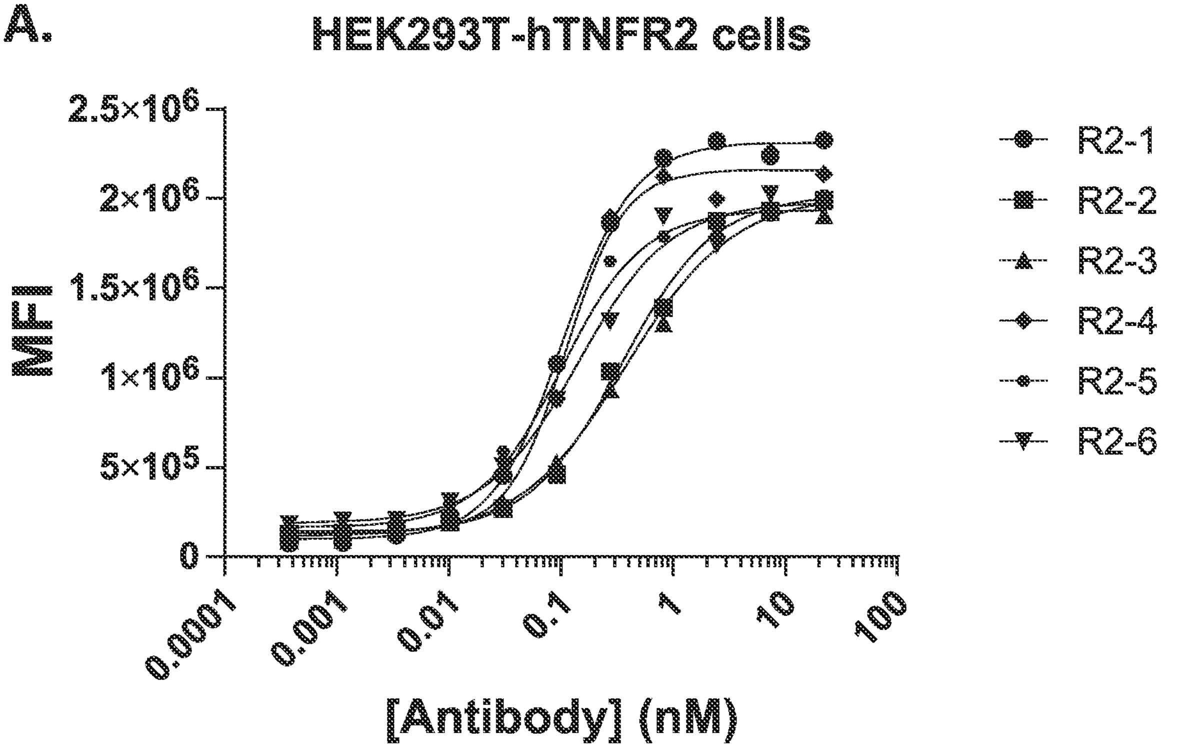
B.
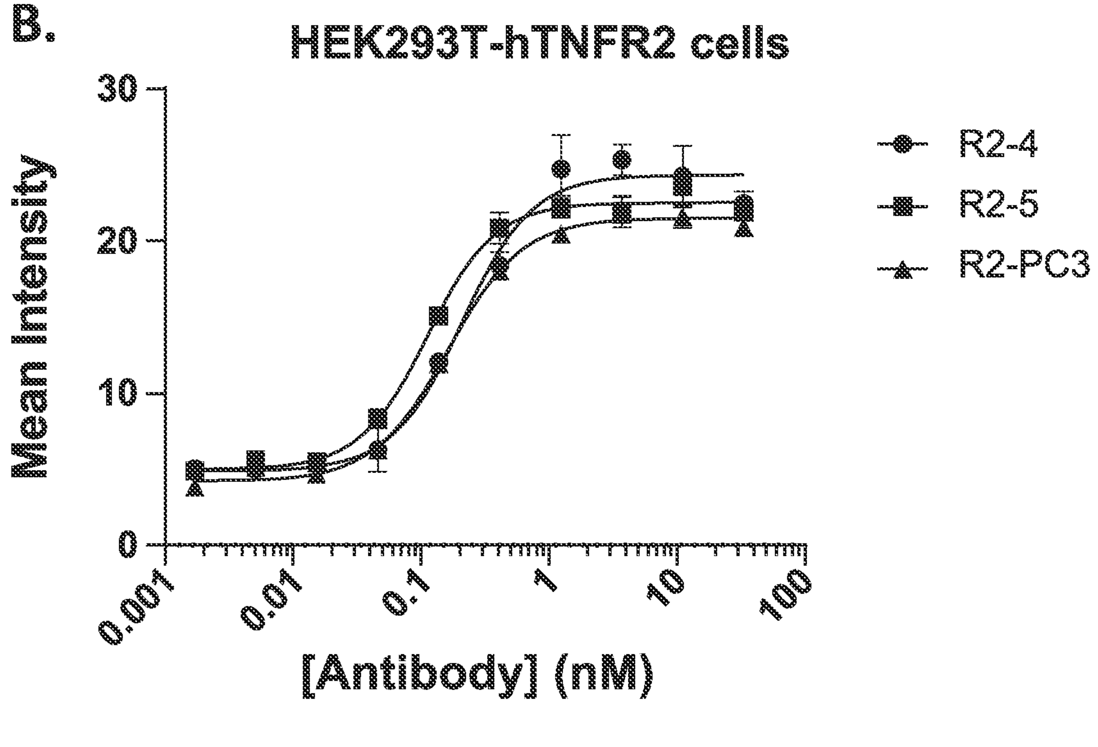

FIG. 10
A.
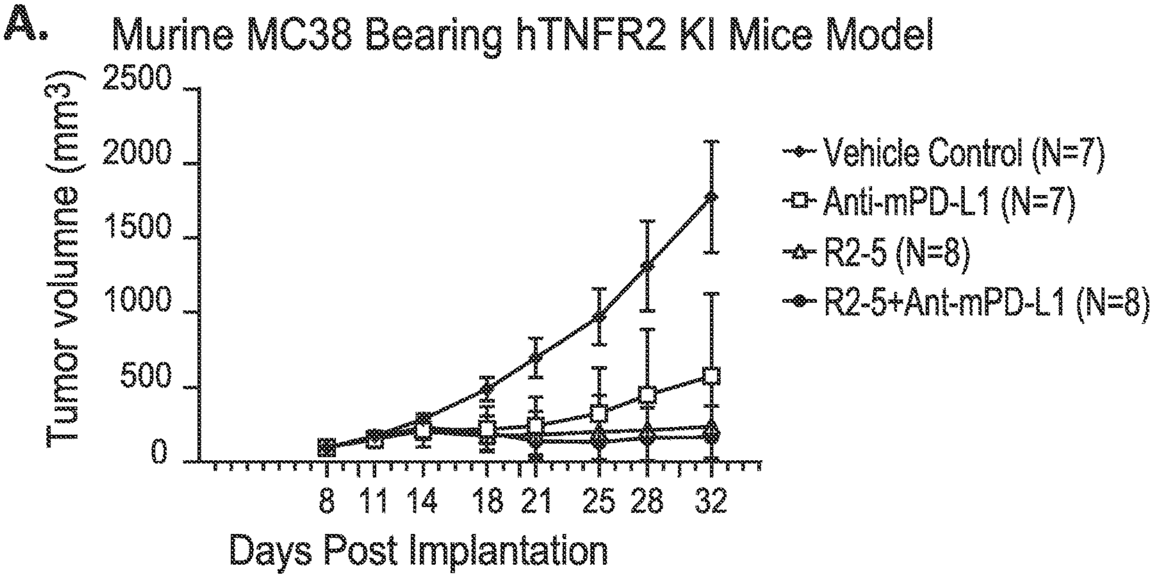
B.
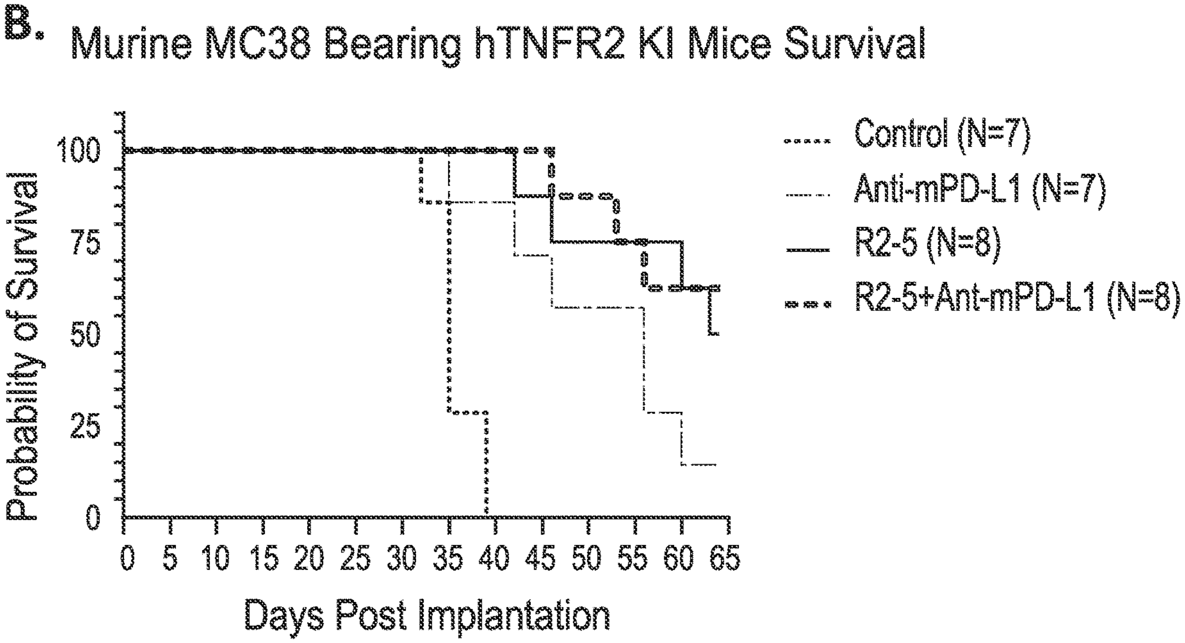

SEQUENCE LISTING

```
<160> NUMBER OF SEQ ID NOS: 60

<210> SEQ ID NO 1
<211> LENGTH: 125
<212> TYPE: PRT
<213> ORGANISM: Artificial Sequence
<220> FEATURE:
<223> OTHER INFORMATION: Synthetic Sequence (R2-1_VH)

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Glu Asp Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Asn Asp Ile Leu Thr Gly Tyr Tyr Tyr Tyr Tyr Gly Met
            100                 105                 110

Asp Val Trp Gly Gln Gly Thr Thr Val Thr Val Ser Ser
        115                 120                 125


<210> SEQ ID NO 2
<211> LENGTH: 107
<212> TYPE: PRT
```

<213> ORGANISM: Artificial Sequence
<220> FEATURE:
<223> OTHER INFORMATION: Synthetic Sequence (R2-1_VL)

<400> SEQUENCE: 2

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gln Gly Thr Lys Val Glu Ile Lys
            100                 105
```

<210> SEQ ID NO 3
<211> LENGTH: 130
<212> TYPE: PRT
<213> ORGANISM: Artificial Sequence
<220> FEATURE:
<223> OTHER INFORMATION: Synthetic Sequence (R2-2_VH)

<400> SEQUENCE: 3

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Asn Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Gly Tyr Gly Ser Gly Thr Tyr His Asn Asp Tyr Tyr
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 4
<211> LENGTH: 107
<212> TYPE: PRT
<213> ORGANISM: Artificial Sequence
<220> FEATURE:
<223> OTHER INFORMATION: Synthetic Sequence (R2-2_VL)

<400> SEQUENCE: 4

```
Glu Ile Val Leu Thr Gln Ser Pro Asp Phe Gln Ser Met Thr Pro Glu
1               5                   10                  15

Glu Lys Val Thr Ile Thr Cys Arg Ala Ser Gln Ser Ile Gly Ser Asn
            20                  25                  30
```

```
Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Phe
                85                  90                  95

Thr Phe Gly Pro Gly Thr Lys Val Asp Ile Lys
            100                 105


<210> SEQ ID NO 5
<211> LENGTH: 119
<212> TYPE: PRT
<213> ORGANISM: Artificial Sequence
<220> FEATURE:
<223> OTHER INFORMATION: Synthetic Sequence (R2-3_VH)

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ala Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asp Gly Ser Ser Asp Tyr Gly Met Asp Val Trp Gly Gln Gly
            100                 105                 110

Thr Thr Val Thr Val Ser Ser
        115


<210> SEQ ID NO 6
<211> LENGTH: 105
<212> TYPE: PRT
<213> ORGANISM: Artificial Sequence
<220> FEATURE:
<223> OTHER INFORMATION: Synthetic Sequence (R2-3_VL)

<400> SEQUENCE: 6

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Thr Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Phe Asn Asn Tyr Met Tyr Thr Phe
                85                  90                  95

Gly Gln Gly Thr Lys Leu Glu Ile Lys
```

```
            100                 105
```

<210> SEQ ID NO 7
<211> LENGTH: 124
<212> TYPE: PRT
<213> ORGANISM: Artificial Sequence
<220> FEATURE:
<223> OTHER INFORMATION: Synthetic Sequence (R2-4_VH)

<400> SEQUENCE: 7

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Ser Tyr
            20                  25                  30

Ser Val Thr Trp Val Arg Gln Ala Pro Gly Gln Gly Leu Glu Trp Met
        35                  40                  45

Gly Trp Ile Asn Ala Phe Ser Gly Asn Thr His Tyr Ala Gln Asn Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Gly Ser Gly Ser Tyr Glu Asp Tyr Tyr Gly Met Asp
            100                 105                 110

Val Trp Gly Gln Gly Thr Thr Val Thr Val Ser Ser
        115                 120
```

<210> SEQ ID NO 8
<211> LENGTH: 112
<212> TYPE: PRT
<213> ORGANISM: Artificial Sequence
<220> FEATURE:
<223> OTHER INFORMATION: Synthetic Sequence (R2-4_VL)

<400> SEQUENCE: 8

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Phe Thr Phe Gly Pro Gly Thr Lys Val Asp Ile Lys
            100                 105                 110
```

<210> SEQ ID NO 9
<211> LENGTH: 116
<212> TYPE: PRT
<213> ORGANISM: Artificial Sequence
<220> FEATURE:
<223> OTHER INFORMATION: Synthetic Sequence (R2-5_VH)

<400> SEQUENCE: 9

```
Gln Val Gln Leu Val Gln Ser Gly Ala Glu Val Lys Lys Pro Gly Ala
1               5                   10                  15
```

```
Ser Val Thr Val Ser Cys Lys Ala Ser Gly Tyr Thr Phe Ser Thr Tyr
            20                  25                  30

Gly Ile Ile Trp Val Arg Gln Ala Pro Gly Gln Gly Leu Glu Trp Met
        35                  40                  45

Gly Trp Ile Ser Ala Phe Asn Gly Asn Ala Asn Ser Ala Gln Lys Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Glu Asp Phe Phe Asp Tyr Trp Gly Gln Gly Thr Leu Val
            100                 105                 110

Thr Val Ser Ser
        115


<210> SEQ ID NO 10
<211> LENGTH: 112
<212> TYPE: PRT
<213> ORGANISM: Artificial Sequence
<220> FEATURE:
<223> OTHER INFORMATION: Synthetic Sequence (R2-5_VL)

<400> SEQUENCE: 10

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Ser Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ser
                85                  90                  95

Thr Gln Phe Pro Phe Thr Phe Gly Arg Gly Thr Lys Leu Glu Ile Lys
            100                 105                 110


<210> SEQ ID NO 11
<211> LENGTH: 124
<212> TYPE: PRT
<213> ORGANISM: Artificial Sequence
<220> FEATURE:
<223> OTHER INFORMATION: Synthetic Sequence (R2-6_VH)

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Ser Tyr
            20                  25                  30

Gly Leu Ser Trp Val Arg Gln Ala Pro Gly Gln Gly Leu Glu Trp Met
        35                  40                  45

Gly Trp Ile Asn Ala Tyr Asn Gly Asn Thr Asn Tyr Ala Gln Asn Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
```

```
                85                  90                  95

Ala Arg Trp Asp Ile Leu Thr Ala Tyr Tyr Ser Ser Asp Ala Phe Asp
            100                 105                 110

Ile Trp Gly Gln Gly Thr Met Val Thr Val Ser Ser
        115                 120


<210> SEQ ID NO 12
<211> LENGTH: 112
<212> TYPE: PRT
<213> ORGANISM: Artificial Sequence
<220> FEATURE:
<223> OTHER INFORMATION: Synthetic Sequence (R2-6_VL)

<400> SEQUENCE: 12

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Thr
                85                  90                  95

Thr Gln Phe Pro Ile Thr Phe Gly Gln Gly Thr Arg Leu Glu Ile Lys
            100                 105                 110


<210> SEQ ID NO 13
<211> LENGTH: 5
<212> TYPE: PRT
<213> ORGANISM: Artificial Sequence
<220> FEATURE:
<223> OTHER INFORMATION: Synthetic Sequence (R2-1_VH)

<400> SEQUENCE: 13

Ser Tyr Gly Met His
1               5


<210> SEQ ID NO 14
<211> LENGTH: 17
<212> TYPE: PRT
<213> ORGANISM: Artificial Sequence
<220> FEATURE:
<223> OTHER INFORMATION: Synthetic Sequence (R2-1_VH)

<400> SEQUENCE: 14

Val Ile Trp Phe Asp Glu Asp Asn Lys Asp Tyr Ala Asp Ser Val Lys
1               5                   10                  15

Gly


<210> SEQ ID NO 15
<211> LENGTH: 16
<212> TYPE: PRT
<213> ORGANISM: Artificial Sequence
<220> FEATURE:
<223> OTHER INFORMATION: Synthetic Sequence (R2-1_VH)

<400> SEQUENCE: 15

Asp Asn Asp Ile Leu Thr Gly Tyr Tyr Tyr Tyr Tyr Gly Met Asp Val
1               5                   10                  15
```

<210> SEQ ID NO 16
<211> LENGTH: 11
<212> TYPE: PRT
<213> ORGANISM: Artificial Sequence
<220> FEATURE:
<223> OTHER INFORMATION: Synthetic Sequence (R2-1_VL)

<400> SEQUENCE: 16

Arg Ala Ser Gln Asp Ile Ser Ser Tyr Leu Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: Synthetic Sequence (R2-1_VL)

<400> SEQUENCE: 17

Ala Ala Ser Thr Leu Gln Ser
1 5

<210> SEQ ID NO 18
<211> LENGTH: 9
<212> TYPE: PRT
<213> ORGANISM: Artificial Sequence
<220> FEATURE:
<223> OTHER INFORMATION: Synthetic Sequence (R2-1_VL)

<400> SEQUENCE: 18

Gln Gln Leu Asn Ser Tyr Pro Pro Thr
1 5

<210> SEQ ID NO 19
<211> LENGTH: 5
<212> TYPE: PRT
<213> ORGANISM: Artificial Sequence
<220> FEATURE:
<223> OTHER INFORMATION: Synthetic Sequence (R2-2_VH)

<400> SEQUENCE: 19

Asn Tyr Gly Ile Ser
1 5

<210> SEQ ID NO 20
<211> LENGTH: 17
<212> TYPE: PRT
<213> ORGANISM: Artificial Sequence
<220> FEATURE:
<223> OTHER INFORMATION: Synthetic Sequence (R2-2_VH)

<400> SEQUENCE: 20

Trp Ile Asn Ala Tyr Asn Gly Asn Thr Asn Tyr Ala Gln Lys Leu Gln
1 5 10 15

Gly

<210> SEQ ID NO 21
<211> LENGTH: 21
<212> TYPE: PRT
<213> ORGANISM: Artificial Sequence
<220> FEATURE:
<223> OTHER INFORMATION: Synthetic Sequence (R2-2_VH)

<400> SEQUENCE: 21

Asp Gly Gly Tyr Gly Ser Gly Thr Tyr His Asn Asp Tyr Tyr Tyr Tyr

```
1               5                   10                  15

Tyr Gly Met Asp Val
            20


<210> SEQ ID NO 22
<211> LENGTH: 11
<212> TYPE: PRT
<213> ORGANISM: Artificial Sequence
<220> FEATURE:
<223> OTHER INFORMATION: Synthetic Sequence (R2-2_VL)

<400> SEQUENCE: 22

Arg Ala Ser Gln Ser Ile Gly Ser Asn Leu His
1               5                   10


<210> SEQ ID NO 23
<211> LENGTH: 7
<212> TYPE: PRT
<213> ORGANISM: Artificial Sequence
<220> FEATURE:
<223> OTHER INFORMATION: Synthetic Sequence (R2-2_VL)

<400> SEQUENCE: 23

Phe Ala Ser Gln Ser Ile Ser
1               5


<210> SEQ ID NO 24
<211> LENGTH: 9
<212> TYPE: PRT
<213> ORGANISM: Artificial Sequence
<220> FEATURE:
<223> OTHER INFORMATION: Synthetic Sequence (R2-2_VL)

<400> SEQUENCE: 24

His Gln Ser Ser Ser Leu Pro Phe Thr
1               5


<210> SEQ ID NO 25
<211> LENGTH: 5
<212> TYPE: PRT
<213> ORGANISM: Artificial Sequence
<220> FEATURE:
<223> OTHER INFORMATION: Synthetic Sequence (R2-3_VH)

<400> SEQUENCE: 25

Ser Tyr Tyr Trp Ser
1               5


<210> SEQ ID NO 26
<211> LENGTH: 16
<212> TYPE: PRT
<213> ORGANISM: Artificial Sequence
<220> FEATURE:
<223> OTHER INFORMATION: Synthetic Sequence (R2-3_VH)

<400> SEQUENCE: 26

Tyr Ile Tyr Tyr Ser Gly Ser Thr Asn Tyr Asn Pro Ser Leu Lys Ser
1               5                   10                  15


<210> SEQ ID NO 27
<211> LENGTH: 11
<212> TYPE: PRT
<213> ORGANISM: Artificial Sequence
<220> FEATURE:
<223> OTHER INFORMATION: Synthetic Sequence (R2-3_VH)

<400> SEQUENCE: 27
```

Asp Asp Gly Ser Ser Asp Tyr Gly Met Asp Val
1 5 10

<210> SEQ ID NO 28
<211> LENGTH: 11
<212> TYPE: PRT
<213> ORGANISM: Artificial Sequence
<220> FEATURE:
<223> OTHER INFORMATION: Synthetic Sequence (R2-3_VL)

<400> SEQUENCE: 28

Arg Ala Ser Gln Gly Ile Ser Ser Ala Leu Ala
1 5 10

<210> SEQ ID NO 29
<211> LENGTH: 5
<212> TYPE: PRT
<213> ORGANISM: Artificial Sequence
<220> FEATURE:
<223> OTHER INFORMATION: Synthetic Sequence (R2-3_VL)

<400> SEQUENCE: 29

Asp Ala Ser Ser Leu
1 5

<210> SEQ ID NO 30
<211> LENGTH: 9
<212> TYPE: PRT
<213> ORGANISM: Artificial Sequence
<220> FEATURE:
<223> OTHER INFORMATION: Synthetic Sequence (R2-3_VL)

<400> SEQUENCE: 30

Gln Gln Phe Asn Asn Tyr Met Tyr Thr
1 5

<210> SEQ ID NO 31
<211> LENGTH: 5
<212> TYPE: PRT
<213> ORGANISM: Artificial Sequence
<220> FEATURE:
<223> OTHER INFORMATION: Synthetic Sequence (R2-4_VH)

<400> SEQUENCE: 31

Ser Tyr Ser Val Thr
1 5

<210> SEQ ID NO 32
<211> LENGTH: 17
<212> TYPE: PRT
<213> ORGANISM: Artificial Sequence
<220> FEATURE:
<223> OTHER INFORMATION: Synthetic Sequence (R2-4_VH)

<400> SEQUENCE: 32

Trp Ile Asn Ala Phe Ser Gly Asn Thr His Tyr Ala Gln Asn Leu Gln
1 5 10 15

Asp

<210> SEQ ID NO 33
<211> LENGTH: 15
<212> TYPE: PRT
<213> ORGANISM: Artificial Sequence
<220> FEATURE:
<223> OTHER INFORMATION: Synthetic Sequence (R2-4_VH)

<400> SEQUENCE: 33

Glu Glu Gly Ser Gly Ser Tyr Glu Asp Tyr Tyr Gly Met Asp Val
1 5 10 15

<210> SEQ ID NO 34
<211> LENGTH: 16
<212> TYPE: PRT
<213> ORGANISM: Artificial Sequence
<220> FEATURE:
<223> OTHER INFORMATION: Synthetic Sequence (R2-4_VL)

<400> SEQUENCE: 34

Arg Ser Ser Gln Ser Leu Val His Ser Asp Gly Asn Thr Tyr Leu Ser
1 5 10 15

<210> SEQ ID NO 35
<211> LENGTH: 7
<212> TYPE: PRT
<213> ORGANISM: Artificial Sequence
<220> FEATURE:
<223> OTHER INFORMATION: Synthetic Sequence (R2-4_VL)

<400> SEQUENCE: 35

Lys Ile Ser Asn Arg Phe Ser
1 5

<210> SEQ ID NO 36
<211> LENGTH: 9
<212> TYPE: PRT
<213> ORGANISM: Artificial Sequence
<220> FEATURE:
<223> OTHER INFORMATION: Synthetic Sequence (R2-4_VL)

<400> SEQUENCE: 36

Met Gln Thr Thr Gln Phe Pro Phe Thr
1 5

<210> SEQ ID NO 37
<211> LENGTH: 5
<212> TYPE: PRT
<213> ORGANISM: Artificial Sequence
<220> FEATURE:
<223> OTHER INFORMATION: Synthetic Sequence (R2-5_VH)

<400> SEQUENCE: 37

Thr Tyr Gly Ile Ile
1 5

<210> SEQ ID NO 38
<211> LENGTH: 17
<212> TYPE: PRT
<213> ORGANISM: Artificial Sequence
<220> FEATURE:
<223> OTHER INFORMATION: Synthetic Sequence (R2-5_VH)

<400> SEQUENCE: 38

Trp Ile Ser Ala Phe Asn Gly Asn Ala Asn Ser Ala Gln Lys Leu Gln
1 5 10 15

Asp

<210> SEQ ID NO 39
<211> LENGTH: 7
<212> TYPE: PRT
<213> ORGANISM: Artificial Sequence
<220> FEATURE:
<223> OTHER INFORMATION: Synthetic Sequence (R2-5_VH)

<400> SEQUENCE: 39

Gly Glu Asp Phe Phe Asp Tyr
1 5

<210> SEQ ID NO 40
<211> LENGTH: 7
<212> TYPE: PRT
<213> ORGANISM: Artificial Sequence
<220> FEATURE:
<223> OTHER INFORMATION: Synthetic Sequence (R2-5_VL)

<400> SEQUENCE: 40

Lys Val Ser Ser Arg Phe Ser
1 5

<210> SEQ ID NO 41
<211> LENGTH: 9
<212> TYPE: PRT
<213> ORGANISM: Artificial Sequence
<220> FEATURE:
<223> OTHER INFORMATION: Synthetic Sequence (R2-5_VL)

<400> SEQUENCE: 41

Thr Gln Ser Thr Gln Phe Pro Phe Thr
1 5

<210> SEQ ID NO 42
<211> LENGTH: 5
<212> TYPE: PRT
<213> ORGANISM: Artificial Sequence
<220> FEATURE:
<223> OTHER INFORMATION: Synthetic Sequence (R2-6_VH)

<400> SEQUENCE: 42

Ser Tyr Gly Leu Ser
1 5

<210> SEQ ID NO 43
<211> LENGTH: 17
<212> TYPE: PRT
<213> ORGANISM: Artificial Sequence
<220> FEATURE:
<223> OTHER INFORMATION: Synthetic Sequence (R2-6_VH)

<400> SEQUENCE: 43

Trp Ile Asn Ala Tyr Asn Gly Asn Thr Asn Tyr Ala Gln Asn Leu Gln
1 5 10 15

Asp

<210> SEQ ID NO 44
<211> LENGTH: 15
<212> TYPE: PRT
<213> ORGANISM: Artificial Sequence
<220> FEATURE:
<223> OTHER INFORMATION: Synthetic Sequence (R2-6_VH)

<400> SEQUENCE: 44

Trp Asp Ile Leu Thr Ala Tyr Tyr Ser Ser Asp Ala Phe Asp Ile
1 5 10 15

<210> SEQ ID NO 45
<211> LENGTH: 16
<212> TYPE: PRT
<213> ORGANISM: Artificial Sequence
<220> FEATURE:

<223> OTHER INFORMATION: Synthetic Sequence (R2-6_VL)

<400> SEQUENCE: 45

Arg Ser Ser Gln Ser Leu Val His Ser Asp Gly Asn Thr Tyr Leu Asn
1 5 10 15

<210> SEQ ID NO 46
<211> LENGTH: 7
<212> TYPE: PRT
<213> ORGANISM: Artificial Sequence
<220> FEATURE:
<223> OTHER INFORMATION: Synthetic Sequence (R2-6_VL)

<400> SEQUENCE: 46

Lys Val Ser Asn Arg Phe Ser
1 5

<210> SEQ ID NO 47
<211> LENGTH: 9
<212> TYPE: PRT
<213> ORGANISM: Artificial Sequence
<220> FEATURE:
<223> OTHER INFORMATION: Synthetic Sequence (R2-6_VL)

<400> SEQUENCE: 47

Thr Gln Thr Thr Gln Phe Pro Ile Thr
1 5

<210> SEQ ID NO 48
<211> LENGTH: 116
<212> TYPE: PRT
<213> ORGANISM: Artificial Sequence
<220> FEATURE:
<223> OTHER INFORMATION: Synthetic Sequence (R2-5.1_VH)

<400> SEQUENCE: 48

Gln Val Gln Leu Val Gln Ser Gly Ala Glu Val Lys Lys Pro Gly Ala
1 5 10 15

Ser Val Thr Val Ser Cys Lys Ala Ser Gly Tyr Thr Phe Ser Thr Tyr
20 25 30

Gly Ile Ile Trp Val Arg Gln Ala Pro Gly Gln Gly Leu Glu Trp Met
35 40 45

Gly Trp Ile Ser Ala Phe Asn Ser Asn Ala Asn Ser Ala Gln Lys Leu
50 55 60

Gln Asp Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Gly Glu Asp Phe Phe Asp Tyr Trp Gly Gln Gly Thr Leu Val
100 105 110

Thr Val Ser Ser
115

<210> SEQ ID NO 49
<211> LENGTH: 17
<212> TYPE: PRT
<213> ORGANISM: Artificial Sequence
<220> FEATURE:
<223> OTHER INFORMATION: Synthetic Sequence (R2-5.1_VH)

<400> SEQUENCE: 49

Trp Ile Ser Ala Phe Asn Ser Asn Ala Asn Ser Ala Gln Lys Leu Gln
1 5 10 15

Asp

<210> SEQ ID NO 50
<211> LENGTH: 330
<212> TYPE: PRT
<213> ORGANISM: Homo sapiens

<400> SEQUENCE: 50

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 51
<211> LENGTH: 107
<212> TYPE: PRT
<213> ORGANISM: Homo sapiens

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 461
<212> TYPE: PRT
<213> ORGANISM: Homo sapiens

<400> SEQUENCE: 52

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

```
Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460


<210> SEQ ID NO 53
<211> LENGTH: 463
<212> TYPE: PRT
<213> ORGANISM: Macaca fascicularis

<400> SEQUENCE: 53

Met Ala Pro Ala Ala Val Trp Ala Ala Leu Ala Val Gly Leu Glu Leu
1               5                   10                  15

Trp Ala Ala Gly His Ala Leu Pro Ala Gln Val Ala Phe Thr Pro Tyr
            20                  25                  30

Ala Pro Glu Pro Gly Gly Thr Cys Arg Leu Arg Glu Tyr Tyr Asp Gln
        35                  40                  45

Thr Ala Gln Met Cys Cys Ser Lys Cys Pro Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Gln Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
```

```
                165                 170                 175

Asp Ile Cys Arg Pro His Gln Ile Cys His Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Ala Pro Ser Thr Ala Pro Gly Thr Ser
225                 230                 235                 240

Phe Leu Leu Pro Val Gly Pro Ser Pro Pro Ala Glu Gly Ser Thr Gly
                245                 250                 255

Asp Ile Val Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Thr Lys Val Pro His Leu Pro
    290                 295                 300

Ala Asp Lys Ala Arg Gly Ala Gln Gly Pro Glu Gln Gln His Leu Leu
305                 310                 315                 320

Thr Thr Val Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Ala Glu Lys Ala Ser Gly Ala Gly Glu Ala Arg Ala Ser Thr Gly Ser
        355                 360                 365

Ser Ala Asp Ser Ser Pro Gly Gly His Gly Thr Gln Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ser Thr Met Gly Asp Thr Asp Ala Ser Pro Ser Gly
                405                 410                 415

Ser Pro Lys Asp Glu Gln Val Pro Phe Ser Lys Glu Glu Ser Ala Phe
            420                 425                 430

Arg Ser Gln Leu Glu Thr Pro Glu Thr Leu Leu Gly Ser Thr Glu Glu
        435                 440                 445

Lys Pro Leu Pro Leu Gly Val Pro Asp Ala Gly Met Lys Pro Ser
    450                 455                 460


<210> SEQ ID NO 54
<211> LENGTH: 474
<212> TYPE: PRT
<213> ORGANISM: Mus musculus

<400> SEQUENCE: 54

Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80
```

```
Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Gly Leu Ile Val Gly Val Thr Ser Leu
            260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
    290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
        355                 360                 365

Ile Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
                405                 410                 415

Ser Pro Lys Asp Glu Gln Val Pro Phe Ser Gln Glu Glu Cys Pro Ser
            420                 425                 430

Gln Ser Pro Cys Glu Thr Thr Glu Thr Leu Gln Ser His Glu Lys Pro
        435                 440                 445

Leu Pro Leu Gly Val Pro Asp Met Gly Met Lys Pro Ser Gln Ala Gly
    450                 455                 460

Trp Phe Asp Gln Ile Ala Val Lys Val Ala
465                 470
```

<210> SEQ ID NO 55
<211> LENGTH: 455
<212> TYPE: PRT

<213> ORGANISM: Homo sapiens

<400> SEQUENCE: 55

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly Leu Val Pro
20 25 30

His Leu Gly Asp Arg Glu Lys Arg Asp Ser Val Cys Pro Gln Gly Lys
35 40 45

Tyr Ile His Pro Gln Asn Asn Ser Ile Cys Cys Thr Lys Cys His Lys
50 55 60

Gly Thr Tyr Leu Tyr Asn Asp Cys Pro Gly Pro Gly Gln Asp Thr Asp
65 70 75 80

Cys Arg Glu Cys Glu Ser Gly Ser Phe Thr Ala Ser Glu Asn His Leu
85 90 95

Arg His Cys Leu Ser Cys Ser Lys Cys Arg Lys Glu Met Gly Gln Val
100 105 110

Glu Ile Ser Ser Cys Thr Val Asp Arg Asp Thr Val Cys Gly Cys Arg
115 120 125

Lys Asn Gln Tyr Arg His Tyr Trp Ser Glu Asn Leu Phe Gln Cys Phe
130 135 140

Asn Cys Ser Leu Cys Leu Asn Gly Thr Val His Leu Ser Cys Gln Glu
145 150 155 160

Lys Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asp Ser
195 200 205

Gly Thr Thr Val Leu Leu Pro Leu Val Ile Phe Phe Gly Leu Cys Leu
210 215 220

Leu Ser Leu Leu Phe Ile Gly Leu Met Tyr Arg Tyr Gln Arg Trp Lys
225 230 235 240

Ser Lys Leu Tyr Ser Ile Val Cys Gly Lys Ser Thr Pro Glu Lys Glu
245 250 255

Gly Glu Leu Glu Gly Thr Thr Thr Lys Pro Leu Ala Pro Asn Pro Ser
260 265 270

Phe Ser Pro Thr Pro Gly Phe Thr Pro Thr Leu Gly Phe Ser Pro Val
275 280 285

Pro Ser Ser Thr Phe Thr Ser Ser Ser Thr Tyr Thr Pro Gly Asp Cys
290 295 300

Pro Asn Phe Ala Ala Pro Arg Arg Glu Val Ala Pro Pro Tyr Gln Gly
305 310 315 320

Ala Asp Pro Ile Leu Ala Thr Ala Leu Ala Ser Asp Pro Ile Pro Asn
325 330 335

Pro Leu Gln Lys Trp Glu Asp Ser Ala His Lys Pro Gln Ser Leu Asp
340 345 350

Thr Asp Asp Pro Ala Thr Leu Tyr Ala Val Val Glu Asn Val Pro Pro
355 360 365

Leu Arg Trp Lys Glu Phe Val Arg Arg Leu Gly Leu Ser Asp His Glu
370 375 380

Ile Asp Arg Leu Glu Leu Gln Asn Gly Arg Cys Leu Arg Glu Ala Gln
385 390 395 400

```
Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 56
<211> LENGTH: 233
<212> TYPE: PRT
<213> ORGANISM: Homo sapiens

<400> SEQUENCE: 56

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 57
<211> LENGTH: 221
<212> TYPE: PRT
<213> ORGANISM: Homo sapiens

<400> SEQUENCE: 57

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30
```

```
Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
    130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
    210                 215                 220


<210> SEQ ID NO 58
<211> LENGTH: 324
<212> TYPE: PRT
<213> ORGANISM: Artificial Sequence
<220> FEATURE:
<223> OTHER INFORMATION: Synthesized: Mouse IgG1 constant domain

<400> SEQUENCE: 58

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175
```

```
Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 59
<211> LENGTH: 330
<212> TYPE: PRT
<213> ORGANISM: Artificial Sequence
<220> FEATURE:
<223> OTHER INFORMATION: Synthesized: Mouse IgG2a constant domain

<400> SEQUENCE: 59

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
```

```
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 60
<211> LENGTH: 324
<212> TYPE: PRT
<213> ORGANISM: Artificial Sequence
<220> FEATURE:
<223> OTHER INFORMATION: Synthesized: Mouse IgG1 D265A constant domain

<400> SEQUENCE: 60

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Ala Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
```

-continued

| | | | | | | | | | | | | | | | |
|---|---|---|---|---|---|---|---|---|---|---|---|---|---|---|---|
| | | | | 245 | | | | | 250 | | | | | 255 | |
| Glu | Trp | Gln | Trp | Asn | Gly | Gln | Pro | Ala | Glu | Asn | Tyr | Lys | Asn | Thr | Gln |
| | | | 260 | | | | | 265 | | | | | 270 | | |
| Pro | Ile | Met | Asp | Thr | Asp | Gly | Ser | Tyr | Phe | Val | Tyr | Ser | Lys | Leu | Asn |
| | | 275 | | | | | 280 | | | | | 285 | | | |
| Val | Gln | Lys | Ser | Asn | Trp | Glu | Ala | Gly | Asn | Thr | Phe | Thr | Cys | Ser | Val |
| | 290 | | | | | 295 | | | | | 300 | | | | |
| Leu | His | Glu | Gly | Leu | His | Asn | His | His | Thr | Glu | Lys | Ser | Leu | Ser | His |
| 305 | | | | | 310 | | | | | 315 | | | | | 320 |
| Ser | Pro | Gly | Lys | | | | | | | | | | | | |

ANTIBODIES TO TNFR2 AND USES THEREOF

CROSS-REFERENCE TO RELATED APPLICATIONS

This patent application is a national stage application of International Patent Application No. PCT/US2021/065649, filed on Dec. 30, 2021, which claims the benefit of and priority to U.S. Provisional Patent Application No. 63/166,042, filed on Mar. 25, 2021 and U.S. Provisional Patent Application No. 63/132,584, filed on Dec. 31, 2020, each of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 122863-5005-US_Sequence_Listing.txt. The text file is about 53.9 KB, was created on or about Jul. 19, 2018, and is being submitted electronically via EFS-Web.

FIELD

The present disclosure is in the field of immunotherapy and relates to antibodies and fragments thereof which bind to the human TNFR2 receptor, to polynucleotide sequences encoding these antibodies and to cells producing them. The disclosure further relates to compositions comprising these antibodies, and to methods of their use to modulate the TNF-TNFR2 axis for cancer immunotherapy.

BACKGROUND

The tumor necrosis factor (TNF) and TNF receptor (TNFR) superfamilies (TNFSF/TNFRSF) play important roles in the modulation of the cellular activities of both immune and non-immune cells (Dostert et al., *Physiol. Rev.,* 99(1):115-160, 2019). Indeed, TNFSF/TNFRSF members control both innate and adaptive immune cells in a manner that is crucial for the coordination of various cellular and molecular mechanisms driving either co-stimulation or co-inhibition of the immune response (Ward-Kavanagh, et al., *Immunity,* 44: 1005-1019, 2016). TNF is enriched in the tumor microenvironment where it facilitates tumor immune escape and promotes tumor growth.

TNF, an inflammatory cytokine, is mainly produced by immune cells (e.g., monocytes, macrophages, and T- and B-cells) and executes its biologic effects through two structurally distinct transmembrane receptors: TNF receptor type I (TNFR1, also known as p55 and TNFRSF1A) and TNF receptor type II (TNFR2, also known as p75 and TNFRSF1B). TNFR1 and TNFR2, have marked differences in expression patterns, structure, signaling mechanisms and functions. Unlike TNFR1 which is ubiquitously expressed on almost all cell types, TNFR2 is expressed on a restricted set of cells including minor subsets of lymphocytes, endothelial cells, and human mesenchymal stem cells. It is speculated that the limited-expression pattern of TNFR2 might result in less toxicity to patients (Dostert et al., *Physiol. Rev.,* 99(1):115-160, 2019).

Importantly, TNFR2 is constitutively expressed on human $CD4^{+}Foxp3^{+}$ regulatory T cells (Tregs). Tregs that express the TNFR2 receptor are potently immunosuppressive in both humans and mice and $TNFR2^{+}$ Tregs are the predominant tumor-infiltrating cells found in human and murine tumors (Torrey et al., *Leukemia,* 33:1206-1218, 2018). In some human cancers, the expression of TNFR2 on infiltrating Tregs is estimated to be 100 times higher than on circulating Tregs in control subjects (Torrey et al., *Leukemia,* 33:1206-1218, 2018). Through TNFR2, TNF preferentially activates, expands, and promotes the phenotypic stability, proliferative expansion and suppressive function of Treg cells in the tumor microenvironment (Shaikh et al., *Front. Immunol.,* 18 Jun. 2018, and Vanamee et al., *Science Signaling*, Vol. 11, Issue 511, eaao4910, 2018).

It has also been reported that TNFR2 is involved in the accumulation of myeloid-derived suppressor cell (MDSC), another immunosuppressive cell, in the TME. Membrane-bound TNF (tmTNF) activation of TNFR2 on myeloid-derived suppressor cells (MDSCs) further contributes to tumor immune evasion and promotes tumor progression (Ba et al. *Int. Immunopharm,* 2017).

In addition to Tregs and MDSCs, TNFR2 is also expressed on some tumor cells, including ovarian cancer, colon cancer, renal carcinoma, Hodgkin lymphoma, and myeloma (Shaikh et al., *Front. Immunol.,* 18 Jun. 2018). TNFR2 is recognized as an oncogene and reports describing the use of antagonistic antibodies to target TNFR2 as a cancer immunotherapy strategy have been recently published (Case et al., *Leukoc. Biol.,* 1-11, 2020, Torrey et al., *Sci. Signal.,* 10:462, 2017, Torrey et al., *Leukemia* 33, 1206-1218, 2019, Yang et al., *J. Leukoc. Biol.,* 1-10, 2020, Mårtensson et al, AACR 2020, Abstract #725, Mårtensson et al. AACR Annual Meeting 2020, Poster #936).

Although TNFR2 expression is low in naïve CD4+ and CD8+ cells, TNFR2 is reported as a potent co-stimulatory molecule expressed on the surface of activated CD8 and CD4 T cells in the tumor microenvironment. TNFR2 engagement promotes their activation, proliferation and cytokine production (Kim. E et al, *J Immunol* Oct. 1, 2004, 173 (7) 4500-4509; and Ye L L, et al. *Front Immunol,* 9:583, 2018). Therefore, agonistic antibody against TNFR2 has the potential to further enhance effector T cell function and their anti-tumor response (Tam et al., *Sci. Transl. Med.,* 11:512, eaax0720, 2019 Mårtensson et al. AACR Annual Meeting 2020, Poster #936, Wei et al., AACR Annual Meeting 2020, Poster #2282).

TNF binding to TNFR2 in the tumor microenvironment induces the expansion and activation Tregs and myeloid-derived suppressor cells (MDSCs), thereby suppressing the immune response of effector T cells (Teffs). Consequently, using either antagonistic or agonistic anti-TNFR2 antibodies to downregulate suppressive cell activity or to upregulate effector cell activity in the TME provide novel strategies in the treatment of cancer.

Although several anti-cancer immunotherapeutics have been approved by the Food and Drug Administration (FDA), to date there is no anti-TNFR2 therapeutics approved by the FDA. Thus, there is an unmet need to provide safe and effective anti-TNFR2 antibodies that alone, or in combination with other agents can be used to modulate the TNF-TNFR2 axis for cancer immunotherapy.

SUMMARY

The present disclosure addresses the above need by providing anti-tumor necrosis factor receptor 2 antibodies (anti-TNFR2 antibodies) and fragments thereof. These antibodies and fragments thereof are characterized by unique sets of CDR sequences, specificity for TNFR2 (and not for TNFR1) and cross-reactivity with cynomolgus TNFR2. More specifically, the disclosure relates to antibodies that bind to human TNFR2, and to their use to modulate the TNF-TNFR2 axis for cancer immunotherapy. The disclosed antibodies may be particularly beneficial for tumor microenvironments enriched in exhausted T cells, suppressive myeloid cells, or regulatory T cells that contribute to anti-PD-1/PD-L1 resistance.

According to some embodiments, the antibody or antibody fragments comprise a set of six complementarity determining region (CDR) sequences selected from the group consisting of three CDRs of a heavy chain (HC) variable region selected from SEQ ID NOs: 1, 3, 5, 7, 9, 11 and 48, and three light CDRs of a light chain (LC) variable region selected from SEQ ID NOs: 2, 4, 6, 8, 10 and 12, or an analog or derivative thereof having at least 90% sequence identity with the identified antibody or fragment sequence.

In some embodiments, the anti-TNFR2 antibodies or antibody fragments thereof comprise a heavy chain variable region comprising CDR1: SEQ ID NO: 13, CDR2: SEQ ID NO: 14 and CDR3: SEQ ID NO: 15; and/or a light chain variable region comprising CDR1: SEQ ID NO: 16, CDR2: SEQ ID NO: 17, and CDR3: SEQ ID NO: 18.

In some embodiments, the anti-TNFR2 antibodies or antibody fragments thereof comprise a heavy chain variable region comprising CDR1: SEQ ID NO: 19, CDR2: SEQ ID NO: 20, and CDR3: SEQ ID NO: 21, and/or a light chain variable region comprising CDR1: SEQ ID NO: 22, CDR2: SEQ ID NO: 23, and CDR3: SEQ ID NO: 24.

In some embodiments, the anti-TNFR2 antibodies or antibody fragments thereof comprise a heavy chain variable region comprising CDR1: SEQ ID NO: 25, CDR2: SEQ ID NO: 26, and CDR3: SEQ ID NO: 27; and/or a light chain variable region comprising CDR1: SEQ ID NO: 28, CDR2: SEQ ID NO: 29, and CDR3: SEQ ID NO: 30.

In some embodiments, the anti-TNFR2 antibodies or antibody fragments thereof comprise a heavy chain variable region comprising CDR1: SEQ ID NO: 31, CDR2: SEQ ID NO: 32, and CDR3: SEQ ID NO: 33; and/or a light chain variable region comprising CDR1: SEQ ID NO: 34, CDR2: SEQ ID NO: 35, and CDR3: SEQ ID NO: 36.

In some embodiments, the anti-TNFR2 antibodies or antibody fragments thereof comprise a heavy chain variable region comprising CDR1: SEQ ID NO:37, CDR2: SEQ ID NO: 38, and CDR3: SEQ ID NO: 39; and/or a light chain variable region comprising CDR1: SEQ ID NO: 34, CDR2: SEQ ID NO: 40, and CDR3: SEQ ID NO: 41.

In some embodiments, the anti-TNFR2 antibodies or antibody fragments thereof comprise a heavy chain variable region comprising CDR1: SEQ ID NO:37, CDR2: SEQ ID NO: 49, and CDR3: SEQ ID NO: 39; and/or a light chain variable region comprising CDR1: SEQ ID NO: 34, CDR2: SEQ ID NO: 40, and CDR3: SEQ ID NO: 41.

In some embodiments, the anti-TNFR2 antibodies or antibody fragments thereof comprise a heavy chain variable region comprising CDR1: SEQ ID NO: 42, CDR2: SEQ ID NO: 43, and CDR3: SEQ ID NO: 44; and/or a light chain variable region comprising CDR1: SEQ ID NO: 45, CDR2: SEQ ID NO: 46, and CDR3: SEQ ID NO: 47.

In some embodiments, the anti-TNFR2 antibodies or antibody fragments thereof comprise a variable heavy chain sequence selected from the group consisting of SEQ ID NOs: 1, 3, 5, 7, 9, 11, and 48.

In other embodiments, the anti-TNFR2 antibodies or antibody fragments thereof comprise a variable light chain sequence selected from the group consisting of SEQ ID NOs: 2, 4, 6, 8, 10, and 12.

In other embodiments, the anti-TNFR2 antibodies or antibody fragments thereof comprise a variable heavy chain sequence selected from the group consisting of SEQ ID NOs: 1, 3, 5, 7, 9, 11 and 48 and a variable light chain sequence selected from the group consisting of SEQ ID NOs: 2, 4, 6, 8, 10 and 12.

In some embodiments, the anti-TNFR2 antibodies or antibody fragment comprises a variable heavy chain sequence and a variable light chain sequence, selected from the following combinations:

(a) a variable heavy chain sequence comprising SEQ ID NO: 1 and a variable light chain sequence comprising SEQ ID NO: 2;

(b) a variable heavy chain sequence comprising SEQ ID NO: 3 and a variable light chain sequence comprising SEQ ID NO: 4;

(c) a variable heavy chain sequence comprising SEQ ID NO: 5 and a variable light chain sequence comprising SEQ ID NO: 6;

(d) a variable heavy chain sequence comprising SEQ ID NO: 7 and a variable light chain sequence comprising SEQ ID NO: 8;

(e) a variable heavy chain sequence comprising SEQ ID NO: 9 and a variable light chain sequence comprising SEQ ID NO: 10;

(f) a variable heavy chain sequence comprising SEQ ID NO: 48 and a variable light chain sequence comprising SEQ ID NO: 10; and (g) a variable heavy chain sequence comprising SEQ ID NO: 11 and a variable light chain sequence comprising SEQ ID NO: 12.

In some embodiments, an anti-TNFR2 antibody is provided, wherein the antibody comprises (a) a heavy chain variable region comprising CDR1: SEQ ID NO: 13, CDR2: SEQ ID NO: 14, and CDR3: SEQ ID NO: 15; and/or a light chain variable region comprising CDR1: SEQ ID NO. 16, CDR2: SEQ ID NO. 17, and CDR3: SEQ ID NO: 18; (b) a heavy chain variable region comprising CDR1: SEQ ID NO: 19, CDR2: SEQ ID NO: 20, and CDR3: SEQ ID NO: 21; and/or a light chain variable region comprising CDR1: SEQ ID NO. 22, CDR2: SEQ ID NO. 23, and CDR3: SEQ ID NO: 24, (c) a heavy chain variable region comprising CDR1: SEQ ID NO: 25, CDR2: SEQ ID NO: 26, and CDR3: SEQ ID NO: 27; and/or a light chain variable region comprising CDR1: SEQ ID NO: 28, CDR2: SEQ ID NO: 29, and CDR3: SEQ ID NO: 30; (d) a heavy chain variable region comprising CDR1: SEQ ID NO: 31, CDR2: SEQ ID NO: 32, and CDR3: SEQ ID NO: 33; and/or a light chain variable region comprising CDR1: SEQ ID NO: 34, CDR2: SEQ ID NO: 35, and CDR3: SEQ ID NO: 36; (e) a heavy chain variable region comprising CDR1: SEQ ID NO: 37, CDR2: SEQ ID NO: 38, and CDR3: SEQ ID NO: 39; and/or a light chain variable region comprising CDR1: SEQ ID NO: 34, CDR2: SEQ ID NO: 40, and CDR3: SEQ ID NO: 41; (f) a heavy chain variable region comprising CDR1: SEQ ID NO: 37, CDR2: SEQ ID NO: 49, and CDR3: SEQ ID NO: 39; and/or a light chain variable region comprising CDR1: SEQ ID NO: 34, CDR2: SEQ ID NO: 40, and CDR3: SEQ ID NO: 41; or (g) a heavy chain variable region comprising CDR1: SEQ ID NO: 42, CDR2: SEQ ID NO: 43, and CDR3: SEQ ID NO: 44; and/or a light chain variable region comprising CDR1: SEQ ID NO: 45, CDR2: SEQ ID NO: 46, and CDR3: SEQ ID NO: 47.

In some embodiments, the anti-TNFR2 antibodies and antibody fragments thereof comprise one or more heavy chain variable region CDRs disclosed in Table 1 and/or one or more light chain variable region CDRs disclosed in Table 2.

In some embodiments, the anti-TNFR2 antibodies or antibody fragments thereof exhibit one or more of the following structural and functional characteristics, alone or in combination: (a) is specific for human TNFR2 (b) does not bind to human TNFR1, (c) binds to an epitope in the CRD3 or CRD4 region of the N-terminal cysteine-rich domain of TNFR2, (d) cross-reacts with cynomolgus TNFR2 (e) disrupts the human TNF binding interaction, (f) inhibits the soluble TNFα-stimulated T cell activation in the absence of binding to an Fc receptor, (g) inhibits the transmembrane TNF-stimulated T cell activation in the absence of binding to an Fc receptor, (h) enhances agonistic activity in chronically stimulated human effector T cells when binding to an Fc receptor, (i) demonstrates anti-tumor efficacy in a human TNFR2 knock-in MC38 syngeneic tumor model, (j) enhances the tumor growth inhibition of anti-PD-L1 treatment in a human TNFR2 knock-in MC38 tumor model, (k) enhances the efficacy of anti-PD-L1 treatment in a human TNFR2 Knock-in PD1 resistant B16F10 melanoma model, or demonstrates ADCC activity to contribute to anti-tumor activity, or (m) enhances the CD8 to Treg ratio within tumors.

In some embodiments, the anti-TNFR2 antibodies specifically bind to human cells expressing endogenous levels of TNFR2 and to host cells engineered to overexpress TNFR2, and do not demonstrate binding to cells expressing human TNFR1. The anti-TNFR2 antibodies or antibody fragments disclosed herein bind to cells overexpressing human or cyno TNFR2 with subnanomolar $EC_{50}$ values.

In some embodiments, the anti-TNFR2 antibodies or antibody fragments bind to an epitope in the CRD3 or CRD4 region of the N-terminal cysteine-rich domain of TNFR2. In alternative embodiments, the anti-TNFR2 antibodies and antibody fragments thereof bind to an epitope in the CRD1 or CRD2 region.

In some embodiments, the anti-TNFR2 antibodies or antibody fragments cross-react with cynomolgus monkey TNFR2 (cynoTNFR2).

In some embodiments, the anti-TNFR2 antibodies and antibody fragments thereof block the human TNF/TNFR2 binding interaction. In alternative embodiments, the anti-TNFR2 antibodies and antibody fragments thereof do not block the human TNF/TNFR2 binding interaction but antagonize the activity of soluble TNF and the membrane TNF.

In some embodiments, the anti-TNFR2 antibodies and antibody fragments thereof inhibit both the soluble TNFα- and the membrane TNFα-stimulated response of human cells expressing TNFR2.

In some embodiments, the anti-TNFR2 antibodies and antibody fragments thereof comprise a Fc region that is engineered to increase multivalent cross-linking activity with FcγRs, which will enhance the Fc-dependent agonist activity of T cells.

In some embodiments, the anti-TNFR2 antibodies enhance cytokine secretion by exhausted human effector T cells.

In some embodiments, the anti-TNFR2 antibodies demonstrate anti-tumor efficacy in a human TNFR2 knock-in MC38 syngeneic murine tumor model.

In some embodiments, the anti-TNFR2 antibodies enhance the tumor growth inhibition of anti-PD-L1 treatment in a human TNFR2 knock-in MC38 tumor model.

In some embodiments, the anti-TNFR2 antibodies enhance the efficacy of anti-PD-L1 treatment in a human TNFR2 Knock-in PD1 resistant B16F10 melanoma model.

In some embodiments, the anti-tumor efficacy of the disclosed anti-TNFR2 antibodies can be achieved by ADCC-mediated depletion of T regulatory cells from the tumor microenvironment.

In some embodiments, the anti-tumor efficacy of the disclosed anti-TNFR2 antibodies can be achieved by enhancing the CD8 to Treg ratio in the tumor microenvironment.

The present disclosure also provides isolated nucleotide sequences encoding at least one of the above antibody molecules.

The present disclosure also provides plasmids comprising at least one of the above nucleotide sequences.

The present disclosure also provides cells comprising one of the above nucleotide sequences, or one of the above plasmids.

The present disclosure also provides pharmaceutical compositions comprising or consisting of at least one of the antibodies or fragments thereof disclosed herein, and optionally a pharmaceutically acceptable diluent, carrier, vehicle and/or excipient. Such a pharmaceutical composition may be used for the antibody-based immunotherapy of cancer.

The present disclosure also relates to methods for treatment of cancer in a patient comprising administering to the patient a therapeutically effective amount of at least one of the disclosed anti-TNFR2 antibodies or fragments thereof, alone or in combination with another therapeutic agent.

BRIEF DESCRIPTION OF THE OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIGS. 1A-1E provide the amino acid sequences of the VH and VL domains of the human anti-TNFR2 antibodies and their respective CDR sequences (Kabat numbering). Sequence identifiers are provided and the CDRs are underlined in the variable domain sequences.

FIGS. 2A-2B show the binding activity of TNFR2 antibodies in the human TNFR2-expressing HEK293T by flow cytometry (A) and an image binding assay (B).

FIG. 3A shows the cross-blocking activities of the six representative clones of TNFR2 antibodies, and FIG. 3B shows the binning clusters of cross-blocking results.

Figure 7:
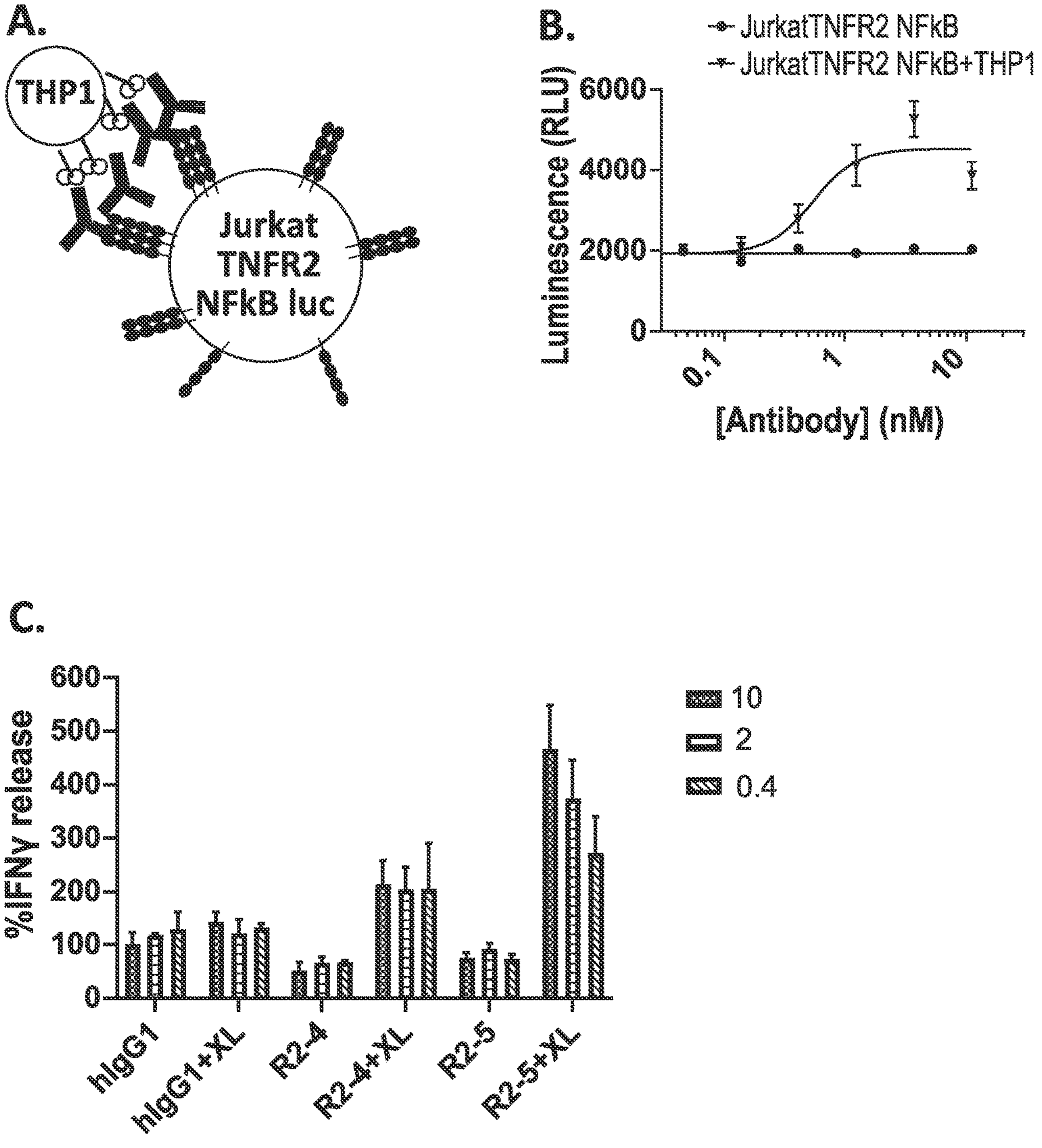

FIGS. 7A-7C show the effect of cross-linking of anti-TNFR2 antibody on Jurkat T cell signaling. FIG. 7A shows a schematic diagram of the Jukat-TNFR2 reporter assay, 7B shows the effect on Jurkat NFκB activation when co-cultured with THP-1 cells. 7C shows the level of secreted IFNγ from CD8 T cells co-cultured with T regulatory cells upon treatment with TNFR2 antibodies or a control. The legend indicates the concentration of test antibodies in μg/mL FIGS. 8A-8D show the cellular proliferation (A), IFNγ (B), TNF (C), and Granzyme (D) in in vitro generated exhausted CD8 T cells upon treatment with TNFR2 antibodies or a control. Where indicated on the graphs, the treatment includes a soluble $F(ab')_2$ crosslinker together with the antibody.

Figure 9:
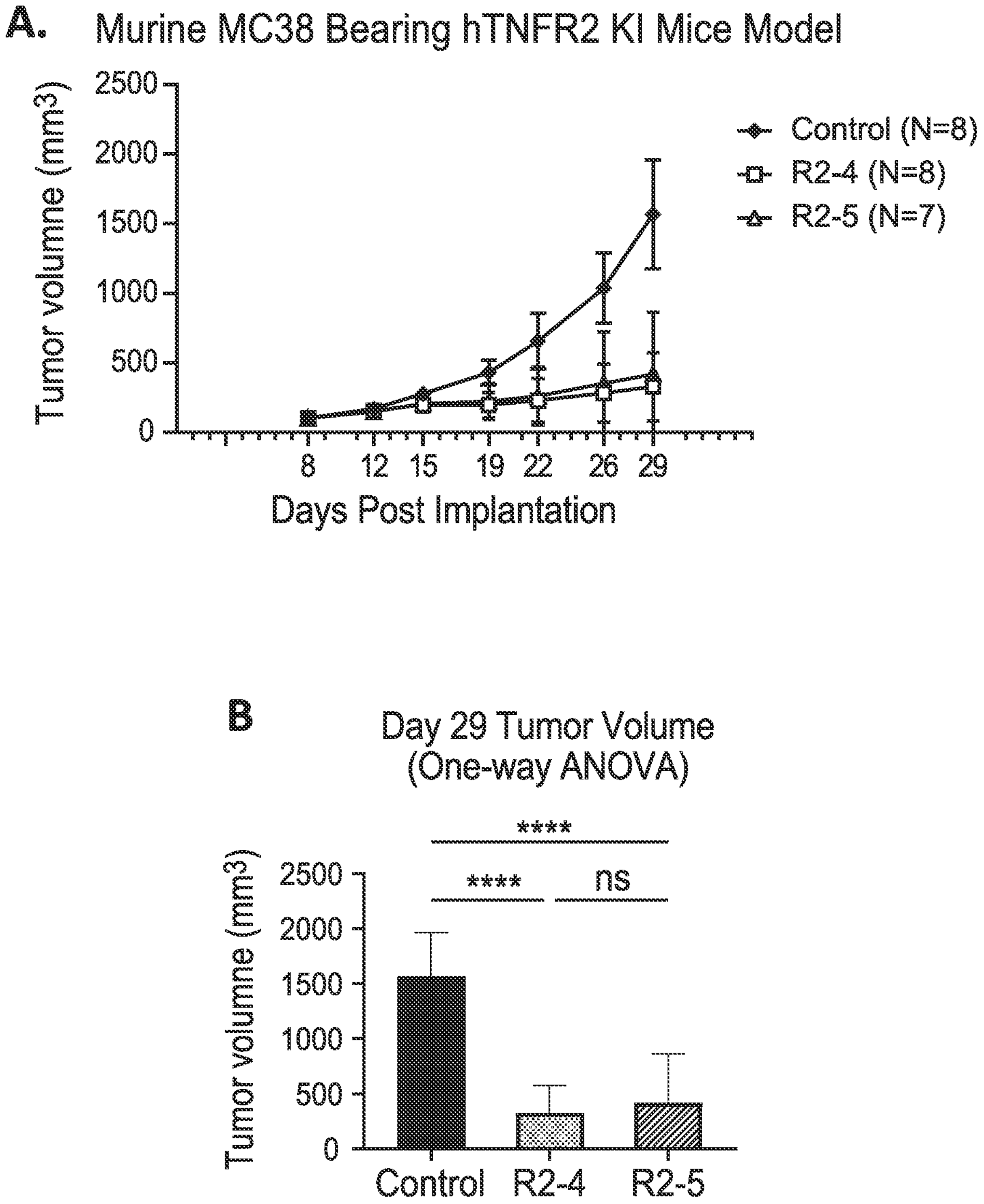

FIGS. 9A and 9B show the tumor growth in MC38 tumor-bearing hTNFR2 Knock-in mice upon treatment with TNFR2 antibodies or an isotype control antibody. FIG. 9 (A) shows the tumor growth curves. FIG. 9 (B) provides the one-way ANOVA analysis of the different treatment groups' tumor sizes.

FIGS. 10A and 10B show the survival of mice bearing MC38 tumor-bearing in the hTNFR2 Knock-in model upon treatment with anti-mPD-L1 and/or anti-TNFR2 antibodies as single agents or in combination, or a vehicle control. FIG. 10 (A) shows the tumor growth curves. FIG. 10 (B) shows the survival benefits.

Figure 11:
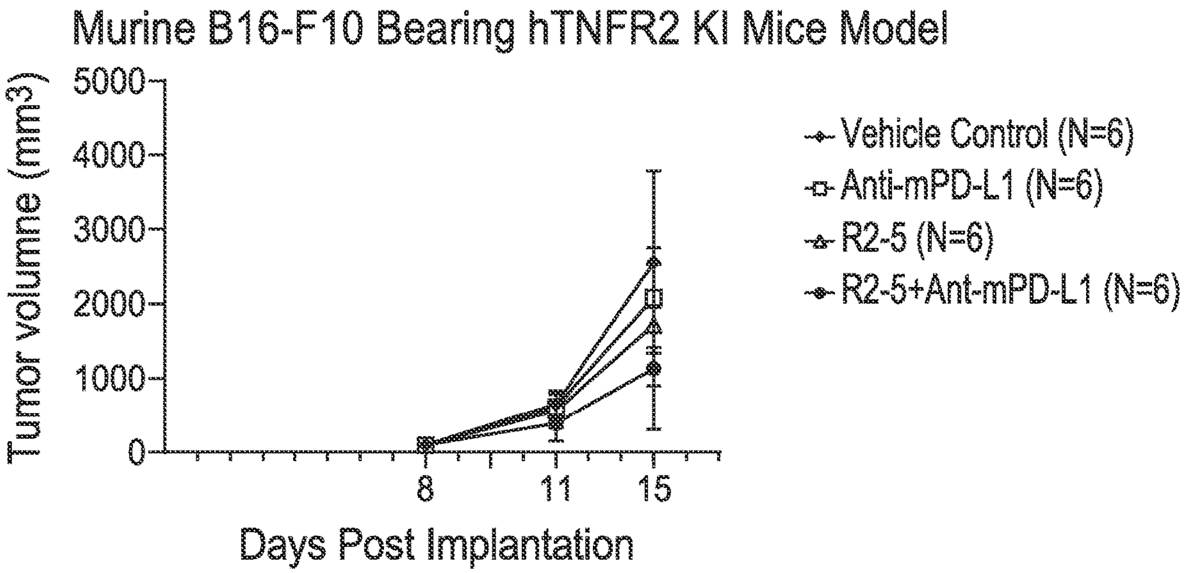
Figure 12:
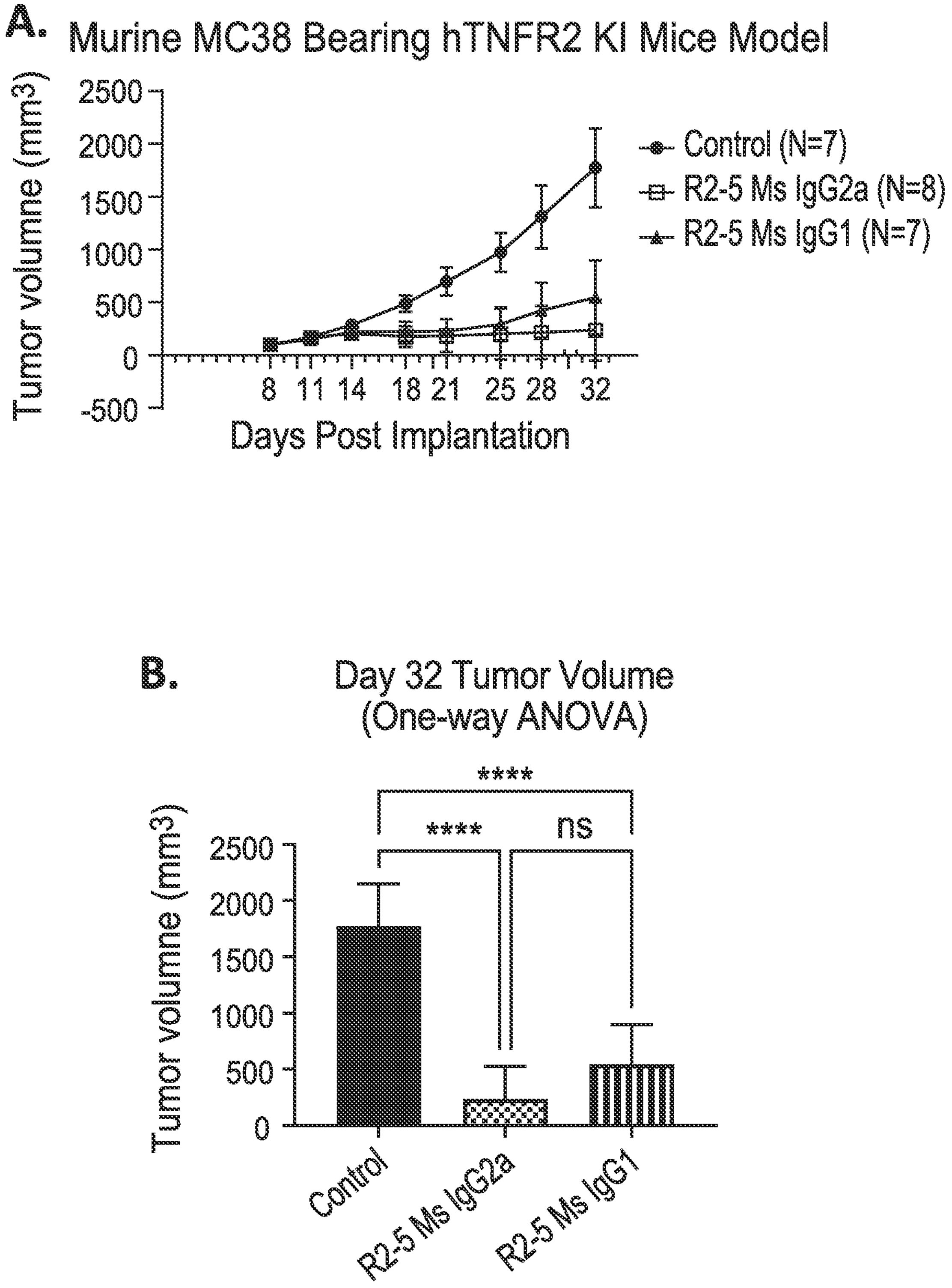
Figure 13:
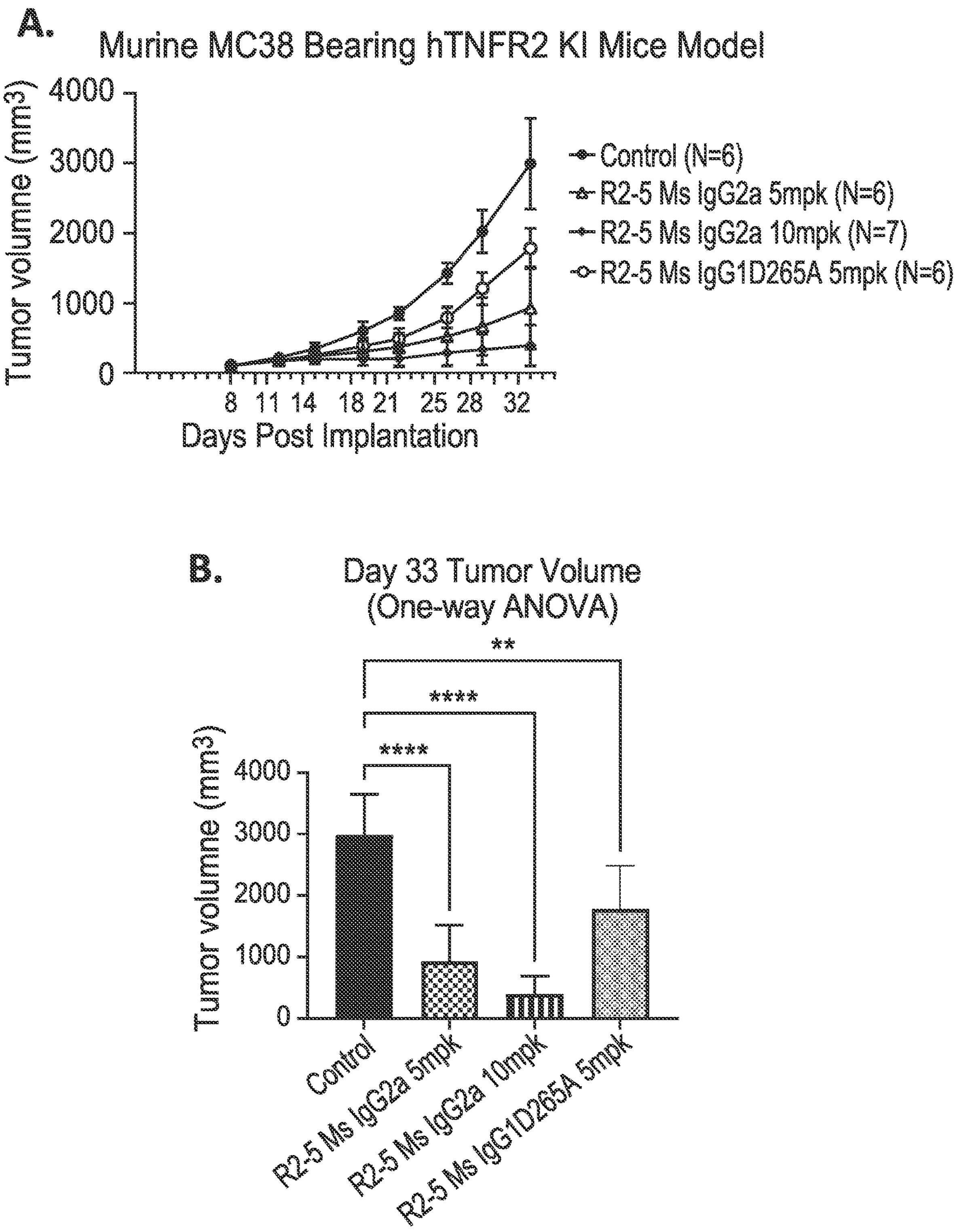

FIG. 11 shows the tumor growth inhibition of mice bearing B16-F10 tumor-bearing in the hTNFR2 Knock-in upon treatment with anti-mPD-L1 and/or anti-TNFR2 antibodies as single agents or in combination, or a vehicle control FIGS. 12A and 12B show the tumor growth in MC38 tumor-bearing hTNFR2 Knock-in mice upon treatment with TNFR2 antibodies in two different isotypes, or vehicle control. FIG. 12 (A) shows the tumor growth curves. FIG. 12 (B) provides the one-way ANOVA analysis of the different treatment groups' tumor sizes FIGS. 13A and 13B show the tumor growth in MC38 tumor-bearing hTNFR2 Knock-in mice upon treatment with TNFR2 antibodies with two different mouse IgG variants. FIG. 13 (A) shows the tumor growth curves and FIG. 13 (B) demonstrates the one-way ANOVA analysis results.

DETAILED DESCRIPTION

So that the disclosure may be more readily understood, certain technical and scientific terms are specifically defined below. Unless specifically defined elsewhere in this document, all other technical and scientific terms used herein have the meaning commonly understood by one of ordinary skill in the art to which this disclosure belongs.

Throughout this disclosure the following abbreviations will be used:

mAb or Mab or MAb—Monoclonal antibody.

CDR—Complementarity determining region in the immunoglobulin variable regions.

VH or VH—Immunoglobulin heavy chain variable region.

VL or VL—Immunoglobulin light chain variable region.

FR—Antibody framework region, the immunoglobulin variable regions excluding the CDR regions The term "tumor necrosis factor receptor superfamily" (TNFR) refers to a group of type I transmembrane proteins with a carboxy-terminal intracellular domain and an amino-terminal extracellular domain characterized by a common cysteine-rich domain (CRD). The TNFR superfamily includes receptors that mediate cellular signaling as a consequence of binding to one or more ligands in the TNF superfamily. The TNFR superfamily can be divided into three subgroups: (i) death receptors (DRs) that contain a death domain (DD) in the intracellular portion and activate apoptosis via a DD-binding partner (e.g., Fas-associated death domain (FADD) or TNFR1-associated death domain (TRADD)); (ii) TNFR-associated factor (TRAF)-interacting receptors that interact with members of the TRAF family; and, (iii) decoy receptors (DcRs) lacking a cytosolic domain.

The term "TNFR2," "TNFR2 receptor," or "TNFR2 protein" includes human TNFR2, in particular the native-sequence polypeptide, isoforms, chimeric polypeptides, all homologs, fragments, and precursors of human TNFR2. The amino acid sequences for human, cynomolgus and murine TNFR2 are provided in NCBI Reference Sequences: NP_001057.1 (human) (SEQ ID NO: 52); XP_005544817.1 (cynomolgus monkey) (SEQ ID NO: 53); NP_035740.2 (mouse)(SEQ ID NO: 54). Orthologs of TNFR2 in cynomolgus monkey and mouse share 95% and 77% sequence identity to the human protein, respectively.

The term "TNFR1," "TNFR1 receptor," or "TNFR1 protein" includes human TNFR1, in particular the native-sequence polypeptide, isoforms, chimeric polypeptides, all homologs, fragments, and precursors of human TNFR1. The amino acid sequences for human TNFR1 is provided in NCBI Reference Sequences: NP_001056.1 (human) (SEQ ID NO: 55). Human TNFR1 and TNFR2 share 18% sequence identity.

The terms "TNF," and "TNF-α" refer to the native TNF polypeptide provided in NCBI Reference Sequence NP_000585.2 (human) (SEQ ID NO: 56). Tumor necrosis factor-α exists in two biologically active forms, membrane bound TNF (tmTNF-α) (SEQ ID NO: 57) and soluble TNF-α (sTNF-α). Transmembrane TNF (tmTNF-α) is the primary ligand for TNFR2. 100721 As used herein, the terms "tumor necrosis factor receptor 2 signaling," "TNFR2 signaling," "TNFR2 signal transduction" and the like, are used interchangeably and refer to the cellular events that normally occur upon activation of TNFR2 on the surface of a TNFR2+ cell (such as T-reg cell, MDSC, or $TNFR2^+$ cancer cell), by an endogenous TNFR2 ligand, such as TNFα. TNFR2 signaling may be evidenced by a finding that expression is increased for one or more genes selected from the group consisting of NFκB, STAT5, CHUK, NKFBIE, NKFBIA, MAP3K111, TRAF2, TRAF3, RelB, cIAP2 (Torrey et al. *Sci. Signal.,* 10; 462, 2017, Yang et al., *Front Immunol,* 9, 2018). Alternatively, TNFR signaling can be demonstrated by a finding that expression of a cytokine, such as TNF, IL-1p, IL-2, IL-6 and IFNγ (Holbrook et al., F1000Res, January 28:8, 2019).

The term "antibody" herein is used in the broadest sense and encompasses various antibody structures, including but not limited to monoclonal antibodies, polyclonal antibodies, and multispecific antibodies (e.g., bispecific antibodies).

As used herein, the terms "antagonistic anti-TNFR2 antibody" and "antagonistic TNFR2 antibody" refer to TNFR2-specific antibodies that are capable of inhibiting or reducing activation of TNFR2 in the absence of binding to an Fc receptor, attenuating one or more signal transduction pathways mediated by TNFR2, and/or reducing or inhibiting at least one activity mediated by activation of TNFR2. For example, antagonistic TNFR2 antibodies may inhibit or reduce the growth and proliferation of regulatory T cells. Antagonistic TNFR2 antibodies may inhibit or reduce TNFR2 activation by blocking TNFR2 from binding TNFα.

The term "agonistic anti-TNFR2 antibody" and "agonistic TNFR2 antibody" refer to TNFR2-specific antibodies that are capable of activating of one or more signal transduction pathways mediated by TNFR2 in the absence of binding to an Fc receptor. For example, agonist TNFR2 antibodies may activate the AKT or NFKB signaling pathway, leading to a pro-proliferation or pro-survival of target cells. An agonistic anti-TNR2 antibody may also enhance T effector cell functions such as increasing the release of IFNγ, Granzyme B, TNF or IL-2.

As used herein, the term "blocking" refers to the ability of an anti-TNFR2 antibody to block the binding of TNF, either in soluble form or membrane form.

As used herein, the terms "anti-tumor necrosis factor receptor 2 antibody," "anti-TNFR2 antibody," "anti-TNFR2 antibody portion," and/or "anti-TNFR2 antibody fragment" and the like include any protein or peptide-containing molecule that includes at least a portion of an immunoglobulin molecule, such as, but not limited, to at least one complementarity determining region (CDR) of a heavy or light chain or a ligand-binding portion thereof, a heavy chain or light chain variable region, a heavy chain or light chain constant region, or any portion thereof, that is capable of specifically binding to TNFR2.

The terms "monoclonal antibody" or "mAb" as used herein refers to an antibody obtained from a population of substantially homogeneous antibodies, e.g., the individual antibodies comprising the population are identical and/or bind the same epitope, except for possible variant antibodies, e.g., containing naturally occurring mutations or arising during production and/or storage of a monoclonal antibody preparation. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric antibody" refers to a recombinant antibody in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. In addition, complementarity determining region (CDR) grafting may be performed to alter certain properties of the antibody molecule including affinity or specificity. Typically, the variable domains are obtained from an antibody from an experimental animal (the "parental antibody"), such as a rodent, and the constant domain sequences are obtained from human antibodies, so that the resulting chimeric antibody can direct effector functions in a human subject and will be less likely to elicit an adverse immune response than the parental (e.g., mouse) antibody from which it is derived.

The term "humanized antibody" refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies and will also be aware of suitable techniques for their generation. See for example, Hwang, W. Y. K., et al., *Methods* 36:35, 2005; Queen et al., *Proc. Natl. Acad. Sci. USA,* 86:10029-10033, 1989; Jones et al., *Nature,* 321:522-25, 1986; Riechmann et al., *Nature,* 332:323-27, 1988; Verhoeyen et al., *Science,* 239:1534-36, 1988; Orlandi et al., *Proc. Natl. Acad. Sci. USA,* 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety.

A "human antibody" is an antibody that possesses an amino-acid sequence corresponding to that of an antibody produced by a human and/or has been made using any of the techniques for making human antibodies known to one of skill in the art. This definition of a human antibody specifically excludes a humanized antibody comprising non-human antigen-binding residues. Human antibodies can be produced using various techniques known in the art, including methods described in Cole et al, *Monoclonal Antibodies and Cancer Therapy*, Alan R. Liss, p. 77 (1985); Boerner et al, *J. Immunol,* 147(I):86-95 (1991). See also van Dijk and van de Winkel, *Curr. Opin. Pharmacol,* 5: 368-74 (2001). Human antibodies can be prepared by administering the target antigen to a transgenic animal that has been modified to produce such antibodies in response to antigenic challenge, but whose endogenous loci have been disabled, e.g., immunized HuMab mice (see, e.g., Nils Lonberg et al., 1994, *Nature* 368:856-859, WO 98/24884, WO 94/25585, WO 93/1227, WO 92/22645, WO 92/03918 and WO 01/09187 regarding HuMab mice), xenomice (see, e.g., U.S. Pat. Nos. 6,075,181 and 6,150,584 regarding XENOMOUSE™ technology) or Trianni mice (see, e.g., WO 2013/063391, WO 2017/035252 and WO 2017/136734).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) *Nature* 341: 544-546), which consist of a VH domain; (vi) isolated complementarity determining regions (CDR), and (vii) combinations of two or more isolated CDRs which may optionally be joined by a synthetic linker.

The "variable domain" (V domain) of an antibody mediates binding and confers antigen specificity of a particular antibody. However, the variability is not evenly distributed across the 110-amino acid span of the variable domains. Instead, the V regions consist of relatively invariant stretches called framework regions (FRs) of 15-30 amino acids separated by shorter regions of extreme variability referred to herein as "hypervariable regions" or CDRs that are each 9-12 amino acids long. As will be appreciated by those in the art, the exact numbering and placement of the CDRs can be different among different numbering systems. However, it should be understood that the disclosure of a variable heavy and/or variable light sequence includes the disclosure of the associated CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

"Complementarity determining region" or "CDR" as the terms are used herein refer to short polypeptide sequences within the variable region of both heavy and light chain polypeptides that are primarily responsible for mediating specific antigen recognition. There are three CDRs (termed CDR1, CDR2, and CDR3) within each VL and each VH. Unless stated otherwise herein, CDR and framework regions are annotated according to the Kabat numbering scheme (Kabat E. A., et al., 1991, Sequences of proteins of Immunological interest, In: NIH Publication No. 91-3242, US Department of Health and Human Services, Bethesda, Md).

In other embodiments, the CDRs of an antibody can be determined according to MacCallum R M et al, (1996) *J Mol Biol* 262: 732-745, herein incorporated by reference in its entirety or according to the IMGT numbering system as described in Lefranc M-P, (1999) *The Immunologist* 7: 132-136 and Lefranc M-P et al, (1999) *Nucleic Acids Res* 27: 209-212, each of which is herein incorporated by reference in its entirety. See also, e.g. Martin A. "Protein Sequence and Structure Analysis of Antibody Variable Domains," in Antibody Engineering, Kontermann and Diibel, eds., Chapter 31, pp. 422-439, Springer-Verlag, Berlin (2001), herein incorporated by reference in its entirety. In other embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

"Framework" or "framework region" or "FR" refers to variable domain residues other than hypervariable region (HVR) residues. The FR of a variable domain generally consists of four FR domains: FR1, FR2, FR3, and FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), Vols. 1-3. In one embodiment, for the VL, the subgroup is subgroup kappa I as in Kabat et al., supra. In one embodiment, for the VH, the subgroup is subgroup Ill as in Kabat et al., supra.

The "hinge region" is generally defined as stretching from 216-238 (EU numbering) or 226-251 (Kabat numbering) of human IgG1. The hinge can be further divided into three distinct regions, the upper, middle (e.g., core), and lower hinge.

The terms "Fc region" and "constant region" are used herein to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, the numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md. (1991).

As used herein, the term "non-native constant region" refers to an antibody constant region that is derived from a source that is different from the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region), or a constant region derived from another primate, (e.g., pig, goat, rabbit, hamster, cat, dog, guinea pig, member of the bovidae family (such as cattle, bison, buffalo, elk, and yaks, among others), cow, sheep, horse, or bison, among others).

The term "endogenous" describes a molecule (e.g., a polypeptide, nucleic acid or cofactor) that is found naturally in a particular organism (e.g., a human) or in a particular location within an organism (e.g., a tissue, organ, or a cell) such as TNFR super family members expressed by human cells.

The term "effector functions," deriving from the interaction of an antibody Fc region with certain Fc receptors, include but are not necessarily limited to Clq binding, complement dependent cytotoxicity (CDC), Fc receptor binding, FcγR-mediated effector functions such as ADCC and antibody dependent cell-mediated phagocytosis (ADCP), and down regulation of a cell surface receptor. Such effector functions generally require the Fc region to be combined with an antigen binding domain (e.g., an antibody variable domain).

The term "Fc receptor" or "FcR" describes an antibody receptor that binds to the Fc region of an immunoglobulin, which is involved in antigen recognition located at the membrane of certain immune cells including B lymphocytes, natural killer cells, macrophages, neutrophils, and mast cells. Fc receptors recognizing the Fc portion of IgG are called Fc gamma receptors (FcγRs). The FcγR family includes allelic variants and alternatively spliced forms of these receptors. Based on the differences in structure, function, and affinity for IgG binding, FcγRs are classified into three major groups: FcγRI, FcγRII (FcγRIIa and FcγRIIb) and FcγRIII (FcγRIIIa and FcγRIIIb). Among them, FcγRI (CD64), FcγRIIa (CD32a), and FcγRIIIa (CD16a) are activating receptors containing the signal transduction motif, immunoreceptor tyrosine-based activation motif (ITAM), in the γ subunit of FcγRI and FcγRIIIa, or in the cytoplasmic tail of FcγRIIa. After binding of antigen-antibody complexes the activatory Fcγ receptors (human: FcγRI, FcγRIIA, FcγRIIC, FcγRIIIA, FcγRIIIB and murine: FcγRI, FcγRIII, FcγRIV) trigger immune effector functions. In contrast, FcγRIIb (CD32b) is an inhibitory receptor. Cross-linking of FcγRIIb leads to the phosphorylation of the immunoreceptor tyrosine-based inhibitory motif (ITIM) and inhibitory signaling transduction (Patel et al. Front Immunol. 2019; 10: 223).

As used herein, the terms "T regulatory cell," or "Treg" refers to a cell of the immune system that have a regulatory role by suppressing/inhibiting the proliferation, activation and cytotoxic capacity of other immune cells such as CD8 positive (CD8+) effector T cells. Regulatory T cells (Tregs) are characterized by the expression of the master transcription factor forkhead box P3 (Foxp3). There are two major subsets of Treg cells, "natural" Treg (nTreg) cells that develop in the thymus, and "induced" Treg (iTreg) cells that arise in the periphery from CD4+ Foxp3− conventional T cells. Natural Tregs are characterized as expressing both the CD4 T cell co-receptor and CD25, which is a component of the IL-2 receptor. Treg are thus CD4+CD25+. Expression of the nuclear transcription factor Forkhead box P3 (FoxP3) is the defining property which determines natural Treg development and function. Treg cells exert their suppressive effects by numerous modes of action including suppression by: secretion of inhibitory cytokines (e.g., IL-10, TGFβ, IL-35), modulation of dendritic cell function/maturation, expression of immunoregulatory surface molecules (e.g., CTLA-4, LAG-3) or cytolysis (e.g., granzyme A- and or B-mediated).

As used herein, the term "myeloid-derived suppressor cell" or "MDSC" refers to a cell of the immune system that modulates the activity of a variety of effector cells and antigen-presenting cells, such as T cells, NK cells, dendritic cells, and macrophages, among others. MDSCs are a heterogeneous population of immature myeloid cells including immature precursors of macrophages, granulocytes, and dendritic cells. The population is widely regarded as Gr1+ CD11b+ cells in mice and HLA-DR−CD11b+CD33+ cells in humans. It has a remarkable ability to suppress the innate and adaptive immune response in vitro and in vivo.

As used herein, the term "proliferation" in the context of a population of cells, such as a population of TNFR2+ cells (e.g., T-regs, MDSCs, or TNFR2+ cancer cells) refers to mitotic and cytokinetic division of a cell so as to produce a plurality of cells. Cell proliferation may be evidenced, for example, by a finding that the quantity of cell (e.g., TNFR+ cells) in a sample of cells has increased over a given time period, such as over the course of one or more days. In the present disclosure, cell proliferation is considered to be "inhibited" when the rate of a population of cells, such as a population of TNFR2+ cells contacted with an antagonistic anti-TNFR2 antibody described herein, is decreased relative to the proliferation of a population of control cells, such as a population of TNFR2+ cells not contacted with the antagonistic anti-TNFR2 antibody.

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 Å the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more.

The term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab)_2$; diabodies; linear antibodies; single-chain antibody molecules (e.g., scFv). Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large $F(ab)_2$ fragment which roughly corresponds to two disulfide linked Fab fragments having divalent antigen-binding activity and is still capable of cross-linking antigen. Fab fragments differ from Fab' fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., *Nature* 341: 544-546, 1989), which consist of a VH domain; (vi) isolated complementarity determining regions (CDR), and (vii) combinations of two or more isolated CDRs which may optionally be joined by a synthetic linker.

The term "multispecific antibody" is used in the broadest sense and specifically covers an antibody comprising a heavy chain variable domain (VH) and a light chain variable domain (VL), where the VH-VL unit has polyepitopic specificity (e.g., is capable of binding to two different epitopes on one biological molecule or each epitope on a different biological molecule). Such multispecific antibodies include, but are not limited to, full-length antibodies, antibodies having two or more VL and VH domains, bispecific diabodies and triabodies. "Polyepitopic specificity" refers to the ability to specifically bind to two or more different epitopes on the same or different target(s).

"Dual specificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 μM to 0.001 μM, 3 μM to 0.001 μM, 1 μM to 0.001 μM, 0.5 μM to 0.001 μM or 0.1 μM to 0.001 μM. "Monospecific" refers to the ability to bind only one epitope. Multi-specific antibodies can have structures similar to full immunoglobulin molecules and include Fc regions, for example IgG Fc regions. Such structures can include, but are not limited to, IgG-Fv, IgG-(scFv)2, DVD-Ig, (scFv)2-(scFv)2-Fc and (scFv)2-Fc-(scFv)2. In case of IgG-(scFv)2, the scFv can be attached to either the N-terminal or the C-terminal end of either the heavy chain or the light chain.

As used herein, the term "bispecific antibodies" refers to monoclonal, often human or humanized, antibodies that have binding specificities for at least two different antigens. In the disclosure, one of the binding specificities can be directed towards TNFR2, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the term "diabodies" refers to bivalent antibodies comprising two polypeptide chains, in which each polypeptide chain includes VH and VL domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., J. Chromatogr. B 848:79-87, 2007. In a preferred embodiment, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to TNFR2 or to a TNFR2 epitope without substantially binding to any other polypeptide or polypeptide epitope.

As used herein the term "specifically binds TNFR2" refers to the ability of an antibody, or antigen-binding fragment to recognize and bind endogenous human TNFR2 as it occurs on the surface of normal or malignant cells and to recombinant cells engineered to overexpress human TNFR2 either stably or transiently.

The term "affinity," as used herein, means the strength of the binding of an antibody to an epitope. The affinity of an antibody is given by the dissociation constant Kd, defined as [Ab]×[Ag]/[Ab−Ag], where [Ab−Ag] is the molar concentration of the antibody-antigen complex, [Ab] is the molar concentration of the unbound antibody and [Ag] is the molar concentration of the unbound antigen. The affinity constant Ka is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., *Current Protocols in Immunology*, Greene Publishing Assoc. and Wiley Interscience, N.Y., (1992, 1993), and Muller, *Meth. Enzymol.* 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

An "epitope" is a term of art that indicates the site or sites of interaction between an antibody and its antigen(s). As described by (Janeway, C, Jr., P. Travers, et al. (2001). Immunobiology: the immune system in health and disease. Part II, Section 3-8. New York, Garland Publishing, Inc.): "An antibody generally recognizes only a small region on the surface of a large molecule such as a protein . . . [Certain epitopes] are likely to be composed of amino acids from different parts of the [antigen] polypeptide chain that has been brought together by protein folding. Antigenic determinants of this kind are known as conformational or discontinuous epitopes because the structure recognized is composed of segments of the protein that are discontinuous in the amino acid sequence of the antigen but are brought together in the three-dimensional structure. In contrast, an epitope composed of a single segment of polypeptide chain is termed a continuous or linear epitope" (Janeway, C. Jr., P. Travers, et al. (2001). *Immunobiology*: the immune system in health and disease. Part II, Section 3-8. New York, Garland Publishing, Inc.).

The term "Kd", as used herein, refers to the equilibrium dissociation constant, which is obtained from the ratio of kd to ka (i.e., kd/ka) and is expressed as a molar concentration (M). Kd values for antibodies can be determined using methods well established in the art. Preferred methods for determining the Kd of an antibody include biolayer interferometry (BLI) analysis, preferably using a Fortebio Octet RED device, surface plasmon resonance, preferably using a biosensor system such as a BIACORE® surface plasmon resonance system, or flow cytometry and Scatchard analysis.

"$EC_{50}$" with respect to an agent and a particular activity (e.g. binding to a cell, inhibition of enzymatic activity, activation or inhibition of an immune cell), refers to the efficient concentration of the agent which produces 50% of its maximum response or effect with respect to such activity. "$EC_{100}$" with respect to an agent and a particular activity refers to the efficient concentration of the agent which produces its substantially maximum response with respect to such activity.

The term "tumor microenvironment" refers to cancer cells that form a tumor and the population of non-cancer cells, molecules, and/or blood vessels within the tumor or that border or surround the cancer cells.

As used herein the terms "antibody-based immunotherapy" and "immunotherapies" are used to broadly refer to any form of therapy that relies on the targeting specificity of an anti-TNFR2 antibody, bispecific molecule, antigen-binding domain, or fusion protein comprising an anti-TNFR2 antibody or antibody fragments or CDRs thereof, to mediate a direct or indirect effect on a TNFR2 expressing cell. The terms are meant to encompass methods of treatment using naked antibodies, bispecific antibodies (including T cell engaging, NK cell engaging and other immune cell/effector cell engaging formats) antibody drug conjugates, cellular therapies using T cells (CAR-T) or NK cells (CAR-NK) engineered to comprise a TNFR2-specific chimeric antigen receptor and oncolytic viruses comprising a TNFR2 specific binding agent, and gene therapies by delivering the antigen binding sequences of the anti-TNFR2 antibodies and express the corresponding antibody fragments in vivo.

TNF/TNFR Superfamilies

The human tumor necrosis factor (TNF) and TNF receptor (TNFR) superfamilies (TNFSF/TNFRSF) are currently composed of 19 cytokine-like ligand molecules and 29 related receptors (Dostert et al., *Physiol. Rev.,* 99(1):115-160, 2019, Vanamee et al., *Science Signaling*, Vol. 11, Issue 511, eaao4910, 2018).

Receptors of the tumor necrosis factor (TNF) receptor superfamily (TNFRSF) are naturally activated by ligands of the TNF superfamily. The interactions between ligands and receptors are usually very specific and high affinity (Zhang, G., *Current Opinion in Structural Biology.* 14(2):154-16, 2004). Some TNFSF ligands have multiple receptors and some receptors also bind multiple ligands.

Tumor necrosis factor-α exists in two biologically active forms, transmembrane TNF-α (tmTNF-α) and soluble TNF-α (sTNF-α). Soluble TNF-α binds with high affinity to both TNFR1 and TNFR2 but signals almost exclusively through TNFR1. Transmembrane TNF (tmTNF-α) is the primary ligand for TNFR2 and is the only form that effectively activates TNFR2 (Grell et al., *Cell,* 83:793-8021995).

Cytokines are assigned to the TNF superfamily (TNFSF) based on a conserved carboxy-terminal homology domain called the TNF homology domain (THD) (Wajant H., *Cell Death Differ.,* 22(11):1727-1741, 2015). The THD is responsible for the trimerization of TNF ligands and their binding to a trimerized receptor complex. The THD binds to a cysteine-rich domain (CRD) in the NH2 terminus of TNFRs. TNF ligands are usually synthesized in membrane-bound form and can be cleaved by proteolysis to produce soluble ligands.

All known structures of TNFSF ligands exist as trimers (Zhang, G., *Current Opinion in Structural Biology,* 14(2):154-16, 2004), and data from structural and biochemical studies establish that higher order clustering of TNF family ligands plays an essential role in the initiation of signal transduction. The binding of the membrane-bound or soluble TNFSF ligand trimer to its corresponding receptor on a cell's surface triggers the trimerization of the receptor proteins and activation of their downstream signaling pathways (Dostert et al., *Physiol. Rev.,* 99(1):115-160, 2019).

TNF ligands are mainly expressed by the professional antigen-presenting cells (APCs) of the immune system, such as dendritic cells (DCs), macrophages and B cells, but are also produced by T cells, NK cells, mast cells, eosinophils, basophils, endothelial cells, thymic epithelial cells, and smooth muscle cells (Dostert et al., *Physiol. Rev.,* 99(1):115-160, 2019).

Members of the TNFRSF are transmembrane proteins that consist of an ectodomain, a transmembrane domain, and an intracellular domain that recruits signal transduction proteins inside the cell. The ectodomain of TNFRSF is characterized by a cysteine-rich signature comprising four repeated cysteine-rich domains (CRDs) (CRD1, CRD2, CRD3 and CRD4) but different intracellular domains.

Based on their cytosolic signaling domains, TNFRs can be generally classified into three groups: (i) death receptors (DRs) (e.g., DR3, DR6, TNFRI) that contain a death domain (DD) in the intracellular portion and activate apoptosis via a DD-binding partner (e.g., Fas-associated death domain (FADD) or TNFR1-associated death domain (TRADD)); (ii) TNFR-associated factor (TRAF)-interacting receptors (e.g., TNFRII, GITR, OX40, 41BB, CD30, LTbR, CD40 that interact with members of the TRAF family; and, (iii) decoy receptors (DcRs) lacking a cytosolic domain (e.g., TRAILR3, TRAILR4) (Vanamee et al., *Science Signaling*, Vol. 11(511), eaao4910, 2018).

TNFRs are naturally activated by ligands of the TNF superfamily which as described above, occur as soluble and transmembrane trimers. High affinity binding of their specific TNFSF ligands induces clustering of receptors expressed in the cognate target cell that in turn initiates signal transduction pathways culminating in cellular responses (Ward-Kavanagh et al., *Immunity,* 44: 1005-1019, 2016). Full and robust activation of TNFRs requires two steps. Initially, three TNFR molecules interact with a TNFSF ligand (TNFL) trimer. In a second step, two or more of these initially formed trimeric ligand receptor complexes assemble to supramolecular signaling clusters. Efficient TNFR2 signaling has been reported to require the clustering/oligomerization of multiple receptor subunits (Vanamee et al., *Science Signaling*, Vol. 11(511), eaao4910, 2018).

Two categories of TNFRs can be defined, based on their response to soluble TNFL trimers. TNFRs of category I bind soluble TNFL trimers, aggregate afterwards, and become fully and strongly activated this way. In contrast, category II TNFRs (e.g., TNFR2, 41BB, CD27, CD40, CD95, OX40 and Fn14) also interact with high-affinity with soluble TNFL trimers; but fail to cluster and signal afterwards. However, oligomerization and/or cell attachment of soluble TNFL trimers enable soluble TNFL trimers to robustly stimulate category II TNFRs (Wajant H. *Cell Death Differ.,* 22(11): 1727-1741, 2015).

The structure of the archetypical TNF/TNFR signaling complex consists of a trimeric ligand bound to three receptors (Vanamee et al., *Science Signaling*, Vol. 11, Issue 511, eaao4910, 2018 and Wajant H., *Cell Death Differ.,* 22(11): 1727-1741, 2015). Several TNFSF/TNFRSF ligand-receptor crystal structures have been resolved, including CD40-CD40L, OX40-OX40L, and TNF-TNFR2, and they all show trimerization in the ligand-receptor pair (Dostert et al., *Physiol. Rev.,* 99(1):115-160, 2019). These observations confirm that a 3:3 ratio is the common basis for TNFSF/TNFRSF signaling.

Both innate and adaptive immune cells are controlled by TNFSF/TNFRSF members in a manner that is crucial for the coordination of various cellular and molecular mechanisms driving either co-stimulation or co-inhibition of the immune response. The cellular and molecular outcomes initiated by TNFRs depend on patterns of ligand-receptor specificity, cellular TNFR expression profiles and the identity and FcγR expression profile of the immune cell types involved in the interaction.

TNFR2

Tumor Necrosis Factor Receptor 2 (TNFR2 or TNFRII), also known as TNFRSF1B and CD120b, is a co-stimulatory member of the tumor necrosis factor receptor superfamily (TNFRSF), which includes proteins such as GITR, 0X40, CD27, CD40, and 4-1BB (CD137). TNFR2 is a cell-surface receptor that is expressed on T cells and has been shown to enhance the activation of effector T (Teff) cells and decrease Treg-mediated suppression.

TNFR2 expression is mainly restricted to immune cells (e.g., CD4', CD8+, MDSC, tumor infiltrating Treg cells and NK cells in human PBMCs) and some tumor cells whereas TNFR1 shows ubiquitous expression. TNFR2 binds the cognate ligand tmTNF-α, a type II transmembrane protein, and the secreted ligand Lymphotoxin-α (LTα), both of which also bind TNFR1 (Ward-Kavanagh et al., *Immunity,* 44: 1005-1019, 2016).

TNFR2 represents a member of the TRAF-interacting TNFRSF. In the presence of TCR stimulation, TRAF-interacting receptors like TNFR2, 41BB and OX40 function as potent T-cell costimulatory molecules. TRAF-interacting receptors are expressed on activated and memory T-cells, but not on resting T-cells and their cognate ligands are predominantly expressed on activated antigen-presenting cells such as dendritic cells, macrophages, innate lymphoid cells, and many other inflammatory cell types (Dostert et al., *Physiol. Rev.,* 99(1):115-160, 2019 and Williams et al., *Oncotarget,* 7(42):68278-68291, 2016). Their immune-enhancing costimulatory properties can be targeted to boost antitumor immunity, by promoting T-cell proliferation, survival and effector functions in several types of cancers. Typically targeting strategies include the use of agonistic antibodies or recombinant soluble ligands specific for the receptor.

The activation of TNFR2 is primarily considered to trigger the pro-survival NF-κB pathway via TRAF2 and TRAF3 E3 ligases, whereas the activation of TNFR1 recruits TRADD to the cytoplasmic death domain and activates caspase-dependent pathways (Brenner et al., *Nat. Rev. Immunol.,* 15:362-374, 2015). Through the regulation of TRAF2/3 and NF-kB signaling, TNFR2 can mediate the transcription of genes that promote cell survival and proliferation. Accordingly, TNF promotes apoptosis via binding to TNFR1 but exerts pro-survival effects via TNFR2.

Several publications report that TNFR2 is expressed on and has critical roles in immune cells, including $CD4^+$ regulatory T cells (Tregs) (Govindaraj et al., *Front. Immunol.,* 4:233, 2013), $CD4^+$ effector T cells (Teffs) (Chen et al., *Sci. Rep.,* 6:32834, 2016), $CD8^+$ Tregs (Ablamunits et al., *Eur. J. Immunol.,* 40(10):2891-901, 2010), $CD8^+$ Teffs (Krummey et al., J. Immunol., 197(5):2009-15, 2016) and MDSCs (Hu et al., *J. Immunol.,* 192 (3):1320-1331, 2014). These findings demonstrate that TNFR2 is involved in various immune responses that can contribute to tumor immune evasion. Inhibition of TNFR2 might help to break tumor-associated immune tolerance by reducing Treg activity. Alternatively, agonism of TNFR2 might enhance the activity of CD8+ effector cells.

TNFR2 is preferentially expressed on the maximally immunosuppressive subset of Tregs in humans and murine Tregs. There is clear evidence that TNFR2 mediates the stimulatory activity of TNF on CD4*FoxP3 Tregs, resulting in the proliferative expansion, activation and phenotypic stability of Tregs (Chen and Oppenheim, *Sci. Signal.,* 10(462), eaal2328, 2017).

In addition, TNFR2 is aberrantly expressed on several types of tumor cells and induces tumor progression through several signal transduction cascades. TNFR2 directly promotes the proliferation of some kinds of tumor cells (Sheng et al., *Front. Immunol.,* 9: 1170 2018, and Chen and Oppenheim, *Sci. Signal.,* 10(462), eaal2328, 2017, Torrey et al, *Sci. Signal* (2017), Yang et al., *J. Leukocyte Biol.,* 107:6, 2020.)

Targeting TNF/TNFR2 for Immunotherapy

Typically, TNFRSF receptor-specific antibodies are used with the intention to activate TNFRSF receptors on tumor cells to trigger cell death (TRAILR1, TRAILR2) or to activate costimulatory receptors on immune cells to promote antitumor immunity (4-1BB, GITR, CD27, OX40 CD40) (Wajant H. *Cell. Death. Differ.,* 22(11):1727-1741, 2015). In some cases (TNFR2, CD30, Fn14), the tumor-associated expression pattern of certain TNFRSF receptors is exploited to target tumor cells with ADCC-inducing antibodies or antibody immunotoxins.

TNFR2 is preferentially highly expressed on activated T regulatory cells and has a crucial role in promoting Treg proliferative expansion, phenotypical stability and in vivo immunosuppressive functions (Chen and Oppenheim, *Sci. Signal.,* 10(462), eaal2328, 2017). Furthermore, the survival and growth of some tumor cells that express TNFR2 is promoted by ligands of TNFR2. In addition, TNFR2 antagonists created by Torrey et al. have the capacity to induce the death of OVCAR3, an ovarian cancer cell line with surface expression of TNFR2 (Torrey et al., *Sci. Signal.,* 10:462, 2017). Thus, the rationale for targeting TNFR2 in the treatment of tumors is two-fold: inhibitors of TNFR2 boost antitumor responses by inhibiting the activities of, or eliminating TNFR2-expressing Tregs, and the potential for directly killing TNFR2-expressing tumor cells.

Tumor-infiltrating Treg cells are potent immunosuppressive cells that represent a major cellular mechanism of tumor immune evasion and play a major role in dampening naturally occurring and therapeutically induced antitumor immune responses. Accumulation of Treg cells within tumor tissues, and the resultant high ratio of Treg cells to effector T (Teff) cells, is correlated with poor prognosis of cancer patients, including those with lung cancer (4), breast cancer (5), colorectal cancer (6), pancreatic cancer (7), and other malignancies. Elimination of Treg activity, by either reducing their number or down-regulating their immunosuppressive function using checkpoint inhibitors, has become an effective strategy to enhance the efficacy of cancer therapy.

In addition to Tregs, $CD11b^{+}Gr1^{+}$ MDSCs also contribute to tumor immune evasion in tumor bearing mice. It has recently been shown that the generation, accumulation, and function of MDSCs depend on TNF/TNFR2 signaling. MDSCs expand extensively during inflammation and tumor progression in mice and humans and can enhance tumor growth by suppressing T cell-mediated antitumor responses. Signaling of TNFR2, but not TNFR1, has been demonstrated to be crucial for MDSC accumulation (Zhao et al., J. Clin. Invest., 122(11):4094-4104, 2012). In tumor-bearing mice, MDSCs accumulate in central (bone marrow) and peripheral (spleen, blood, draining lymph nodes) organs as well as in tumor sites (Zhao et al., supra).

Anti-TNFR2 Antibodies

The disclosed anti-TNFR2 antibodies (R2_mAb-1 through R2_mAb-6 alternatively referred to herein as R2-1 through R2-6 in the figures) are specific for (e.g., specifically bind) human TNFR2. These antibodies and fragments thereof are characterized by unique sets of CDR sequences, specificity for TNFR2 and are useful in cancer immunotherapy as monotherapy or in combination with other anticancer agents. More specifically, the disclosure relates to antibodies that bind to human TNFR2, and to their use to modulate the TNF/TNFR2-mediated activity of cells localized to the tumor microenvironment.

It is recognized that both inhibition of TNFR activity and stimulation of TNFRs can elicit valuable therapeutic activities. For example, TNFR2 stimulation may provide a means to expand and activate T effector cells and to enhance their anti-tumor activities. In contrast, TNFR2-mediated inhibition or depletion of TNFR2-expressing cells (Tregs, MDSCs and tumor cells) could establish and maintain a tumor-suppressive microenvironment. Antagonistic and agonistic antibodies directed against immunostimulatory receptors belonging to the tumor necrosis factor receptor (TNFR) superfamily are emerging as promising cancer immunotherapies. However, to date there are no approved therapeutic antibodies directed against TNFR2.

We sought to discover unique TNFR2 antibodies that demonstrate novel mechanisms to overcome immunosuppressive setting and T cell exhaustion for better immunotherapy. The disclosed anti-TNFR2 antibodies may be particularly beneficial for tumor microenvironments enriched in exhausted T cells, suppressive myeloid cells, or regulatory T cells that contribute to anti-PD-1/PD-L1 resistance.

In some embodiments, the anti-TNFR2 antibodies or antibody fragments thereof exhibit one or more of the following structural and functional characteristics, alone or in combination: (a) is specific for human TNFR2 (b) does not bind to human TNFR1, (c) binds to an epitope in the CRD3 or CRD4 region of the N-terminal cysteine-rich domain of TNFR2, (d) cross-reacts with cynomolgus TNFR2 (e) disrupts the human TNF binding interaction, (f) inhibits the soluble TNFα-stimulated T cell activation in the absence of binding to an Fc receptor, (g) inhibits the transmembrane TNF-stimulated T cell activation in the absence of binding to an Fc receptor, (h) enhances agonistic activity in chronically stimulated human effector T cells when binding to an Fc receptor, (i) demonstrates anti-tumor efficacy in a human TNFR2 knock-in MC38 syngeneic tumor model, (j) enhances the tumor growth inhibition of anti-PD-L1 treatment in a human TNFR2 knock-in MC38 tumor model, (k) enhances the efficacy of anti-PD-L1 treatment in a human TNFR2 Knock-in PD1 resistant B16F10 melanoma model, or (l) demonstrates ADCC activity to contribute to anti-tumor activity, or (m) enhances the CD8 to Treg ratio within tumors.

In one embodiment, the disclosed antibodies inhibit TNFR2 signaling in the monocytic THP1 cells through Fc receptor interaction. In an alternative embodiment, Fc receptor crosslinking through the THP1 cells causes the antibody to activate Jurkat T cell TNFR2 signaling. Further, in primary CD8 T cells, they enhanced anti-CD3/CD28-stimulated IFNγ release in a crosslinking dependent manner. More particularly, crosslinked TNFR2 antibodies promote the function of CD8 T effector cells in such manner that they can overcome the suppressive effect from T regulatory cells in a co-culture setting.

In another alternative embodiment, treatment of CD8 T effector cells with an exhausted phenotype (e.g., induced by repeated CD3/CD28 stimulation), with one or more of the disclosed anti-TNFR2 antibodies restored CD8 T cell function characterized by increased cell proliferation, improved IFN-γ and granzyme release, as well as an increased level of released soluble TNFα. In contrast, treatment with anti-PD1 did not restore the function of exhausted CD8 T cells. Using a human TNFR2 knock-in MC38 mouse tumor model, two disclosed antibodies have demonstrated strong anti-tumor efficacy.

In some embodiments, it is advantageous that the disclosed anti-TNFR2 antibodies bind both to hTNFR2 and to cynomolgus monkey TNFR2 (cynoTNFR2). Cross-reactivity with TNFR2 expressed on cells in cynomolgus monkey (e.g. *Macaca fascicularis*), is advantageous because it enables animal testing of the antibody molecule without having to use a surrogate antibody. The disclosed anti-TNFR2 antibodies, R2_mAb 1 to R2_mAb 6, all bind to TNFR2 from cynomolgus monkey with notable affinity.

An exemplary antibody such as an IgG comprises two heavy chains and two light chains. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues are forming a hypervariable loop (e.g. residues 26-32 (LCDR1), 50-52 (LCDR2) and 91-96 (LCDR3) in the light chain variable region and 26-32

(HCDR1), 53-55 (HCDR2) and 96-101 (HCDR3) in the heavy chain variable region; Chothia and Lesk (1987) *J. Mol. Biol.* 196:901-917.

In an embodiment, the anti-TNFR2 antibodies or antibody fragments thereof comprise a VH having a set of CDRs (HCDR1, HCDR2, and HCDR3) disclosed in Table 1. For example, the anti-TNFR2 antibodies or antibody fragments thereof may comprise a set of CDRs corresponding to those CDRs in one or more of the anti-TNFR2 antibodies disclosed in Table 1 (e.g., the CDRs of the R2_mAb1).

In another embodiment, the anti-TNFR2 antibodies comprise a VL having a set of CDRs (LCDR1, LCDR2, and LCDR3) as disclosed in Table 2. For example, the anti-TNFR2 antibodies or antibody fragments thereof may comprise a set of CDRs corresponding to those CDRs in one or more of the anti-TNFR2 antibodies disclosed in Table 2 (e.g., the CDRs of the R2_mAb 2).

TABLE 1

CDR Sequences of Anti-TNFR2 Antibody Variable Heavy Chains

| Anti-TNFR2 Ab | CDR1 | CDR2 | CDR3 |
|---|---|---|---|
| R2_mAb-1 | SEQ ID NO: 13 | SEQ ID NO: 14 | SEQ ID NO: 15 |
| R2_mAb-2 | SEQ ID NO: 19 | SEQ ID NO: 20 | SEQ ID NO: 21 |
| R2_mAb-3 | SEQ ID NO: 25 | SEQ ID NO: 26 | SEQ ID NO: 27 |
| R2_mAb-4 | SEQ ID NO: 31 | SEQ ID NO: 32 | SEQ ID NO: 33 |
| R2_mAb-5 | SEQ ID NO: 37 | SEQ ID NO: 38 | SEQ ID NO: 39 |
| R2_mAb-5.1 | SEQ ID NO: 37 | SEQ ID NO: 49 | SEQ ID NO: 39 |
| R2_mAb-6 | SEQ ID NO: 42 | SEQ ID NO: 43 | SEQ ID NO: 44 |

TABLE 2

CDR Sequences of Anti-TNFR2 Variable Light Chains

| Anti-TNFR2 Ab | CDR1 | CDR2 | CDR3 |
|---|---|---|---|
| R2_mAb-1 | SEQ ID NO: 16 | SEQ ID NO: 17 | SEQ ID NO: 18 |
| R2_mAb-2 | SEQ ID NO: 22 | SEQ ID NO: 23 | SEQ ID NO: 24 |
| R2_mAb-3 | SEQ ID NO: 28 | SEQ ID NO: 29 | SEQ ID NO: 30 |
| R2_mAb-4 | SEQ ID NO: 34 | SEQ ID NO: 35 | SEQ ID NO: 36 |
| R2_mAb-5 | SEQ ID NO: 34 | SEQ ID NO: 40 | SEQ ID NO: 41 |
| R2_mAb-6 | SEQ ID NO: 45 | SEQ ID NO: 46 | SEQ ID NO: 47 |

In an alternative embodiment, the anti-TNFR2 antibodies or antibody fragments thereof comprise a VH having a set of CDRs (HCDR1, HCDR2, and HCDR3) as disclosed in Table 1, and a VL having a set of CDRs (LCDR1, LCDR2, and LCDR3) as disclosed in Table 2.

In an embodiment, the antibody may be a monoclonal, human, humanized or chimeric antibody, or antigen-binding portions thereof that specifically binds to human TNFR2. In one embodiment, the anti-TNFR2 antibody or antibody fragment thereof comprises all six of the CDR regions of the R2_mAb 1, R2_mAb 2, R2_mAb 3, R2_mAb 4, R2_mAb 5 or R2_mAb 6 antibodies formatted as a human antibody. In an alternative embodiment, the anti-TNFR2 antibody or antibody fragment comprises the CDR regions of R2_mAb 5.1 variable heavy chain and the CDR regions of R2_mAb 5 variable light chain.

In an embodiment, the anti-TNFR2 antibodies or antibody fragments thereof comprise a VH having a set of complementarity-determining regions (CDR1, CDR2, and CDR3) selected from the group consisting of:

(i) CDR1: SEQ ID NO: 13, CDR2: SEQ ID NO: 14, CDR3: SEQ ID NO: 15;
(ii) CDR1: SEQ ID NO: 19, CDR2: SEQ ID NO: 20, CDR3: SEQ ID NO: 21;
(iii) CDR1: SEQ ID NO: 25, CDR2: SEQ ID NO: 26, CDR3: SEQ ID NO: 27;
(iv) CDR1: SEQ ID NO: 31, CDR2: SEQ ID NO: 32, CDR3: SEQ ID NO: 33;
(v) CDR1: SEQ ID NO: 37, CDR2: SEQ ID NO: 38, CDR3: SEQ ID NO: 39;
(vi) CDR1: SEQ ID NO: 37, CDR2: SEQ ID NO: 49, CDR3: SEQ ID NO: 39; and
(vii) CDR1: SEQ ID NO: 42, CDR2: SEQ ID NO: 43, CDR3: SEQ ID NO: 44.

In an embodiment, the anti-TNFR2 antibodies or antibody fragments thereof comprise a VL having a set of complementarity-determining regions (CDR1, CDR2, and CDR3) selected from the group consisting of:

(i) CDR1: SEQ ID NO: 16, CDR2: SEQ ID NO: 171 CDR3: SEQ ID NO: 18;
(ii) CDR1: SEQ ID NO: 22, CDR2: SEQ ID NO: 23, CDR3: SEQ ID NO: 24;
(iii) CDR1: SEQ ID NO: 28, CDR2: SEQ ID NO: 29, CDR3: SEQ ID NO: 30;
(iv) CDR1: SEQ ID NO. 34, CDR2: SEQ ID NO: 35, CDR3: SEQ ID NO: 36;
(v) CDR1: SEQ ID NO: 34, CDR2: SEQ ID NO: 40, CDR3: SEQ ID NO: 41; and
(vi) CDR1: SEQ ID NO: 45, CDR2: SEQ ID NO: 46, CDR3: SEQ ID NO: 47.

In another embodiment, the anti-TNFR2 antibodies or antibody fragments thereof comprise:

(a) a VH having a set of complementarity-determining regions (CDR1, CDR2, and CDR3) selected from the group consisting of:
 (i) CDR1: SEQ ID NO: 13, CDR2: SEQ ID NO: 14, CDR3: SEQ ID NO: 15;
 (ii) CDR1: SEQ ID NO: 19, CDR2: SEQ ID NO: 20, CDR3: SEQ ID NO: 21;
 (iii) CDR1: SEQ ID NO: 25, CDR2: SEQ ID NO: 26, CDR3: SEQ ID NO: 27;
 (iv) CDR1: SEQ ID NO: 31, CDR2: SEQ ID NO: 32, CDR3: SEQ ID NO: 33;
 (v) CDR1: SEQ ID NO: 37, CDR2: SEQ ID NO: 38, CDR3: SEQ ID NO: 39;
 (vi) CDR1: SEQ ID NO: 37, CDR2: SEQ ID NO: 49, CDR3: SEQ ID NO: 39; and
 (vii) CDR1: SEQ ID NO: 42, CDR2: SEQ ID NO: 43, CDR3: SEQ ID NO: 44, and
(b) a VL having a set of complementarity-determining regions (CDR1, CDR2, and CDR3) selected from the group consisting of:
 (i) CDR1: SEQ ID NO: 16, CDR2: SEQ ID NO: 17, CDR3: SEQ ID NO: 18,
 (ii) CDR1: SEQ ID NO: 22, CDR2: SEQ ID NO: 23, CDR3: SEQ ID NO: 24;
 (iii) CDR1: SEQ ID NO: 28, CDR2: SEQ ID NO: 29, CDR3: SEQ ID NO: 30;
 (iv) CDR1: SEQ ID NO: 34, CDR2: SEQ ID NO: 35, CDR3: SEQ ID NO: 36;
 (v) CDR1: SEQ ID NO: 34, CDR2: SEQ ID NO: 40, CDR3: SEQ ID NO: 41; and
 (vi) CDR1: SEQ ID NO: 45, CDR2: SEQ ID NO: 46, CDR3: SEQ ID NO: 47.

In an embodiment, the antibodies comprise a combination of a VH and a VL having a set of complementarity-determining regions (CDR1, CDR2 and CDR3) selected from the group consisting of:

(i) VH: CDR1: SEQ ID NO: 13, CDR2: SEQ ID NO: 14, CDR3: SEQ ID NO: 15, VL: CDR1: SEQ ID NO: 16, CDR2: SEQ ID NO: 17, CDR3: SEQ ID NO: 18;

ii) VH: CDR1: SEQ ID NO: 19, CDR2: SEQ ID NO: 20, CDR3: SEQ ID NO: 21, VL: CDR1: SEQ ID NO: 22, CDR2: SEQ ID NO: 23, CDR3: SEQ ID NO: 24;

(iii) VH: CDR1: SEQ ID NO: 25, CDR2: SEQ ID NO: 26, CDR3: SEQ ID NO: 27, VL: CDR1: SEQ ID NO: 28, CDR2: SEQ ID NO: 29, CDR3: SEQ ID NO: 30;

(iv) VH: CDR1: SEQ ID NO: 31 CDR2: SEQ ID NO: 32, CDR3: SEQ ID NO: 33, VL: CDR1: SEQ ID NO: 34, CDR2: SEQ ID NO: 35, CDR3: SEQ ID NO: 36;

(v) VH: CDR1: SEQ ID NO: 37, CDR2: SEQ ID NO: 38, CDR3: SEQ ID NO: 39, VL: CDR1: SEQ ID NO: 34, CDR2: SEQ ID NO: 40, CDR3: SEQ ID NO: 41;

(vi) VH: CDR1: SEQ ID NO: 37, CDR2: SEQ ID NO: 49, CDR3: SEQ ID NO: 39, VL: CDR1: SEQ ID NO: 34, CDR2: SEQ ID NO: 40, CDR3: SEQ ID NO: 41; and (vii) VH: CDR1: SEQ ID NO: 42, CDR2: SEQ ID NO: 43, CDR3: SEQ ID NO: 44, VL: CDR1: SEQ ID NO: 45, CDR2: SEQ ID NO: 46, CDR3: SEQ ID NO: 47.

In an embodiment, the anti-TNFR2 antibodies or antibody fragments thereof comprise a variable heavy chain sequence selected from the group consisting of: SEQ ID NOs: 1, 3, 5, 7, 9, 11, and 48; and/or a variable light chain sequence selected from the group consisting of: SEQ ID NOs: 2, 4, 6, 8, 10, and 12.

In an embodiment, the anti-TNFR2 antibodies or antibody fragments thereof comprise a pair of variable heavy chain and variable light chain sequences, selected from the following combinations: a variable heavy chain sequence comprising SEQ ID NO: 1 and a variable light chain sequence comprising SEQ ID NO: 2; a variable heavy chain sequence comprising SEQ ID NO: 3 and a variable light chain sequence comprising SEQ ID NO: 4: a variable heavy chain sequence comprising SEQ ID NO: 5 and a variable light chain sequence comprising SEQ ID NO: 6; a variable heavy chain sequence comprising SEQ ID NO: 7 and a variable light chain sequence comprising SEQ ID NO: 8; a variable heavy chain sequence comprising SEQ ID NO: 9 and a variable light chain sequence comprising SEQ ID NO: 10; a variable heavy chain sequence comprising SEQ ID NO: 48 and a variable light chain sequence comprising SEQ ID NO: 10; a variable heavy chain sequence comprising SEQ ID NO: 11 and a variable light chain sequence comprising SEQ ID NO: 12. The skilled person will further understand that the variable light and variable heavy chains may be independently selected, or mixed and matched, to prepare an anti-TNFR2 antibody comprising a combination of variable heavy and variable light chain that is distinct from the pairings identified above.

In an alternative embodiment, the anti-TNFR2 antibodies or antibody fragments thereof comprise a pair of variable heavy chain and variable light chain sequences, selected from the following combinations: a variable heavy chain sequence that is 90%, 95%, or 99% identical to SEQ ID NO: 1 and a variable light chain sequence that is 90%, 95%, or 99% identical to SEQ ID NO: 2; a variable heavy chain sequence that is 90%, 95%, or 99% identical to SEQ ID NO: 3 and a variable light chain sequence that is 90%, 95%, or 99% identical to SEQ ID NO: 4; a variable heavy chain sequence that is 90%, 95%, or 99% identical to SEQ ID NO: 5 and a variable light chain sequence that is 90%, 95%, or 99% identical to SEQ ID NO: 6; a variable heavy chain sequence that is 90%, 95%, or 99% identical to SEQ ID NO: 7 and a variable light chain sequence that is 90%, 95%, or 99% identical to SEQ ID NO: 8; a variable heavy chain sequence that is 90%, 95%, or 99% identical to SEQ ID NO: 9 and a variable light chain sequence that is 90%, 95%, or 99%/identical to SEQ ID NO: 10; a variable heavy chain sequence that is 90%, 95%, or 99% identical to SEQ ID NO: 11 and a variable light chain sequence that is 90%, 95%, or 99% identical to SEQ ID NO: 12. The skilled person will further understand that the variable light and variable heavy chains may be independently selected, or mixed and matched, to prepare an anti-TNFR2 antibody comprising a combination of variable heavy and variable light chain that is distinct from the pairings identified above. Thus, in one embodiment, the antibody fragment comprises at least one CDR as described herein. The antibody fragment may comprise at least two, three, four, five, or six CDRs as described herein. The antibody fragment further may comprise at least one variable region domain of an antibody described herein. The variable region domain may be of any size or amino acid composition and will generally comprise at least one CDR sequence responsible for binding to human anti-TNFR2, for example, CDR-H1, CDR-H2, CDR-H3, CDR-L1, CDR-L2, and/or CDR-L3 as described herein, and which is adjacent to or in frame with one or more framework sequences.

In some embodiments, the anti-TNFR2 antibodies or antibody fragments thereof comprise one or more conservative amino acid substitutions. A person of skill in the art will recognize that a conservative amino acid substitution is a substitution of one amino acid with another amino acid that has similar structural or chemical properties, such as, for example, a similar side chain. Exemplary conservative substitutions are described in the art, for example, in Watson et al., Molecular Biology of the Gene, The Benjamin/Cummings Publication Company, 4th Ed. (1987).

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, senne, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., *Acta Physiol Scand Suppl* 643: 55-67, 1998, Sasaki et al., *Adv Biophys* 35: 1-24, 1998). Amino acid substitutions to the antibodies of the disclosure may be made by known methods for example by PCR mutagenesis (U.S. Pat. No. 4,683,195).

In some embodiments, the anti-TNFR2 antibodies or antibody fragments thereof comprise a variable heavy chain sequence that comprises an amino acid sequence with at least about 95%, about 96%, about 97%, about 98%, or about 99%, sequence identity to the amino acid sequence set forth in SEQ ID NOs: 1, 3, 5, 7, 9, 48, or 11. In other embodiments, the anti-TNFR2 antibodies or antibody fragments thereof retains the binding (e.g., in a BIACORE assay) and/or functional activity of an anti-TNFR2 antibody or antibody fragment thereof that comprises the variable heavy chain sequence of SEQ ID Nos: 1, 3, 5, 7, 9, 48, or 11. In still further embodiments, the anti-TNFR2 antibodies or antibody fragments thereof comprise the variable heavy chain sequence of SEQ ID Nos: 1, 3, 5, 7, 9, 48, or 11 and have one or more conservative amino acid substitutions, e.g., 1, 2, 3, 4, 5, 1-2, 1-3, 1-4 or 1-5 conservative amino acid substitutions in the heavy chain variable sequence. In yet further embodiments, the one or more conservative amino acid substitutions fall within one or more framework regions in SEQ ID NOs: 1, 3, 5, 7, 9, 48, or 11 (based on the numbering system of Kabat). In other embodiments, the anti-TNFR2 antibodies or antibody fragments thereof comprise the variable heavy chain sequence of SEQ ID Nos: 1, 3, 5, 7, 9, 48, or 11 and lack one or more C-terminal amino acid residues of SEQ ID Nos: 1, 3, 5, 7, 9, 48, or 11, respectively.

In particular embodiments, the anti-TNFR2 antibody or antibody fragment thereof comprises a variable heavy chain sequence with at least about 95%, about 96%, about 97%, about 98%, or about 99% sequence identity to the anti-TNFR2 heavy chain variable region sequence set forth in SEQ ID NOs: 1, 3, 5, 7, 9, 48, or 11, comprises one or more conservative amino acid substitutions in a framework region (based on the numbering system of Kabat), and retains the binding and/or functional activity of an anti-TNFR2 antibody or antibody fragment thereof that comprises a variable heavy chain sequence as set forth in SEQ ID NOs: 1, 3, 5, 7, 9, 48, or 11 and a variable light chain sequence as set forth in SEQ ID NOs: 2, 4, 6, 8, 10, or 12.

In some embodiments, the anti-TNFR2 antibodies or antibody fragments thereof comprise a variable light chain sequence that comprises an amino acid sequence with at least about 95%, about 96%, about 97%, about 98%, or about 99%, sequence identity to the amino acid sequence set forth in SEQ ID NOs: 2, 4, 6, 8, 10, or 12. In other embodiments, the anti-TNFR2 antibodies or antibody fragments thereof retains the binding (e.g., in a BIACORE assay) and/or functional activity of an anti-TNFR2 antibody or antibody fragment thereof that comprises the variable light chain sequence of SEQ ID Nos: 2, 4, 6, 8, 10, or 12. In still further embodiments, the anti-TNFR2 antibodies or antibody fragments thereof comprise the variable light chain sequence of SEQ ID Nos: 2, 4, 6, 8, 10, or 12 and have one or more conservative amino acid substitutions, e.g., 1, 2, 3, 4, 5, 1-2, 1-3, 1-4 or 1-5 conservative amino acid substitutions in the light chain variable sequence. In yet further embodiments, the one or more conservative amino acid substitutions fall within one or more framework regions in SEQ ID NOs: 2, 4, 6, 8, 10, or 12 (based on the numbering system of Kabat).

In particular embodiments, the anti-TNFR2 antibody or antibody fragment thereof comprises a variable light chain sequence with at least about 95%, about 96%, about 97%, about 98%, or about 99% sequence identity to the anti-TNFR2 light chain variable region sequence set forth in SEQ ID NOs: 2, 4, 6, 8, 10, or 12, comprises one or more conservative amino acid substitutions in a framework region (based on the numbering system of Kabat), and retains the binding and/or functional activity of an anti-TNFR2 antibody or antibody fragment thereof that comprises a variable heavy chain sequence as set forth in SEQ ID NOs: 1, 3, 5, 7, 9, 48, or 11 and a variable light chain sequence as set forth in SEQ ID NOs: 2, 4, 6, 8, 10, or 12. 101651 In some embodiments, the antibody is a full-length antibody. In other embodiments, the antibody is an antibody fragment including, for example, an antibody fragment selected from the group consisting of: Fab, Fab', $F(ab)_2$, Fv, domain antibodies (dAbs), and complementarity determining region (CDR) fragments, single-chain antibodies (scFv), chimeric antibodies, diabodies, triabodies, tetrabodies, miniantibodies, and polypeptides that contain at least a portion of an immunoglobulin that is sufficient to confer TNFR2 specific binding to the polypeptide.

In some embodiments, a variable region domain of an anti-TNFR2 antibody disclosed herein may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly, a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab fragment, or to provide further domains, such as antibody CH2 and CH3 domains.

In some embodiments, the anti-TNFR2 antibodies disclosed herein may also comprise one or both of the antibody constant regions disclosed in SEQ ID NOS: 50 and 51 or a variant thereof. The sequences provided in SEQ ID NOS: 50 and 51 are of human origin and represent a human IgG1 heavy chain constant region and a human kappa light chain constant region, respectively. One of skill in the art will also acknowledge that in order to evaluate the anti-tumor efficacy of an anti-TNFR2 antibody in a murine tumor model it may be desirable to prepare a recombinant anti-TNFR2 antibody comprising a non-native constant region. In another embodiment, the anti-TNFR2 antibodies or antibody fragments thereof may comprise SEQ ID NO: 50 or 51 and have a C- or N-terminal truncation (e.g., a C-terminal lysine truncation).

The rules that govern whether a particular mAb will possess agonistic or antagonistic properties, however, are currently unclear. More specifically, the relationship between epitope location, isotype and biological activity of anti-TNFR2 antibodies is not completely understood. For example, Torrey et al. discloses antibodies capable of antagonizing TNFR2 and describes the antagonistic antibodies as either dominant or recessive antagonists, based on the biological activity of the antibody in the presence of TNF-α agonism (Torrey et al., *Sci. Signal.,* 10:462, 2017). Torrey et al demonstrates that TNFR2 antagonistic antibodies A and B, both of which were selected to prevent TNF-α ligand binding and TNFR2 activation were not able to exert an antagonistic effect in a Treg assay in the presence of exogenous TNF. However, anti-TNFR2 antibodies 1 and 2 were able to overcome TNF agonism in a dose-dependent fashion and decrease Treg expansion in the presence of a generous concentration of TNF. This resulted in the classification of antibodies A and B as recessive TNFR2 antagonists and antibodies 1 and 2 as dominant TNFR2 antagonists. Based on epitope mapping studies, Torrey et al concludes that the dominant and recessive anti-TNFR2 antibodies bind to distinct epitopes located in the CRD3/4 and CRD2 regions, respectively (Torrey et al., *Sci. Signal.,* 10:462, 2017).

WO 2016/187068 discloses that the dominant antagonistic anti-TNFR2 antibodies described by Torrey et al. recognize epitopes that contain one or more residues of the KCRPG motif (residues 142-146 within human TNFR2 (SEQ ID NO: 7 in WO 2016/187068). WO 2019/094559 discloses additional dominant antagonistic TNFR2 antibodies that bind one or more epitopes within CRD3 or CD4 of TNFR2, without the need to bind an epitope within the KCRPG motif. The antagonistic anti-TNFR2 antibodies disclosed in Torrey et al., WO 2016/187068 and WO 2019/094559 exhibit one or more beneficial biological properties, such as the ability to kill and/or inhibit the proliferation of T-reg cells, kill and/or inhibit the proliferation of TNFR2+ cancer cells, kill and/or inhibit the proliferation of myeloid-derive suppressor cells (MDSCs), and/or induce the proliferation of effector T cells. Torrey et al. report that the functional activity of both of the dominant anti-TNFR2 antagonist antibodies is independent of Fcγ receptor engagement and receptor cross-linking using exogenous IgG methods (Torrey, et al., *Sci. Signal.,* 10:462, 2017).

Bioinvent has a preclinical anti-TNFR2 antibody, designated as BI-1808, in development for cancer immunotherapy (Targeting TNFR2 for cancer immunotherapy: Ligand blocking depletors versus receptor agonists, Martensson, et al AACR 2020, Abstract #936, Martensson et al, AACR 2020, Abstract #725). BI-1808 blocks TNF-α binding to TNFR2, inhibits TNF-α-induced TNR2 signaling and requires FcγR engagement for biological activity. In vivo mode-of-action studies indicated that dominant mechanism of action of BI-1808 is intra-tumoral Treg depletion and improved CD8/Treg ratios (Martensson, et al). In vivo therapeutic activity of the murine BI-1808 surrogate antibody (3F10 in murine IgG2a format) is characterized by an obligate dependence on FcγR-interactions with activatory Fc receptors. WO 2020/089474, filed by Bioinvent, describes antagonistic anti-TNFR2 antibodies and indicates that the epitope for the antagonist antibodies is in the center of domain 3 (encompassing aa 134 to 160), with some dependence on CRD4.

WO 2017/040312 discloses agonistic anti-TNFR2 antibodies that function to promote TNFR2 signaling and the expansion/proliferation of Tregs. The agonistic antibodies are further characterized as binding specifically to an epitope comprising the sequence KCSPG. Recent posters published by HiFiBio, BioInvent and Merrimack Pharmaceuticals describe agonistic anti-TNFR2 antibodies that are under development to modulate T cell activities in the tumor microenvironment.

The HiFiBio candidate, HFB200301, is a humanized anti-TNFR2 antibody, does not compete with TNF for TNFR2 binding, stimulates activated CD4 and CD8 T cells and enhances their proliferation in vitro, and displays Fc receptor-independent anti-tumor activity in a syngeneic MC38 tumor model in human TNFR2 knock-in mice (Wei et al., AACR 2020, Poster #2282).

The Bioinvent candidate BI-1910 also does not block TNF-α from binding to TNFR2, is characterized by strong activation of TNFR2 signaling, does not require Fc engagement for biological activity, but shows enhanced activity as an IgG isotype or variant Fc regions designed to improve binding to inhibitory as opposed to activating FcγR. WO 2020/089473, filed by Bioinvent, describes agonistic anti-TNFR2 antibodies and indicates that the agonist antibodies seem to bind to the distal C-terminal part of CRD3 and that binding likely depends on to a greater extent on CRD4 than antagonistic anti-TNFR2 antibodies evaluated in the same epitope mapping experiments. Treatment with a murine surrogate of BI-1910 (i.e., antibody 5A05 in a murine IgG1 format) antibody resulted in an early increase in intratumoral CD8 T cells in a CT26 syngeneic model resulting in an enhanced CD8/Treg ratio (Martensson, et al AACR 2020, Abstract #936).

Merrimack's anti-TNFR2 antibody candidate, MM-401, binds to the same epitope as murine antibody Y9 (described in Tam et al., *Sci. Transl. Med.,* 11(512), 2019 as binding to an epitope in CRD1), and relies on a co-stimulatory activity on T cells for its dominant mechanism of action. More specifically, it stimulates CD4 and CD8 T cells in vitro and in vivo, mediates the downregulation of immunosuppressive markers and TNFR2 on T cells, and increases the magnitude and effector function of tumor-infiltrating CD8 T cells. Anti-tumor efficacy in mouse syngeneic tumor models is FcγR dependent and enhanced by engagement of inhibitory FcγRs (Richards et al, MM-401, a novel anti-TNFR2 antibody that induces T cell co-stimulation. AACR 2019, Abstract #4848).

In order to understand the effect of an antibody's isotype on its in vivo therapeutic activity one of skill in the art will readily appreciate that it is desirable to engineer recombinant antibodies having the same variable regions (VH and VL) combined with more than heavy chain constant region characterized by different isotypes and inherently different binding affinities for activating and inhibitory Fcγ receptors (FcγRs). For example, one of skill in the art would know that murine IgG2A functionally resembles human IgG1 and is more likely to bind activating FcγRs, whereas mouse IgG1 is considered the closest functional equivalent of human IgG4 and more likely to reduce binding to FcγRs.

In addition to binding to TNFR2, full-length versions of the antibody molecules comprising the VH and VL sequences disclosed herein will also bind to Fcγ receptors. Accumulating evidence indicates that immunomodulatory antibodies engage different types of Fcγ receptors for their modulatory activities and effector functions. More specifically, it is known that how antibody immune complexes modulate immune cell activation is determined by their relative engagement of activating and inhibitory Fcγ receptors. Different antibody isotypes bind with different affinity to activating and inhibitory Fcγ receptors, resulting in different activating:inhibitory ratios (A:I ratios) (Nimmerjahn et al., *Science,* 310(5753):1510-2, 2005, Teige et al., *Front Immunol,* 10, 2019).

In vivo research of the last decade suggests that the anchoring of antitumor necrosis factor (TNF) receptor superfamily (TNFRSF) receptor antibodies to cell-expressed Fcγ receptors (FcγR) can be of decisive relevance for their receptor-stimulatory activity. In particular, the FcγRIIB receptor has been shown to positively regulate the activity of immunomodulatory agonistic antibodies (Liu et al., *Antibodies,* 9:64, 2020). Li and Ravetch have reported that the anti-tumor activities of agonistic CD40 antibodies require the engagement of inhibitory Fcγ receptor (Li and Ravetch, *Proc. Nat'l Acad. Sci.* (USA), 109:10966-71, 2012, Li and Ravetch, 333(6045): 1030-1034, 2011). Publications reporting anti-tumor data for other category II costimulatory members of the TNFSF (e.g., 4-1BB and OX40) have confirmed the ability of FcγRIIB/antibody interactions to positively regulate the activity of immunomodulatory agonistic antibodies targeting TNFSF receptors (Zhang et al., *J Biol Chem.,* 291(53): 27134-27146, 2016, White et al., *J. Immunol.,* 187, 1754-1763, 2011, White et al., *J. Immunol.,* 193, 1828-1835, 2014 and Yu et al., *Cancer Cell,* 33, 664-675, 2018).

The literature on antibody development may, or may not, yield some rules about the significance of FcγR interactions in determining the biological activities of anti-TNFR2 antibodies. Research on the biological activity of other anti-TNFR category II specific antibodies (e.g., anti-CD40, anti-OX40, anti-CD95, anti-Fn14) has revealed that the idiotype of the anti-TNFR IgG antibody is not the decisive factor responsible for conferring agonistic activity. The dominant factor required for strong agonism by antibodies targeting TNFR category 11 receptors is Fcγ-receptor (FcγR) binding (Medler et al. *Cell Death and Disease,* 10:224, 2019, Li and Ravetch, *PNAS* (*USA*), 109:10966-71, 2012 and White et al., *J. Immunol.,* 187, 1754-1763, 2011).

One of skill in the art will recognize that Fc engineering can be used to modify the anti-tumor activities (e.g., effector functions) of the disclosed anti-TNFR2 antibodies to enhance their agonistic activity and/or effector functions. The literature describes several alternative Fc engineering strategies all of which are suitable to design an engineered anti-TNFR2 antibody comprising a variable region of one of the antibodies disclosed herein to modulate TNF/TNFR2 axis in either an FcγR dependent or FcγR-independent manner. For example, in order to produce an antibody optimized for immunostimulation, a variable region domain of an anti-TNFR2 antibody disclosed herein may be covalently attached at a C-terminal amino acid to an immunoglobulin Fc domain engineered to confer a low A:I ratio. Therefore, in some embodiments an anti-TNFR2 antibody disclosed herein could be engineered to have enhanced binding to an inhibitory FcγR (e.g., CD32b) in order to stimulate effector T cell activation through hypercrosslinking of TNFR2 trimeric ligand receptor complexes into a supramolecular signaling cluster.

For example, increased CD32b (FcγRIIB) binding affinity can be engineered into a human IgG1 constant region by introducing two mutations S267E and L328F (i.e., "SELF") (serine at position 267 replaced with glutamic acid and leucine at position 328 replaced with phenylalanine) into a human IgG1 constant region (Chu et al, Mol. Immunol. 45(15):3926-3933, 2008). These two Fc mutations have been reported to increase binding affinity to CD32b by approximately 430-fold, with minimal changes in binding to FcRI and FcRIIA-H131 and eliminating binding to FcRIIIA-V158 compared to WT hIgG1 (Liu et al., *Antibodies,* 9:64, 2020). In vivo, an S267E/L328F modified anti-CD40 hIgG2 antibody had enhanced ability to activate T cells in hFcR/hCD40 transgenic mice when compared to either WT hIgG1 or hIgG2 variants (Liu et al., *Antibodies,* 9:64, 2020 and Dahan et al., *Cancer Cell,* 29, 820-831, 2016). An anti-DR5 antibodies carrying a single S267E ("SE") mutation has been reported to increase human IgG1 affinity for FcγRIIB several hundred-fold, and to confer improved tumor regression in mouse models humanized for FcγRIIB (Li and Ravetch, *Proc. Nat'l Acad. Sci*., (USA), 109:10966-71, 2012).

Alternatively, a variable region domain of an anti-TNFR2 antibody disclosed herein may be covalently attached at a C-terminal amino acid to an immunoglobulin Fc domain engineered to comprise either the V12 mutations (E233D/G237D/P238D/H268D/P271G/A330R) or the V11 mutations (G237D/H268D/P271G/A330R) defined by Mimoto et al. The V12 and V11 mutations were elucidated based on studies conducted to expand on the observation that the mutation P238D that enhanced binding to FcγRIIB while either completely abolishing or severely reducing binding to activatory FcRs (FcRI, FcRHIA-H131, FcRIIIA-V131) compared to WT hIgG1 (Mimoto et al., *Protein Eng. Des. Sel.,* 26:589-598, 2013). The V12 and V11 mutations have been reported to enhance FcγRIIB binding approximately 217-fold and 40-fold, respectively, compared to wild type human IgG1 (Mimoto et al.).

Zhang et al. performed a systematic evaluation of different Fc engineering approaches on the enhancement of the agonism and effector functions of the anti-OX40 antibody SF2. The study compared the "SELF" mutations, the V12 mutations and Fc mutations that facilitate hexamerization of IgG1 Abs when bound to cell surface antigens as alternative strategies to enhance the agonism and effector functions of the antibody (Zhang et al., *J. Bio. Chem.,* 291(53):27134-27146, 2016). The hexamerization mutations evaluated included single E345R and E430G mutations, an E345R/E430G double mutation and an E345R/E430G/S440Y triple mutation (Diebolder et al., *Science* 343, 1260-1263, 2014). The mutations were expected to enhance the agonism/effector functions of SF2 by promoting the clustering of OX40 receptors without the dependence on FcγRIIB cross-linking. The single E345R mutation was reported to have the best effect on the agonism of SF2, independent of FcγRIIB cross-linking. Zhang et al. conclude that the E345R hexamerization mutation can facilitate higher agonism independent of FcγRIIB cross-linking, a feature that could confer effector function regardless of FcγR expression levels in the local microenvironment. However, although FcγR-independence could be considered an advantage for tumor microenvironments with low levels of infiltration of FcγR expressing cells, it could stimulate agonism non-specifically and result in undesired off-target effects (Zhang et al., *J. Biol. Chem.,* 291(53):27134-27146, 2016). Medler and Wajant have recently described TNFRSF receptor-specific antibody fusion proteins with targeted controlled FcγR independent agonistic activity, by genetic fusion of TNFR2-specific IgG1 antibody C4-IgG1(N297A) (point mutation chosen to interfere with binding to FcγR2A, FcγR2B, and FcγR3A) with heterologous cell surface anchoring domains (Medler et al., *Cell Death and Disease,* 10:224, 2019). The cell surface anchoring domains included cytokines (murine IL-2, murine GITRL, human GITRL or murine 4-1BBL) allowing binding to corresponding cytokine receptor expressing cells; and scFvs specific the tumor-associated antigens CD19, CD20, and CD70. All four C4-IgG1(N297A) cytokine fusion proteins investigated activate TNFR2 in an FcγR-independent manner upon anchoring to their corresponding cell surface exposed cytokine receptor. Similarly, all of the anti-TNFR2 scFv specific fusion proteins activated TNFR2 signaling in HeLa-TNFR2 cells cocultured with Jurkat cells expressing the corresponding tumor antigen.

Medler and Wajant speculate that the use of tumor antigen-specific scFvs as anchoring domains may not only eliminate the requirement for FcγR-binding in the TME but also promises to reduce systemic side effects (Medler et al., *Cell Death and Disease,* 10:224, 2019). Further, because tumor-associated antigens can reach much higher expression levels as compared to FcγRs, they further speculate that cell surface-anchored anti-TNFRSF receptor antibody fusion proteins can even gain higher total activity than FcγR-bound conventional anti-TNFRSF receptor antibodies (Medler et al.). The use of a variable region domain of an anti-TNFR2 antibody disclosed as a fusion protein engineered to comprise an anchoring domain specific for a cell surface target present in the TME could facilitate the use the antibodies disclosed herein for the antibody-based immunotherapy of cancer.

Methods of Producing Antibodies

Anti-TNFR2 antibodies or antibody fragments thereof may be made by any method known in the art. For example, a recipient may be immunized with DNA encoding human TNFR2 or fragment thereof, fusion proteins comprising the full-length ectodomain of TNFR2, or any combination of one or more of the four repeated cysteine-rich domains (CRD1, CRD2, CRD3 and CRD4) combined with Ig Fc domain, or a polypeptide sequence encoding a target epitope from anyone of the CRDs, or recombinant cells engineered to overexpress human TNFR2. Any suitable method of immunization can be used. Such methods can include adjuvants, other immune stimulants, repeat booster immunizations, and the use of one or more immunization routes.

Different forms of a TNFR2 antigen may be used to elicit an immune response for the identification of biologically active anti-TNFR2 antibodies. Thus, the eliciting TNFR2 antigen may be a single epitope, multiple epitopes, or the entire protein alone or in combination with one or more immunogenicity enhancing agents. In some aspects, the eliciting antigen is an isolated soluble full-length protein, or a soluble protein comprising less than the full-length sequence (e.g., immunizing with a peptide comprising a single CRD domain of human TNFR2 or a peptide derived from a particular subdomain of a TNFR2 ectodomain). As used herein, the term "portion" refers to the minimal number of amino acids or nucleic acids, as appropriate, to constitute an immunogenic epitope of the antigen of interest. Any genetic vectors suitable for transformation of the cells of interest may be employed, including, but not limited to adenoviral vectors, plasmids, and non-viral vectors, such as cationic lipids.

It is desirable to prepare monoclonal antibodies (mAbs) from various mammalian hosts, such as mice, rodents, primates, humans, etc. Description of techniques for preparing such monoclonal antibodies may be found in, e.g., Sties et al. (eds.) BASIC AND CLINICAL IMMUNOLOGY (4$^{th}$ ed.) Lance Medical Publication, Los Altos, CA, and references cited therein; Harlow and Lane (1988) ANTIBODIES: A LABORATORY MANUAL CSH Press; Goding (1986) MONOCLONAL ANTIBODIES: PRINCIPLES AND PRACTICE (2$^{nd}$ ed.) Academic Press, New York, NY. Typically, spleen cells from an animal immunized with a desired antigen are immortalized, commonly by fusion with a myeloma cell (Kohler and Milstein, *Eur. J. Immunol.,* 6(7):511-9, 1976). Alternative methods of immortalization include transformation with Epstein Barr Virus, oncogene, or retroviruses, or other methods known in the art. See. e.g., Doyle et al. (eds. 1994 and periodic supplements) CELL AND TISSUE CULTURE: LABORATORY PROCEDURES, John Wiley and Sons, New York, NY. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host. Alternatively, one may isolate DNA sequences which encode a monoclonal antibody or an antigen binding fragment thereof by screening a DNA library from human B cells according, e.g., to the general protocol outlined by Huse et al. (1989) *Science* 246: 1275-1281. Thus, antibodies may be obtained by a variety of techniques familiar to researchers skilled in the art.

Other suitable techniques involve selection of libraries of antibodies in phage, yeast, virus or similar vector. See e.g., Huse et al. supra; and Ward et al. (1989) *Nature* 341:544-546. The polypeptides and antibodies disclosed herein may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literatures. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,9396,345; 4,277,437; 4,275,149: and 4,366,241. Also, recombinant immunoglobulins may be produced, see Cabilly U.S. Pat. No. 4,816,567; and Queen et al. (1989) *Proc. Nat'l Acad Sci. USA* 86: 10029-10023; or made in transgenic mice, see Nils Lonberg et al. (1994), *Nature* 368:856-859; and Mendez et al. (1997) *Nature Genetics* 15: 146-156; TRANSGENIC ANIMALS AND METHODS OF USE (WO 2012/62118), Medarex, Trianni, Abgenix, Ablexis, OminiAb, Harbour and other technologies.

In some embodiments, the ability of the produced antibody to bind to TNFR2 and/or other related members of the TNFR super family can be assessed using standard binding assays, such as surface plasmon resonance (SPR), FoteBio (BLI), ELISA, Western Blot, Immunofluorescent, flow cytometric analysis, chemotaxis assays, and cell migration assays. In some aspects, the produced antibody may also be assessed for its ability to block/inhibit TNFα/TNFR binding interactions either in solution or on the surface of cells.

The antibody composition prepared from the hybridoma or host cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 *J. Immunol. Meth.* 62:1-13). Protein G is recommended for all mouse isotypes and for human gamma3 (Guss et al., *EMBO J.* 5:1567-1575, 1986). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25 M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present disclosure. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-TNFR2 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Polynucleotides, Vectors, and Host Cells

Other embodiments encompass isolated polynucleotides that comprise a sequence encoding an anti-TNFR2 antibody or antibody fragment thereof, vectors, and host cells comprising the polynucleotides, and recombinant techniques for production of the antibody. The isolated polynucleotides can encode any desired form of an anti-TNFR2 antibody including, for example, full length monoclonal antibodies, Fab, Fab', $F(ab')_2$, and Fv fragments, diabodies, linear antibodies, single-chain antibody molecules, and multispecific antibodies formed from antibody fragments.

Some embodiments include isolated polynucleotides comprising sequences that encode the heavy chain variable region of an antibody or antibody fragment having the amino acid sequence of SEQ ID NOs: 1, 3, 5, 7, 9, 11, and 48. Some embodiments include isolated polynucleotides comprising sequences that encode the light chain variable region of an antibody or antibody fragment having the amino acid sequence of any of SEQ ID NOs: 2, 4, 6, 8, 10, and 12.

In an embodiment, the isolated polynucleotide sequence(s) encodes an antibody or antibody fragment having a light chain and a heavy chain variable region comprising the amino acid sequences of:

(a) a variable heavy chain sequence comprising SEQ ID NO: 1 and a variable light chain sequence comprising SEQ ID NO: 2;
(b) a variable heavy chain sequence comprising SEQ ID NO: 3 and a variable light chain sequence comprising SEQ ID NO: 4;
(c) a variable heavy chain sequence comprising SEQ ID NO: 5 and a variable light chain sequence comprising SEQ ID NO: 6;
(d) a variable heavy chain sequence comprising SEQ ID NO: 7 and a variable light chain sequence comprising SEQ ID NO: 8;
(e) a variable heavy chain sequence comprising SEQ ID NO: 9 and a variable light chain sequence comprising SEQ ID NO: 10;
(f) a variable heavy chain sequence comprising SEQ ID NO: 48 and a variable light chain sequence comprising SEQ ID NO: 10; and
(f) a variable heavy chain sequence comprising SEQ ID NO: 11 and a variable light chain sequence comprising SEQ ID NO: 12.

In another embodiment, the isolated polynucleotide sequence(s) encodes an antibody or antibody fragment having a light chain and a heavy chain variable region comprising the amino acid sequences of:

(a) a variable heavy chain sequence that is 90%, 95%, or 99% identical to SEQ ID NO: 1 and a variable light chain sequence that is 90%, 95%, or 99% identical to SEQ ID NO: 2;
(b) a variable heavy chain sequence that is 90%, 95%, or 99/identical to SEQ ID NO: 3 and a variable light chain sequence that is 90%, 95%, or 99% identical to SEQ ID NO: 4;
(c) a variable heavy chain sequence that is 900, 95%, or 99% identical to SEQ ID NO: 5 and a variable light chain sequence that is 90%, 95%, or 99% identical to SEQ ID NO: 6;
(d) a variable heavy chain sequence that is 90%, 95%, or 99% identical to SEQ ID NO: 7 and a variable light chain sequence that is 90%, 95%, or 99% identical to SEQ ID NO: 8;
(e) a variable heavy chain sequence that is 90%, 95%, or 99%/identical to SEQ ID NO: 9 and a variable light chain sequence that is 90%, 95%, or 99% identical to SEQ ID NO: 10; and
(f) a variable heavy chain sequence that is 90%, 95%, or 99% identical to SEQ ID NO: 11 and a variable light chain sequence that is 90%, 95%, or 99% identical to SEQ ID NO: 12.

The polynucleotide(s) that comprise a sequence encoding an anti-TNFR2 antibody or antibody fragment thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-TNFR2 antibodies or antibody fragments thereof can also be produced as fusion polypeptides, in which the antibody or fragment is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-TNFR2 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO 90/13646. In mammalian cells, mammalian signal sequences as well as viral secretory leaders, for example, the herpes simplex gD signal, can be used. The DNA for such precursor region is ligated in reading frame to DNA encoding the anti-TNFR2 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

Compositions and Methods of Treatment

The disclosure also provides compositions including, for example, pharmaceutical compositions that comprise an anti-TNFR2 antibody or antibody fragment thereof for use as a therapeutic drug for the treatment of patients having an epithelial cell-derived primary or metastatic cancer. In a particular embodiment, a therapeutically effective amount of the compositions described herein are administered to cancer patients to kill tumor cells. For example, the compositions described herein can be used to treat a patient with a tumor characterized by the presence of cancer cells expressing or overexpressing TNFR2 In some aspects, the disclosed compositions can be used to treat a patient with a tumor that does not express TNFR2, but the anti-TNFR2 will stimulate the immune response and cause the elevation of TNFR2 in tumor infiltrated immune cells.

A tumor may be a solid tumor or a liquid tumor. In certain embodiments, a tumor is an immunogenic tumor. In certain embodiments, a tumor is non-immunogenic. Non-limiting examples of cancers for treatment include squamous cell carcinoma, small-cell lung cancer, non small cell lung cancer, glioma, gastric cancer, renal cancer, ovarian cancer, liver cancer, colorectal cancer, kidney cancer, prostate cancer, thyroid cancer, neuroblastoma, pancreatic cancer, breast cancer, head and neck cancer, melanoma, bone cancer, uterine cancer, and other hematologic malignancies derived from either of the two major blood cell lineages such as myeloid cell line of lymphoid cell line.

In some aspects, the treatment of cancer represents a field where combination strategies are especially desirable since frequently the combined action of two, three, four or even more cancer drugs/therapies generates synergistic effects which are considerably stronger than the impact of a monotherapeutic approach. The agents and compositions (e.g., pharmaceutical compositions) provided herein may be used alone or in combination with conventional therapeutic regimens such as surgery, irradiation, chemotherapy and/or bone marrow transplantation (autologous, syngeneic, allogeneic or unrelated). The agents and compositions may also be used in combination with one or more of an antineoplastic agent, a chemotherapeutic agent, a growth inhibitory agent, a cytotoxic agent, an immune checkpoint inhibitor, costimulatory molecule, kinase inhibitors, angiogenesis inhibitors, small molecule targeted therapy drugs, and multi-epitope strategies. Thus, in another embodiment of the present disclosure, a cancer treatment may be effectively combined with various other drugs.

The disclosed anti-TNFR2 antibodies can be administered either alone or in combination with other compositions that are useful for treating cancer. In one embodiment, the disclosed antibodies can be administered either alone or in combination with other immunotherapeutics including other antibodies useful for treating cancer. For example, in an embodiment the other immunotherapeutic is an antibody against an immune checkpoint molecule selected from the group consisting of human programmed cell death protein 1 (PD-1), PD-L1 and PD-L2, lymphocyte activation gene 3 (LAG3), NKG2A, B7-H3, B7-H4, CTLA-4, GITR, VISTA, CD137, TIGIT and any combination thereof. In an alternative embodiment the second immunotherapeutic is an antibody to a tumor specific antigen (TSA) or a tumor associated antigen (TAA). Each combination representing a separate embodiment of the disclosure.

An anti-TNFR2 antibody may be able to be combined with an immunogenic agent (tumor vaccines) such as cancer cells, purified tumor antigen including recombinant proteins, peptides and carbohydrate molecules. By lowering the T cell activation threshold via TNFR2 activation, the tumor response in the host can be activated, allowing treatment of non-immunogenic tumors of those having limited immunogenicity.

An anti-TNFR2 antibody may be combined with checkpoint inhibitors such as PD1/PDL1 blockers, and other therapies that can overcome the tumor immune escape, such as PDL1/TGFb trap. Targeting TNFR2 synergizes with anti-PD-1 in animal models (Wei et al., AACR 2020, Poster #2282) indicating that TNFR2 costimulation and PD1 blockade could lead to an enhanced anti-tumor immune response than PD1 monotherapy.

Anti-TNFR2 antibodies can be combined with standard cancer treatment (e.g. surgery, radiation and chemotherapy). In these cases, it may be possible to reduce the dose of chemotherapy, improve the efficacy of chemotherapy and radiation therapy in cancer patients and prolong their survival.

The combination of therapeutic agents discussed herein can be administered concurrently as components of a bispecific or multi-specific binding agent or fusion protein or as a single composition in a pharmaceutically acceptable carrier. Alternatively, a combination of therapeutics can be administered concurrently as separate compositions with each agent in a pharmaceutically acceptable carrier. In another embodiment, the combination of therapeutic agents can be administered sequentially.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In some aspects, the pharmaceutical composition is administered to a subject to treat cancer.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound A composition of the present disclosure can be administered by a variety of methods known in the art. As will be appreciated by the skilled artisan, the route and/or mode of administration will vary depending upon the desired results. The active compounds can be prepared with carriers that will protect the compound against rapid releases, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

Dosage levels of the active ingredients in the pharmaceutical compositions may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions described herein may be administered in effective amounts. An "effective amount" refers to the amount which achieves a desired reaction or the desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease.

All patents and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The broad scope of this disclosure is best understood with reference to the following examples, which are not intended to limit the disclosures to the specific embodiments. The specific embodiments described herein are offered by way of example only, and the disclosure is to be limited by the terms of the appended claims, along with the full scope of the equivalents to which such claims are entitled.

EXAMPLES

General Methods

Stable cell lines expressing TNFR2 or TNFR1 were generated using electroporation by transfecting a selected host cell (i.e., CHO-K1, or HEK293T cells, both purchased from ATCC, or Jurkat NFκB cells from Kyinno #KC-0149) with pcDNA-based plasmids expressing TNFR2 from the *Homo sapiens* sequences (NCBI accession number NP_001057.1, SEQ NO: 52) or the *Macaca fascicularis* sequences (NCBI accession number XP_005544817.1, SEQ NO: 53), or the *Mus musculus* sequences (NCBI accession number NP_035740.2, SEQ NO: 54), or TNFR1 from the *Homo sapiens* sequences (NCBI accession number NP_001056.1, SEQ NO: 55). HEK293T cells expressing a membrane bound non-cleavable form of TNF from the Human sequence (SEQ ID NO: 57) was generated according to the information described by Horiuchi, T. et al. (*Rheumatology,* 1215-1228, 2010).

Expression was confirmed using appropriate antibodies 24 hours and 48 hours after transfection using flow cytometry to assay for surface expression. Antibiotic appropriate to the plasmid constructs was used to select the integrated cells. After 7-10 days of selection, limiting dilution was performed on the surviving cells in 96-well plate while keeping the transfectants under selection pressure.

When needed, after 10-14 days, single colonies were picked up for screening using flow cytometry with TNFR2 (R&D Systems, #FAB216A) and TNFR1 (R&D Systems, FAB225P)-specific antibodies. The top 3-5 highly expressed clones were chosen for further development. After a couple of passages, the expression level was confirmed by flow cytometry and image assay to make sure it is stable.

The sequences for the heavy and light chain variable regions for hybridoma clones were determined as described below. Total RNA was extracted from 1-2×$10^6$ hybridoma cells using the RNeasy Plus Mini Kit from Qiagen (Germantown, MD, USA). cDNA was generated by performing 5' RACE reactions using the SMARTer RACE 5'/3' Kit from Takara (Mountainview, CA, USA). PCR was performed using the Q5 High-Fidelity DNA Polymerase from NEB (Ipswich, MA, USA) to amplify the variable regions from the heavy and light chains using the Takara Universal Primer Mix in combination with gene specific primers for the 3' mouse constant region of the appropriate immunoglobulin. The amplified variable regions for the heavy and light chains were run on 2% agarose gels, the appropriate bands excised and then gel purified using the Mini Elute Gel Extraction Kit from Qiagen. The purified PCR products were cloned using the Zero Blunt PCR Cloning Kit from Invitrogen (Carlsbad, CA, USA), transformed into Stellar Competent *E. Coli* cells from Takara and plated onto LB Agar+50 ug/ml kanamycin plates. Direct colony Sanger sequencing was performed by GeneWiz (South Plainfield, NJ, USA). The resulting nucleotide sequences were analyzed using IMGT V-QUEST to identify productive rearrangements and analyze translated protein sequences. CDR determination was based on IMGT numbering.

Methods for flow cytometry, including fluorescence activated cell sorting detection systems (FACS®), are available. See, e.g., Owens et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J. Fluorescent reagents suitable for modifying nucleic acids, including nucleic acid primers and probes, polypeptides, and antibodies, for use, e.g., as diagnostic reagents, are available.

Molecular Probes (2003) Catalogue, Molecular Probes, Inc., Eugene, Oreg.; Sigma-Aldrich (2003) Catalogue, St. Louis, Mo.

Methods for protein purification including immunoprecipitation, chromatography, and electrophoresis are described. Coligan et al. (2000) *Current Protocols in Protein Science*, Vol. 1, John Wiley and Sons, Inc., New York. Chemical analysis, chemical modification, post-translational modification, production of fusion proteins, and glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391. Production, purification, and fragmentation of polyclonal and monoclonal antibodies are described. Coligan et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra.

Standard techniques for characterizing ligand/receptor interactions are available. See, e.g. Coligan et al. (2001) *Current Protocols in Immunology*, Vol. 4, John Wiley, Inc., New York. Standard methods of antibody functional characterization appropriate for the characterization of antibodies with particular mechanisms of action are also well known to those of skill in the art.

To enable efficacy studies in mice, chimeric TNFR2-specific antibodies were generated by using the anti-TNFR2 specific human VL and VL domains together with mouse constant region. The mouse Fc can be a mouse IgG2a (sequence ID NO: 58) (referred to herein as Ms IgG2a) that is ADCC competent, a mouse IgG1 (sequence ID NO:59) which is ADCC inert or a replacement of aspartic acid by alanine at position 265 (D265A) in mouse IgG1 (sequence ID NO:60) results in a complete abolishment of interaction between this isotype and low-affinity IgG Fc receptors. Baudino et al. (2008) J Immunol. 2008 Nov. 1; 181(9):6664-9.

An in-house TNFR2-specific antibody referred to herein as "Positive Control 3" (R2-PC3 or PC3), was prepared based on the publicly available information published in WO 2020/089474 (antibody designated therein as: 001-H10 VH" comprising: VH set forth in SEQ ID NO: 7; and VL set forth in SEQ ID NO: 8). The PC3 antibody was used as a control in the binding and functional assays used to evaluate and characterize the anti-TNFR2 specific antibodies disclosed herein.

Software packages and databases for determining, e.g., antigenic fragments, leader sequences, protein folding, functional domains, CDR annotation, glycosylation sites, and sequence alignments, are available.

Example 1: Generation of Anti-TNFR2 Antibodies

Fully human anti-human TNFR2 antibodies were generated by immunizing human Ig Trianni transgenic mice that express human antibody VH and VL genes (see, e.g., WO 2013/063391, TRIANNI® mice). The Trianni transgenic mice were generated by the Trianni company.

Immunization—TRIANNI mice described above were immunized with recombinant human TNFRII/TNFRSF1B Fc chimera protein (R&D Systems, #726-R2).

The immune response was monitored by retroorbital bleeds. The plasma was screened by ELISA or Imaging or FACS (as described below). Mice with sufficient anti-TNFR2 titers were used for fusions. Mice were boosted with the immunogen before sacrifice and removal of the spleen and lymph nodes.

Selection of mice producing anti-TNFR2 Antibodies—To select mice producing antibodies that bound TNFR2, sera from immunized mice was screened by ELISA or Imaging or FACS for binding to recombinant TNFR2 protein or cells expressing TNFR2 protein (CHO-K1—transfected with the TNFR2 gene, NCBI: NM_001066.3).

For ELISA, briefly, an ELISA plate coated with recombinant human TNFR2 protein (Acro Biosystems #TN1-H5222) was incubated with dilutions of serum from immunized mice, the assay plate was washed, and specific antibody binding was detected with a goat-anti-mouse-IgG-HRP conjugated secondary antibody (Jackson ImmunoResearch #115-036-071) and ABTS substrate (Moss #ABTS-1000). The plate was then read using an ELISA plate reader (Biotek).

For Imaging assay, briefly, CHO-K1 cells stably overexpressing human TNFR2 (NCBI: NM_001066.3) were plated into a 384-well plate (Corning #3985) and incubated in 37° C. overnight. Next day, diluted serum from immunized mice were added to the plates. Then cells were fixed by 2% paraformaldehyde (Alfa Aesar #J61899) and incubated followed by washing three times with PBST [PBS containing 0.05% Tween-20, Technova #1193)]. Goat anti-mouse-IgG Alexa Fluor 488 (ThermoFisher #A11001) and Hoechst 33342 nuclear stain (ThermoFisher #H3570) were added to the cells and incubated for 1 h. After washing three times with PBST, blocking buffer [0.5% BSA (ThermoFisher #37525) in DPBS (ThermoFisher #14040216)] was added to the plates. The plates were scanned and analyzed on an imaging machine (Cytation 5, Biotek).

For FACS, briefly, CHO-K1 or 300.19 cells stably overexpressing human TNFR2 (NCBI: NM_001066.3) were aliquoted in FACS buffer [PBS (Lonza #17-516Q) plus 2% FBS (Gibco #26140-079)] and incubated with serial dilutions of immunized mouse serum. Cells were fixed with 2% paraformaldehyde (Alfa Aesar #J61899) and then washed once with excess FACS buffer [PBS (Lonza, #17-516Q) plus 2% FBS (ThermoFisher #26140-079)]. A goat-anti-mouse secondary antibody conjugated with Alexa Fluor 647 (ThermoFisher #A-21235) was added to the cells and incubated for 1 hour, and the reactions were subsequently analyzed by flow cytometry (IntelliCyt iQue Screener PLUS).

Generation of Hybridomas Producing MAbs to TNFR2—To generate hybridomas producing human antibodies of the disclosure, splenocytes and lymph node cells were isolated from an immunized mouse and fused to an appropriate immortalized cell line, such as a mouse myeloma cell line. The resulting hybridomas were screened for the production of antigen-specific antibodies. For example, single cell suspensions of splenocytes and lymph node cells from immunized mice were fused to equal number of Sp2/0 non-secreting mouse IgG myeloma cells (ATCC, CRL 1581) by electrofusion. Cells were plated in flat bottom 96-well tissue culture plates followed by about 2 weeks of incubation in selection medium (HAT medium), and then switched to hybridoma culture media. Approximately 10-14 days after cell plating, supernatants from individual wells were screened by ELISA, Imaging or FACS (as described above).

The antibody secreting hybridomas were transferred to 24-well plates and screened again. If still positive for anti-TNFR2, the positive hybridomas were subcloned by sorting using a single cell sorter. The stable subclones were then cultured in vitro to generate small amounts of antibodies to be used for purification and further characterization.

Example 2: Binding Specificity of TNFR2 Antibodies

HEK293T cells stably overexpressing human TNFR2 or CHO-K1 stably overexpressing human TNFR1 were aliquoted in FACS buffer and incubated with serial dilutions of TNFR2 antibody. Cells were fixed with 2% paraformaldehyde (Alfa Aesar #J61899), and then washed once with excess FACS buffer [PBS (Lonza #17-516Q) plus 2% FBS (Thermo #26140-079). A secondary antibody conjugated with Alexa Fluor 647 was added to the cells. Following an incubation, the reactions were subsequently analyzed by flow cytometry. Alternatively, the HEK293T cells were seeded overnight into 384-well black clear bottom poly-D-lysine treated plates (Falcon #356697) incubated overnight at 37° C. in a tissue culture incubator. Test antibodies were serially diluted in a culture medium [DMEM (Thermo #11965-084) supplemented with 10% heat inactivated fetal bovine serum (Thermo #16140-071) and 1× anti-anti (Thermo #15240-062)] and transferred to the cells for binding assay. The concentration-response was fitted to a four-parameter logistic non-linear regression model in the GraphPad Prism software to obtain the $EC_{50}$ values.

The anti-human TNFR2 antibodies demonstrated strong binding to both human TNFR2 and cynomolgus TNFR2. Representative clone data is given in FIG. 2. The $EC_{50}$ values for their binding to human TNFR2 ranged from 0.10 nM to 0.38 nM (Table 3). Anti-TNFR2 mAb PC3 is an in-house control made based on publicly available sequence information (VH and VL amino acid sequences) for the antibody designated as “001-1H10”. The binding activity of PC3 was also evaluated in the same experiment and the $EC_{50}$ was measured to be 0.16 nM (FIG. 2B). As indicated in Table 3, the representative antibodies did not demonstrate any binding to human TNFR1 up to 10 μg/mL.

TABLE 3

Binding activity of anti-human TNFR2 antibodies in CHO-K1 cells stably overexpressing human TNFR1 or TNFR2

| mAb | TNFR2 $EC_{50}$ (nM) | TNFR1 $EC_{50}$ (nM) |
|---|---|---|
| R2_mAb-1 | 0.10 | No binding |
| R2_mAb-2 | 0.35 | No binding |
| R2_mAb-3 | 0.38 | No binding |
| R2_mAb-4 | 0.11 | No binding |
| R2_mAb-5 | 0.10 | No binding |
| R2_mAb-6 | 0.14 | No binding |

Example 3: Cross Reactivity of TNFR2 Antibodies

HEK293T cells stably overexpressing human TNFR2, cynomolgus TNFR2, or murine TNFR2 were aliquoted in FACS buffer and incubated with serial dilutions of TNFR2 antibody for 2 hours. Cells were fixed with 2% paraformaldehyde (Alfa Aesar, #J61899) and then washed once with excess FACS buffer [PBS (Lonza, #17-516Q) plus 2% FBS (Thermo #26140-079). A secondary antibody conjugated with Alexa Fluor 647 was added to the cells and incubated for 1 hour, and the reactions were subsequently analyzed by flow cytometry.

The concentration-response was fitted to a four-parameter logistic non-linear regression model in the GraphPad Prism software to obtain the $EC_{50}$ values.

The TNFR2 antibodies cross reacted strongly between human and cynomolgus TNFR2 (Table 4). For each of the six representative clones, the binding $EC_{50}$ values comparing human and cynomolgus TNFR2 were within 2-fold of each other (data not shown). In contrast, the TNFR2 antibodies did not bind to murine TNFR2 at up to 10

TABLE 4

Cross reactivity of anti-human TNFR2 antibodies in HEK293T cells stably overexpressing human TNFR2, cynomolgus TNFR2 or murine TNFR2

| mAb | Human TNFR2 Binding Activity | Cynomolgus TNFR2 Binding Activity | Murine TNFR2 Binding Activity |
|---|---|---|---|
| R2_mAb-1 | ++++ | ++++ | − |
| R2_mAb-2 | ++ | ++ | − |
| R2_mAb-3 | ++ | + | − |
| R2_mAb-4 | ++++ | ++++ | − |
| R2_mAb-5 | ++++ | ++++ | − |
| R2_mAb-6 | ++++ | +++ | − |

Example 4: Epitope Binning of TNFR2 Antibodies

The binding epitopes of TNFR2 antibodies were binned using a sequential binding assay format.

Anti-human Fc probes (Probe Life, #PL168-16004) were loaded into 96-well plates containing the assay buffer (PBS containing 0.02% Tween20 and 0.05% sodium azide) for 30 seconds (baseline step), then loaded into 96-wells containing the anti-TNFR2 antibodies for 180 seconds (association step, to capture the antibodies) followed by 30 second baseline step, then the probes were loaded into 96-well plate containing human TNFR2 His tag protein (Acro Biosystems #TN2-H5227, Lot #: 387-8AUF1-M1) for 180 seconds followed by another baseline step and then by 180 seconds association with the anti-TNFR2 antibodies purified from hybridoma. Data were processed using Gator software and a curve during the second association step that is distinct from that of the first association step indicates binding to an unoccupied epitope than the reference antibody. A lack of additional binding indicates epitope blocking to the reference antibody.

Figure 3:
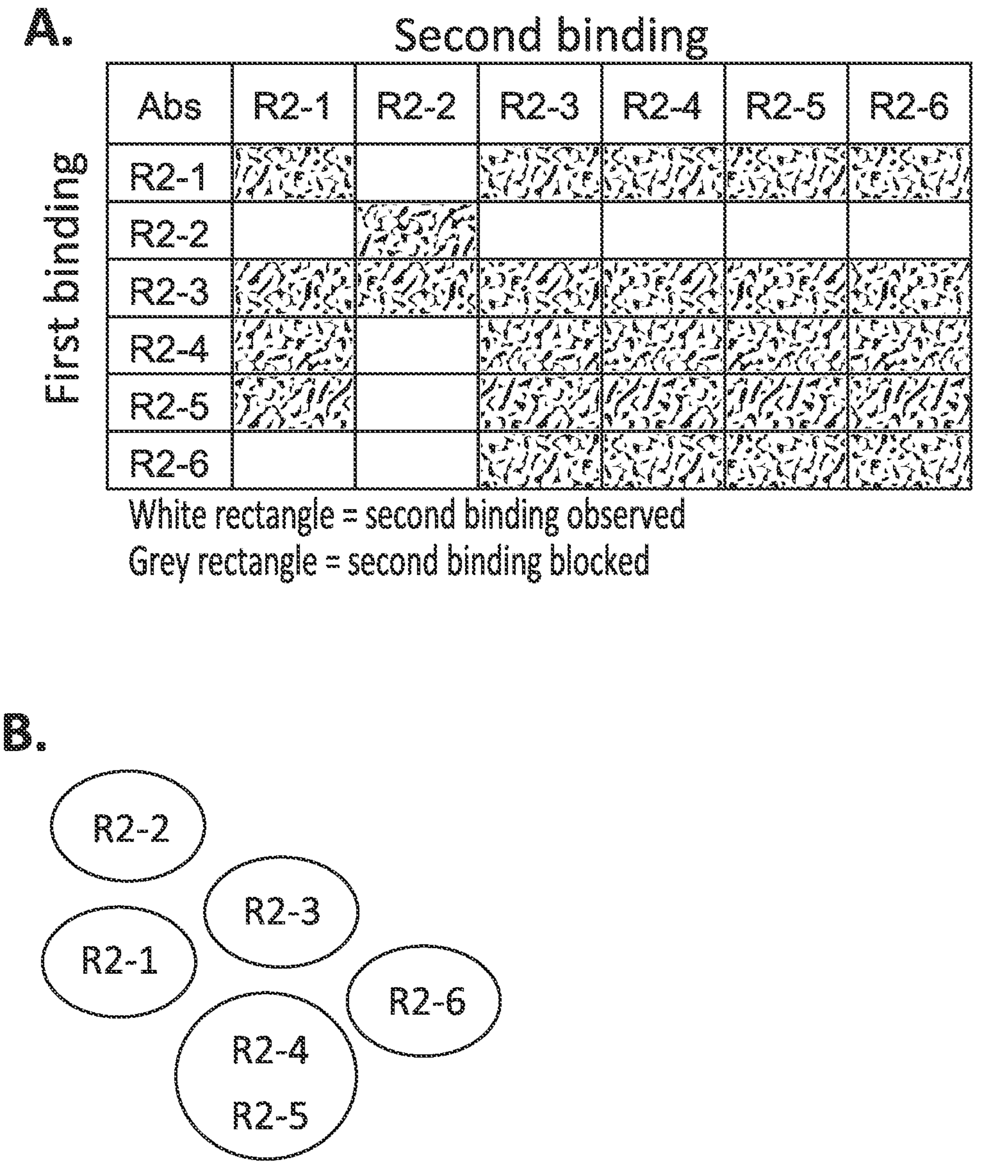
FIGS. 3A and 3B show the epitope binning and binning clusters of the anti-TNFR2 antibodies.

From this sequential binding experiment, the TNFR2 antibodies showed differing abilities to bind to the human TNFR2 when the receptor protein was already bound by another TNFR2 antibody (FIG. 3A). Based on these results, the antibodies can be grouped into five different bins that indicate the similarity of their binding epitopes (FIG. 3B).

Example 5: Binding Competition of TNFR2 Antibodies with TNF Ligand

The binding competition of TNFR2 antibodies against TNF ligand in binding to TNFR2 was evaluated in a high content imaging assay.

HEK293T cells overexpressing human TNFR2 receptor were seeded in 384-well clear bottom poly-D-lysine treated plates (Falcon #356697) and incubated overnight at 37° C. in a tissue culture incubator. Test antibodies were serially diluted in a culture medium [DMEM (Thermo #11965-084) supplemented with 10% heat inactivated fetal bovine serum (Thermo #16140-071) and 1× anti-anti (Thermo #15240-062) and transferred to the cells.

Following incubation for 1 hour, biotin-labeled TNF (Acro Biosystems, TNA-H8211) was added to the binding reactions and incubated for another hour. The cells were fixed with a 4% paraformaldehyde solution, and then washed two times with Dulbecco-buffered saline solution containing 0.5% bovine serum album. Subsequently, streptavidin conjugated with Alexa488 fluorophore (Biolegend #405235) and Hoechst nuclear stain (Thermo #62249) were added to the cell plates. Upon an hour incubation, the cells were washed two times with the Dulbecco-buffered saline solution containing 0.5% bovine serum album.

Biotin-TNF bound to the cell surface was detected by measuring the fluorescence signal on the Celigo cell cytometer (Nexcelom). The binding competition was determined, and the data were normalized by setting 100% inhibition as the signal in the absence of biotin-TNF.

Figure 4:
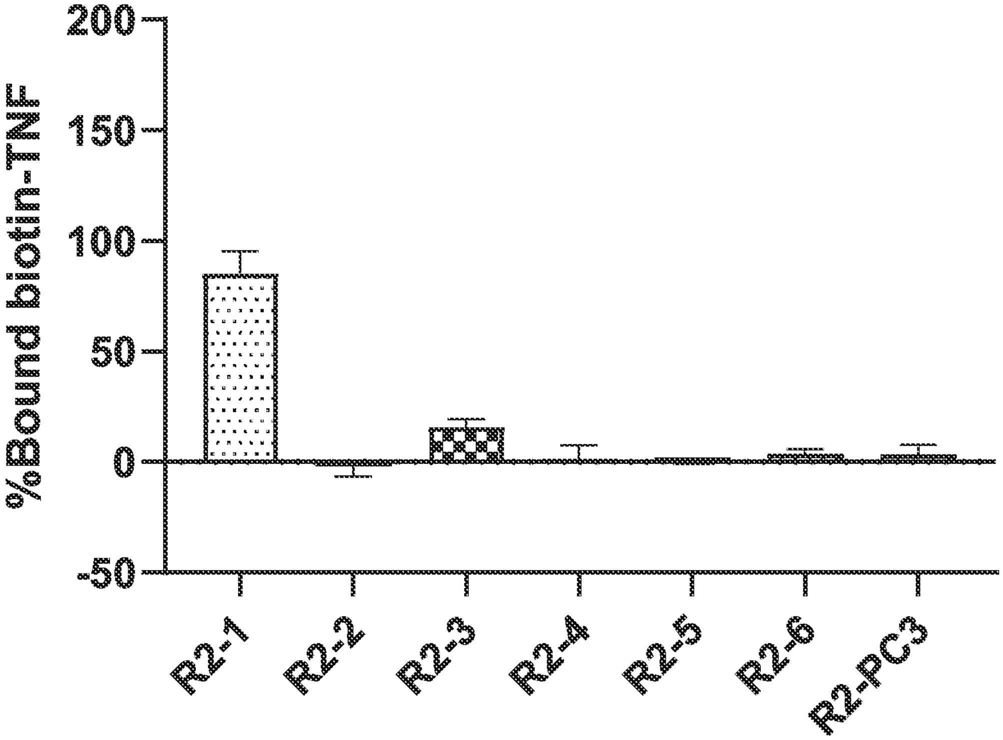
FIG. 4 shows the percentage of inhibition of the binding of biotinylated TNF to the human TNFR2-expressing HEK293T.

As shown in FIG. 4, the lead panel of TNFR2 antibodies differ in their ability to compete against the TNF ligand. Moreover, as demonstrated in FIG. 4, the representative clone R2-mAb1 did not inhibit the binding of TNF, whereas clones R2_mAb-2, R2_mAb-3, R2_mAb-4, R2_mAb-5, and R2_mAb-6 inhibited completely the binding of TNF to TNFR2. PC3 was also evaluated and showed complete inhibition.

Example 6: Antagonistic Activity of TNFR2 Antibodies in Soluble TNF-Stimulated NFκB Signaling TNFR2 activation has been known to signal to NFκB intracellularly (David J. MacEwan (2020) British Journal of Pharmacology (2002) 135, 855). An NFκB-responsive luciferase reporter assay was used evaluate the TNFR2 antibody antagonistic activities.

Test antibodies were serially diluted in a culture medium [RPMI1640 (Thermo #11875-085) supplemented with 10% heat inactivated fetal bovine serum (Thermo #16140-071) and 1× anti-anti (Thermo #15240-062)] and were transferred to 384-well solid bottom white plates (Corning #3752). TNF (R&D Systems #10291-TA) was added to the cell plates, followed by the addition of THP1 cell transfected with the NFκB luciferase reporter gene (Kyinno #KC-1216). The reactions were incubated overnight in a tissue culture incubator. On the next day, the expression of the luciferase reporter was measured by using the ONE-Glo luciferase detection reagent (Promega #E6130). Luminescence was measured in the Bio-Tek Neo2 plate reader. The activities of antibodies were determined, and the data were normalized by setting 100% inhibition as the signal in the absence of TNF.

Figure 5:
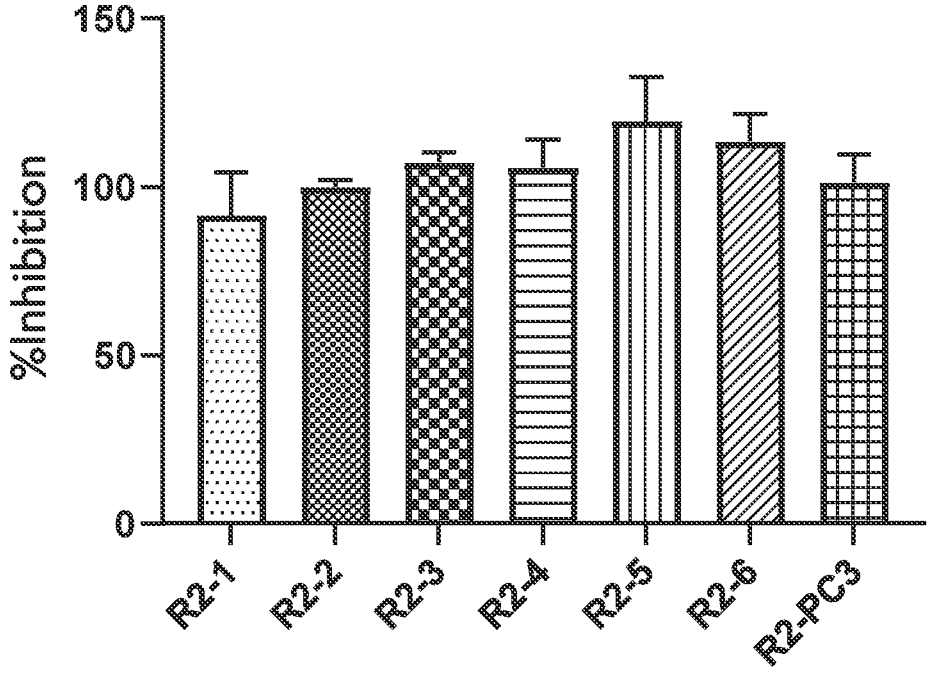
FIG. 5 shows the percentage of inhibition of soluble TNF-stimulated NFκB signaling by the TNFR2 antibodies in THP1 cells expressing the NFκB luciferase reporter.

TNF stimulation in the THP1 cells led to an increase in NFκB luciferase activity in the reporter cells that was inhibited by TNFR2 antagonist (FIG. 5). As represented by clones R2_mAb-1, R2_mAb-2, R2_mAb-3, R2_mAb-4, R2_mAb-5, and R2_mAb-6, the TNFR2 antibodies fully inhibited the NFκB luciferase activity induced by TNF. PC3 was also tested and showed complete signaling inhibition.

Example 7: Antagonistic Activity of TNFR2 Antibodies in Membrane TNF-Stimulated NFκB Signaling Test antibodies were serially diluted in culture medium [RPMI1640 (Thermo #11875-085) supplemented with 10% heat inactivated fetal bovine serum (Thermo #16140-071) and 1× anti-anti (Thermo #15240-062)] and were transferred to 384-well solid bottom white plates (Corning, #3752). HEK293T overexpressing membrane bound TNF were added to the cell plates, followed by the addition of Jurkat cells overexpressing the human TNFR2 and the NFκB luciferase reporter gene. The reactions were incubated overnight in a tissue culture incubator. On the next day, the expression of the luciferase reporter was measured by using the ONE-Glo luciferase detection reagent (Promega #E6130). Luminescence was measured in the Bio-Tek Neo2 plate reader. The data were normalized by setting 100% inhibition as the signal in the absence of the membrane TNF.

Figure 6:
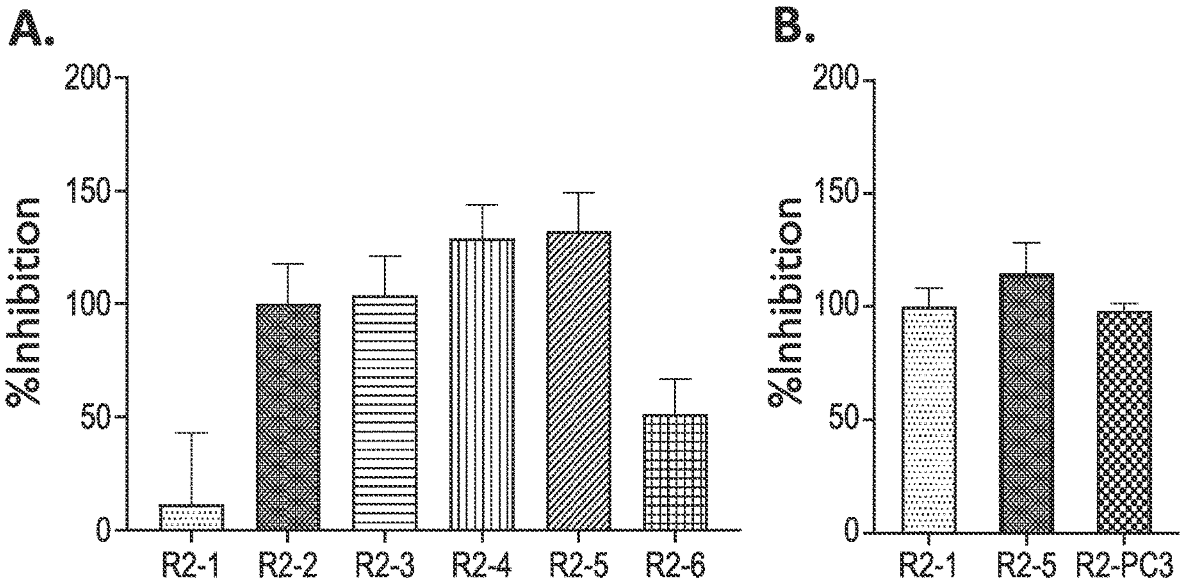
FIGS. 6A-6B show the percentage of inhibition of membrane TNF-stimulated NFκB signaling by the TNFR2 antibodies in Jurkat cells expressing the recombinant TNFR2 and the NFκB luciferase reporter tested at 15 nM (A) and 8 nM (B).

As shown in FIG. 6A, the lead panel of TNFR2 antibodies differ in the antagonistic activity toward the TNFR2 signaling stimulated by membrane TNF. Clones R2_mAb-1 and R2_mAb-6 inhibited partially the signaling. Clones represented by R2_mAb-2, R2_mAb-3, R2_mAb-4, R2_mAb-5 showed complete blocking of TNFR2 signaling. In comparison to PC3, R2_mAb-4 and R2_mAb-5 showed similar blocking activities (FIG. 6B).

Example 8: Activities of TNFR2 Antibodies in the Absence or Presence of Cross-Linking To evaluate the activities of TNFR2 antibodies upon antibody crosslinking, we employ either THP1 cells, which express FcγRs, or an anti-human IgG Fcγ fragment specific $F(ab')_2$ to crosslink the antibodies.

Jurkat NFkB luciferase reporter cells were cultured alone or co-cultured with THP1 cells. The TNFR2 antibody R2_mAb-4 was applied as to the cells at various concentration. In the absence of THP1 cells, the TNFR2 antibody R2_mAb-4 did not show any activity (FIG. 7B). As pictured in the diagram (FIG. 7A), when the TNFR2 antibody was crosslinked by the FcγRs on the THP1 cells, R2_mAb-4 exhibited an agonist activity evidenced by an increase in the luciferase reporter activity (FIG. 7B).

The crosslinking effect was also assessed by using the anti-human IgG Fcγ fragment specific $F(ab')_2$. CD8 T effector cells were cultured in RPMI1640 (Thermo #11875-085) supplemented with 10% heat inactivated fetal bovine serum (Thermo #16140-071), Ix anti-anti (Thermo #15240-062), 10 mM HEPES (Thermo, 15630-080), 1 mM sodium pyruvate (Thermo #11360-070), 0.1 mM MEM-NEAA (Thermo #11140-050) and 1× anti-anti (Thermo, 15240-062) and were activated by treatment with ImmunoCult™ (STEMCELL #10991) and IL-2 (Biolegend #589106). Test antibodies were serially diluted in an assay medium (RPMI1640 supplemented with 10% heat inactivated fetal bovine serum and 1× anti-anti) in the presence or absence of anti-human IgG Fcγ fragment specific $F(ab')_2$ (Jackson, #109-006-098) and transferred to 384-well clear bottom black plates (Falcon #353962). The CD8 T cells were harvested and co-cultured with isolated T regulatory cells. The supernatants were taken for measurement of the released IFNγ. The levels of IFNγ were quantified using the human IFNγ AlphaLISA reagents (PerkinElmer #AL217F) against a standard curve constructed using known concentrations human IFNγ. The signal was measured in the Bio-Tek Neo2 plate reader. All the experiments were performed in triplicates.

The presence of T regulatory cells in the co-culture with CD 8 T cells caused a suppression in IFNγ secretion under the current experiment conditions (data not shown). In the presence of the TNFR2 antibodies alone, there was a reduction in IFNγ secretion compared to control (FIG. 7C).

Furthermore, as shown in FIG. 7C, crosslinking the TNFR2 antibodies, caused an increase in IFNγ secretion over the control-treated group.

Example 9: Effect of TNFR2 Antibodies In Vitro Generated Exhausted CD8 T Cell

An in vitro model of T cell exhaustion was adopted as similarly established and characterized by Balkhi M. et al (iScience (2018) 2: 105-122). CD8 T cells were expanded under repeated stimulation with ImmunoCult™ (STEMCELL #10991) and cultured in ImmunoCult™-XF T Cell Expansion Medium (STEMCELL #10981) supplemented with human recombinant IL-2 (Biolegend #589106). The cells were characterized to ensure expression of exhaustion phenotypes by observing changes in surface markers and reduced cytokine secretion. Subsequently, the cells were cultured expansion medium supplemented with ImmunoCult™ and plated into 96-well plates in the presence of test antibodies at 10 μg/ml (66 nM) or isotype control. In some cases, anti-human Fcγ fragment specific $F(ab')_2$ (Jackson, #109-006-098) was added to the wells containing antibody. Cells were cultured in the presence of antibody with or without cross-linker. All the experiments were performed in triplicates.

Figure 8:
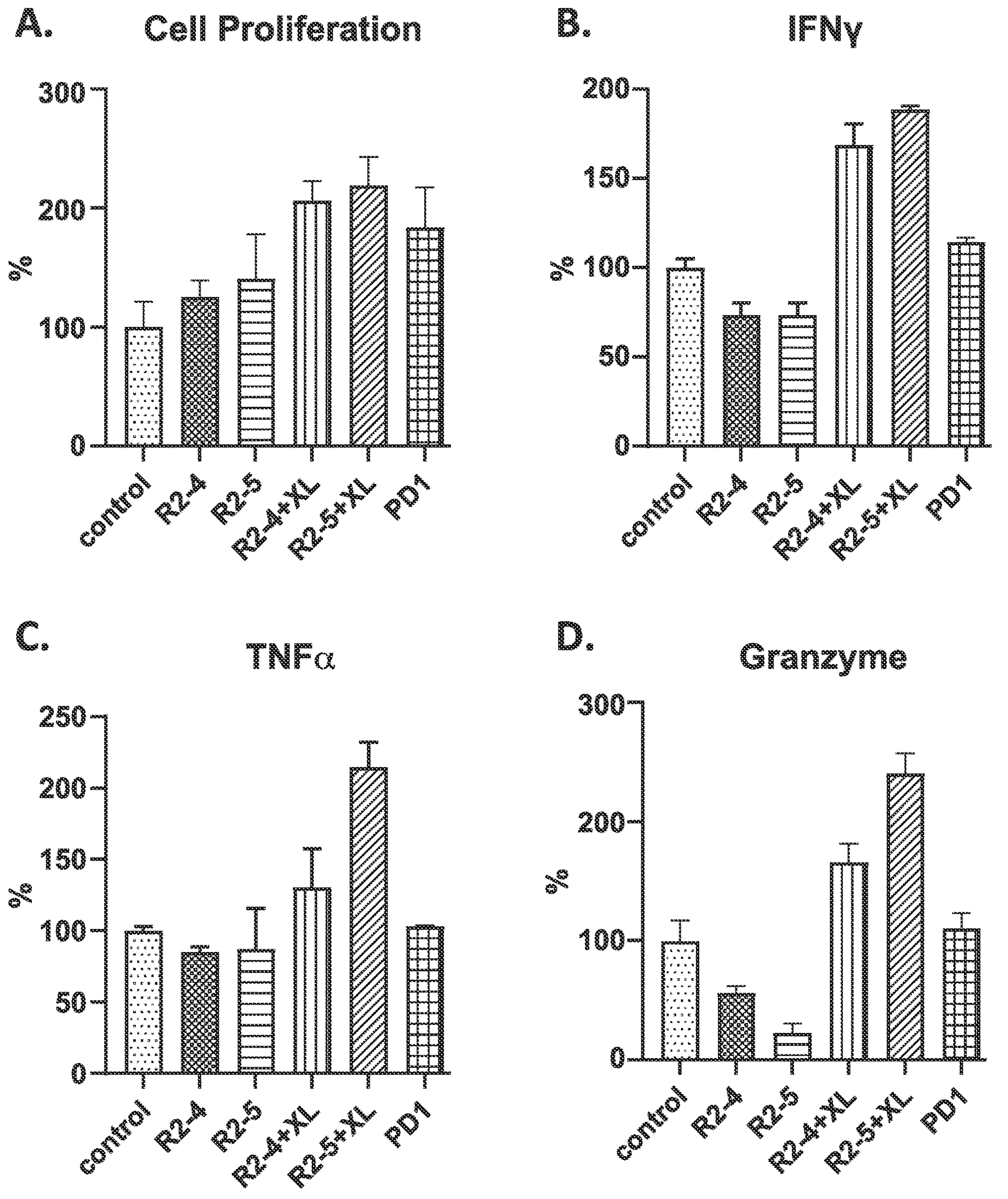

An increase in proliferation was not observed under the antibody alone conditions but the presence of cross-linker caused increased cell proliferation to isotype control antibody (FIG. 8A). Exhaustion of T cells is characterized by a gradual loss of IL-2, IFNγ and Granzyme B levels (data not shown). Supernatants were collected from the same wells in which T cell proliferation was measured and were analyzed using BD cytometric bead assay (CBA) for the presence of secreted human IFNγ (BD cat #558269), human Granzyme B (BD cat #560304) and human TNF (BD cat #560112). Cytokines concentrations were calculated based on the standard curve included in the kit. With the individual TNFR2 antibodies alone, the cytokine levels either decreased or were unchanged (FIG. 8).

In the presence of the crosslinker, the anti-TNFR2 antibodies caused an increased secretion in IFNγ (FIG. 8B), TNF (FIG. 8C), and Granzyme (FIG. 8D). In contrast, an anti-PD-1 antibody effected an increase in proliferation but was unable to promote any enhancement in IFNγ (FIG. 8B), TNF (FIG. 8C), and Granzyme (FIG. 8D).

Example 10: Anti-Tumor Efficacy of Anti-TNFR2 Antibodies in a hTNFR2 Knock-In Syngeneic Tumor Model Six to seven-week-old female homozygous B-hTNFR2 mice (C57BL/6-Tnfrsf1b$^{tm1(hTNFRSF1B)}$/Bcgen) from Biocytogen (Boston, MA) were injected with $5\times10^5$ viable MC38 cells in 0.1 mL PBS subcutaneously into the right flank. Seven days later, when the tumor size reached approximately 100 mm$^3$, the mice were randomly sorted into groups, and treatment by intraperitoneal injection was initiated (Day 8). Group 1 received vehicle control; group 2 received 200 μg of R2_mAb-4 Ms IgG2a; group 3 received 200 μg of R2_mAb-5 Ms IgG2a. Treatment was administered twice a week for 3 weeks.

Body weights were measured twice weekly. Tumor volumes were determined at different time points using the formula $V=½*L\times W\times W$, where L is the long dimension and W is the short dimension of the xenograft. Any mice with tumors over 2500 mm$^3$ were sacrificed.

As shown in FIG. 9A, significant inhibition of tumor growth was observed in the mice treated with both R2_mAb-4 Ms IgG2a and R2_mAb-5 Ms IgG2a. On day 29 of the study, the p value was determined to be <0.0001 for both treatments by one-way ANOVA analysis (FIG. 9B). Furthermore, treatment with both R2_mAb-4 MsIgG2a and R2_mAb-5 MsIgG2a had no effect on the body weight of the mice (data not shown).

Example 11: Evaluation of Anti-Tumor Efficacy in Combination with a PD-L1 Antibody in an MC38 Colon Cancer Model Six to seven-week-old female homozygous B-hTNFR2 mice (C57BL/6-Tnfrsf1b$^{tm1(hTNFRSF1B)}$/Bcgen) from Biocytogen (Boston, MA) were injected with $5\times10^5$ viable MC38 cells in 0.1 mL PBS subcutaneously into the right flank. Eight days later, when the tumor size reached approximately 100 mm$^3$, the mice were randomized into groups, and treatment by intraperitoneal injection was initiated (Day 8). Group 1 received vehicle control; group 2 received 60 μg of anti-mPD-L1 antibody; group received 100 μg of R2_mAb-5 MsIgG2a; group 3 received 100 μg of R2_mAb-5 MsIgG2a together with 60 μg of anti-mPD-L1 antibody. The anti-mPD-L1 antibody was provided by Biocytogen based on the public sequence information of atezolizumab. Treatment was administered twice a week for 3 weeks.

Body weights were measured twice weekly. Tumor volumes were determined at different time points using the formula $V=½*L\times W\times W$, where L is the long dimension and W is the short dimension of the xenograft. Any mice with tumors over 2000 mm$^3$ were sacrificed. The survival of the mice was monitored up to 63 days post tumor implantation.

As shown in FIG. 10A, single agent R2-mAb5 MsIgG2a at 5 mpk exhibited 91.7% tumor growth inhibition (TGI) on day 32. Anti-mPD-L1 when administered alone at 3 mpk resulted in 71.4% TGI. However, when R2-mAb5 MsIgG2a are administered in combination with PDL1 blockade, the TGI value became 96% on day 32. The benefit of TNFR2 in combo with PDL1 blockage was also shown in the survival analysis in FIG. 10B, mice from the control did not survive for more than 39 days. Anti-mPD-L1 antibody treatment led to 14% survival at the end of the study observation. In contrast, mice treated with R2_mAb-5 MsIgG2a either as a single agent or in combination with anti-mPD-L1 yielded a survival of 50% and 63%, respectively.

Example 12: Evaluation of a TNFR2 Antibody in a PD1 Resistant Model B16F10

To predict the therapeutic potential of TNFR2 antibody treatment in PD1 resistant patients, a PD1 resistant tumor model B16F10 melanoma model was used to compare the efficacy of single agent anti-TNFR2 antibody and anti-TNFR2 treatment in combination with PDL1 blockade. Six to seven-week-old female homozygous B-hTNFR2 mice (C57BL/6-Tnfrsf1b$^{tm1(hTNFRSF1B)}$/Bcgen) from Biocytogen (Boston, MA) were injected with $1\times10^5$ viable B16-F10 cells in 0.1 mL PBS subcutaneously into the right flank. Eight days later, when the tumor size reached between 75 and 100 mm$^3$, the mice were randomized into groups, and treatment by intraperitoneal injection was initiated (Day 8). Group 1 received vehicle control; group 2 received 60 μg of anti-mPD-L1 antibody; group received 100 μg of R2_mAb-5 MsIgG2a; group 3 received 100 μg of R2_mAb-5 MsIgG2a together with 60 μg of anti-mPD-L1 antibody. Treatment was administered twice a week for 3 weeks.

Body weights were measured twice weekly. Tumor volumes were determined at different time points using the formula V=½*L×W×W, where L is the long dimension and W is the short dimension of the xenograft. Any mice with tumors over 2500 mm; were sacrificed. The survival of the mice was monitored up to 26 days post tumor implantation.

As shown in FIG. 11, mice from the 5 mpk anti-mPD-L1 antibody treated group had a TGI value of 19.3% on day 15 post-inoculation, 5 mpk R2_mAb-5 MsIgG2a treatment had a 34% TGI value. When R2_mAb-5 MsIgG2a in combination with anti-mPD-L1 yielded a TGI value of 58%, better than the single agent treatment of either PDL1 or TNFR2.

Example 13: The Efficacy of a TNFR2 Antibody is not Entirely Dependent on ADCC The high expression level of TNFR2 on Treg cells present in the tumor microenvironment leads to the hypothesis that ADCC-mediated depletion of Tregs explains the efficacy of anti-TNFR2 antibodies. We evaluated the efficacy of R2_mAb-5 in both mouse IgG2a format (ADCC competent) and mouse IgG1 format (ADCC inert).

Six to seven-week-old female homozygous B-hTNFR2 mice (C57BL/6-Tnfrsf1b$^{tm1(hTNFRSF1B)}$/Bcgen) from Biocytogen (Boston, MA) were injected with 5×10$^5$ viable MC38 cells in 0.1 mL PBS subcutaneously into the right flank. Eight days later, when the tumor size reached approximately 100 mm$^3$, the mice were randomly sorted into groups, and treatment by intraperitoneal injection was initiated (Day 8). Group 1 received vehicle control; group 2 received 200 μg of R2_mAb-5 Ms IgG2a; group 3 received 200 μg of R2_mAb-5 Ms IgG1. Treatment was administered twice a week for 3 weeks.

Body weights were measured twice weekly. Tumor volumes were determined at different time points using the formula V=½*L×W×W, where L is the long dimension and W is the short dimension of the xenograft. Any mice with tumors over 2500 mm$^3$ were sacrificed.

As shown in FIG. 12A, significant inhibition of tumor growth was observed in the mice treated with both of R2_mAb-5 Ms IgG2a and R2_mAb-5 Ms IgG1. On day 32 of the study, the p value was determined to be <0.0001 for both treatments by one-way ANOVA analysis (FIG. 12B). The tumor inhibition was slightly stronger with R2-5 R2_mAb-5 Ms IgG2a compared to R2_mAb-5 Ms IgG1, but the difference is not statistically significant. This result suggests that ADCC contributes to the anti-tumor efficacy of R2-mAb5, but the efficacy is not fully dependent on ADCC.

Example 14: The Anti-Tumor Efficacy of a TNFR2 Antibody is Partially Dependent on Fc Receptor Cross-Linking Activity To further deconvolute the mechanism of action of TNFR2 antagonist antibodies, the efficacy of R2_mAb-5 was evaluated in both mouse IgG2a format (ADCC competent) and mouse IgG1 D265A format (ADCC and Fc crosslinking inert), since replacement of aspartic acid by alanine at position 265 (D265A) in mouse IgG1 results in a complete loss of interaction between this isotype and low-affinity IgG Fc receptors (Fc gammaRIIB and Fc gammaRIII).

Six to seven-week-old female homozygous B-hTNFR2 mice (C57BL/6-Tnfrsf1b$^{tm1(hTNFRSF1B)}$/Bcgen) from Biocytogen (Boston, MA) were injected with 5×10$^5$ viable MC38 cells in 0.1 mL PBS subcutaneously into the right flank. Eight days later, when the tumor size reached approximately 100 mm$^3$, the mice were randomly sorted into groups, and treatment by intraperitoneal injection was initiated (Day 8). Group 1 received vehicle control; group 2 received 100 μg of R2_mAb-5 Ms IgG2a; group 3 received 200 μg of R2_mAb-5 Ms IgG2a, and group 4 received 100 μg of R2_mAb-5 Ms IgG1D265A. Treatment was administered twice a week for 3 weeks.

Body weights were measured twice weekly. Tumor volumes were determined at different time points using the formula V=½*L×W×W, where L is the long dimension and W is the short dimension of the xenograft. Any mice with tumors over 2500 mm$^3$ were sacrificed.

As shown in FIG. 13A, significant inhibition of tumor growth was observed in the mice treated with both of R2_mAb-5 Ms IgG2a and R2_mAb-5 Ms IgG1 D265A. R2_mAb-5 Ms IgG2a showed a dose dependency, with Group 3 (10 mpk) demonstrated a stronger anti-tumor effect than Group 2 (5 mpk), TGI 89.9/o vs. TGI 71.4%. Moreover, if removed, the Fc crosslinking effect by using a MsIgG1 D265A variant, the antitumor effect was reduced to TGI 41.2%, indicating that the Fc function is required for the full extend anti-tumor effect of TNFR2 antibody R2_mAb5. On day 25 of the study, the p value was determined to be <0.0001 for both treatments by one-way ANOVA analysis (FIG. 13B). This result suggests that Fc crosslinking contributes to the anti-tumor efficacy of R2-mAb5, but the efficacy is not fully dependent on Fc-crosslinking.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

What is claimed is:

1. An anti-TNFR2 antibody comprising:

VH: CDR1: SEQ ID NO: 31, CDR2: SEQ ID NO: 32, CDR3: SEQ ID NO: 33, VL: CDR1: SEQ ID NO: 34, CDR2: SEQ ID NO: 35, and CDR3: SEQ ID NO: 36.

2. The anti-TNFR2 antibody of claim 1, wherein the antibody comprises:

a heavy chain variable region having the sequence set forth in SEQ ID NO: 7 and a light chain variable region having the sequence set forth in SEQ ID NO: 8.

3. The anti-TNFR2 antibody of claim 2, wherein the antibody comprises a heavy chain constant region as set forth in SEQ ID NO: 50.

4. The anti-TNFR2 antibody of claim 2, wherein the antibody comprises a light chain constant region as set forth in SEQ ID NO: 51.

5. The anti-TNFR2 antibody of claim 1, wherein the antibody is a fully human antibody.

6. The anti-TNFR2 antibody of claim 1, wherein the antibody is a chimeric antibody.

7. The anti-TNFR2 antibody of claim 1, wherein the antibody is a bispecific antibody or multispecific antibody.

8. The anti-TNFR2 antibody of claim 1, wherein the antibody is a humanized antibody.

9. The anti-TNFR2 antibody of claim 1, wherein the antibody is an antibody fragment.

10. The anti-TNFR2 antibody of claim 9, wherein the antibody fragment is selected from the group consisting of: Fab, F(ab)2, Fd, Fv, scFv, scFv-Fc fragment, a single-chain antibody, a minibody, and a diabody.

11. A pharmaceutical composition comprising as an active ingredient, at least one antibody according to anyone of claims 1 to 10 and a pharmaceutically acceptable carrier.

12. A method of treating cancer comprising administering to a subject in need thereof, a pharmaceutical composition according to claim 11.

13. An isolated polynucleotide comprising a sequence encoding an anti-TNFR2 antibody according to claim 1.

14. An isolated polynucleotide according to claim 13, encoding a sequence as set forth in any one of SEQ ID NOS: 7 or 8.

15. A vector comprising a polynucleotide according to claim 14.

16. A host cell comprising a polynucleotide according to claim 14, and/or a vector according to claim 15.

17. A method for the production of an anti-TNFR2 antibody comprising culturing the host cell of claim 16.

* * * * *